(12) United States Patent
Stefanon et al.

(10) Patent No.: US 7,873,482 B2
(45) Date of Patent: Jan. 18, 2011

(54) DIAGNOSTIC SYSTEM FOR SELECTING NUTRITION AND PHARMACOLOGICAL PRODUCTS FOR ANIMALS

(76) Inventors: Bruno Stefanon, via Zilli, 51/A/3, Martignacco (IT) 33035; W. Jean Dodds, 938 Stanford St., Santa Monica, CA (US) 90403

( * ) Notice: Subject to any disclaimer, the term of this patent is extended or adjusted under 35 U.S.C. 154(b) by 158 days.

(21) Appl. No.: 12/316,824

(22) Filed: Dec. 16, 2008

(65) Prior Publication Data

US 2010/0153016 A1    Jun. 17, 2010

(51) Int. Cl.
*G06F 19/00*    (2006.01)
(52) U.S. Cl. ....................................................... 702/19
(58) Field of Classification Search ................... 702/19, 702/23, 182–185
See application file for complete search history.

(56) References Cited

U.S. PATENT DOCUMENTS

| | | | |
|---|---|---|---|
| 3,995,019 | A | 11/1976 | Jerome |
| 5,691,157 | A | 11/1997 | Gong et al. |
| 5,817,025 | A | 10/1998 | Alekseev et al. |
| 5,830,709 | A | 11/1998 | Benson et al. |
| 5,911,687 | A | 6/1999 | Sato et al. |
| 5,954,640 | A | 9/1999 | Szabo |
| 6,018,786 | A | 1/2000 | Krick et al. |
| 6,063,028 | A | 5/2000 | Luciano |
| 6,081,786 | A | 6/2000 | Barry et al. |
| 6,135,055 | A | 10/2000 | Pratt |
| 6,136,055 | A | 10/2000 | Stanek |
| 6,156,355 | A | 12/2000 | Shields, Jr. et al. |
| 6,218,122 | B1 | 4/2001 | Friend et al. |
| 6,232,522 | B1 | 5/2001 | Harley et al. |
| 6,287,254 | B1 | 9/2001 | Dodds |
| 6,358,546 | B1 | 3/2002 | Bebiak et al. |
| 6,493,641 | B1 | 12/2002 | Singh et al. |
| 6,537,213 | B2 | 3/2003 | Dodds |

(Continued)

FOREIGN PATENT DOCUMENTS

WO    WO 99-67642 A2    12/1999

(Continued)

OTHER PUBLICATIONS

Swanson, et al., "Nutritional Genomics: Implication for Companion Animals", The American Society for Nutritional Sciences, (2003) J. Nutr. 133:3033-3040 (18 pages).

(Continued)

*Primary Examiner*—Edward Raymond
(74) *Attorney, Agent, or Firm*—Greenberg Traurig, LLP

(57) ABSTRACT

An analysis of the profile of a non-human animal comprises: a) providing a genotypic database to the species of the non-human animal subject or a selected group of the species; b) obtaining animal data; c) correlating the database of a) with the data of b) to determine a relationship between the database of a) and the data of b); c) determining the profile of the animal based on the correlating step; and d) determining a genetic profile based on the molecular dietary signature, the molecular dietary signature being a variation of expression of a set of genes which may differ for the genotype of each animal or a group of animals Nutrition and pharmalogical assessments are made. Reporting the determination is by the Internet, and payment for the report is obtained through the Internet.

24 Claims, 23 Drawing Sheets

U.S. PATENT DOCUMENTS

| | | | |
|---|---|---|---|
| 6,730,023 | B1 | 5/2004 | Dodds |
| 7,029,441 | B2 | 4/2006 | Dodds |
| 7,134,995 | B2 | 11/2006 | Dodds |
| 7,296,537 | B2 | 11/2007 | Burghardi et al. |
| 2002/0022772 | A1 | 2/2002 | Dodds |
| 2003/0135096 | A1 | 7/2003 | Dodds |
| 2003/0233984 | A1 | 12/2003 | van de Ligt et al. |
| 2005/0090718 | A1* | 4/2005 | Dodds ................ 600/300 |
| 2006/0045909 | A1 | 3/2006 | Friesen et al. |
| 2006/0064250 | A1 | 3/2006 | Goldstein |
| 2006/0200320 | A1 | 9/2006 | Al-Murrani |
| 2007/0118295 | A1 | 5/2007 | Al-Murrani |

FOREIGN PATENT DOCUMENTS

| | | |
|---|---|---|
| WO | WO 01/28415 A1 | 4/2001 |
| WO | WO 01/69487 A1 | 9/2001 |
| WO | WO 2004/113570 A2 | 12/2004 |

OTHER PUBLICATIONS

Swanson, et al., "Diet Affects Nutrient Digestibility, Hematology, and Serum Chemistry of Senior and Weanling Dogs", Journal of American Science, (2004) J. Anim. Sci. 2004. 82:1713-1724 (19 pages).

Kato, et al., "A Perspective on DNA Microarray Technology in Food and Nutritional Science", Current Opinion in Clinical Nutrition and Metabolic Care, (2005) 8:516-522 (7 pages).

Spielbauer, et al., "Impact of Microarray Technology in Nutrition and Food Research", (2005) Mol. Nutr. Food Res., 49, 908-917 (10 pages).

Swanson, et al., "Canine Nutritional Model: Influence of Age, Diet, and Genetics on Health and Well-Being", Current Nutrition & Food Science, vol. 2, No. 2, May 2006, pp. 115-126(12) (1 page).

M.F. Bottcher, M.F. et al., "Total and allergen-specific immunoglobulin A levels in saliva in relation to the development of allergy in infants up to 2 years of age" Clin. Exp. Allergy Sep. 2002, vol. 32, No. 9, pp. 1293-1298.

A.P. Foster et al., "Serum IgE and IgG responses to food antigens in normal and atopic dogs, and dogs with gastrointestinal disease" Vet. Immunol. Immunopathol. May 2003, vol. 92, pp. 113-124.

M.J. Day et al. "The Canine Model of Dietary Hypersensitivity" Proc. Nutr. Soc. Nov. 2005, vol. 64, No. 4, pp. 458-464.

Dodds (Veterinary Practice, 1992, vol. 4, No. 2, p. 25-31).

Hetzel et al. (The Journal of Nutrition, 1989, vol. 119, p. 145-151).

Williams et al. (Nucleic Acids Research, 1990, vol. 18, No. 22, p. 6531-6535).

Dodds (Advances in Veterinary Science and Comparative Medicine, 1995, vol. 39, p. 29-95).

R. Wolter "La nutrition de l'animal de sport" Laboratoire de Nutrition sportive (INRA) Ecole Nationale Veterinaire d'Alfort, Science & Sports 2, (1987) p. 63-93.

Harrison et al. The Journal of Nutrition, 1987, vol. 117, p. 376-382.

K. McNutt, PhD., J.D., "The Individualized Prescriptive Foods Era Has Dawned", Nutrition Today, May/Jun. 1993, p. 43-47, USA.

* cited by examiner

Genotype A

| Functional Genomic Profile | Reference data set | Target data set | Test animal - Not normal | Nutrient data set - CA | Nutrient data set - CB | |
|---|---|---|---|---|---|---|
| TNF-a | 1 | 2 | 2 | -1 | -1 | |
| NFK-b | 1 | 2 | 2 | -1 | 0 | Biological Active |
| IL2 | 1 | 3 | 3 | -2 | -1 | Nutrient-A |
| IL6 | 1 | 4 | 4 | -3 | -4 | supplemented formula |
| COX-1 | 1 | 1 | 1 | 0 | -1 | |
| COX-2 | 1 | 2 | 2 | -1 | 0 | |

Genotype B

| Functional Genomic Profile | Reference data set | Target data set | Test animal - Not normal | Nutrient data set - CA | Nutrient data set - CB | |
|---|---|---|---|---|---|---|
| TNF-a | 1 | 2 | 2 | -2 | -1 | |
| NFK-b | 1 | 3 | 3 | 0 | -2 | Biological Active |
| IL2 | 2 | 5 | 5 | 0 | -3 | Nutrient-B |
| IL6 | 1 | 3 | 3 | -3 | -2 | supplemented formula |
| COX-1 | 2 | 3 | 3 | 1 | -1 | |
| COX-2 | 1 | 3 | 3 | -1 | -2 | |

*FIG. 5B*

| REFERENCE DATASET ANIMALS (Healthy) | | | | | TARGET DATASET ANIMALS (Test Animals) (Unhealthy/Unknowns) | | | | | NUTRIENT DATASET | | | | |
|---|---|---|---|---|---|---|---|---|---|---|---|---|---|---|
|  | G1 | G2 | G3 | G4 |  | G1 | G2 | G3 | G4 |  | G1 | G2 | G3 | G4 |
| △ | 1 | 1 | 1 | 1 | □* | 1 | 2 | 1 | 1 | □ |  |  |  |  |
| ○ | 1 | 2 | 1 | 1 | △# | 1 | 1 | 1 | 2 | CA | -1 | -1 | -1 | -1 |
| □ | 1 | 2 | 2 | 1 |  |  |  |  |  | CB | 0 | 0 | +1 | 0 |
| ○ | 1 | 2 | 1 | 1 |  |  |  |  |  | CC | 0 | +1 | 0 | +1 |
| ○ | 1 | 1 | 1 | 1 |  |  |  |  |  | △ |  |  |  |  |
| △ | 1 | 2 | 1 | 1 |  |  |  |  |  | CA | +1 | 0 | 0 | +1 |
| □ | 1 | 2 | 2 | 1 |  |  |  |  |  | CB | -1 | 0 | +1 | -1 |
|  |  |  |  |  |  |  |  |  |  | CC | 0 | 0 | 0 | -1 |

* As G3 was not 2, as seen in reference set □ profile, add appropriate nutrient(s)

CB for □

As G4 was not 1, as seen in reference set △ profile, add appropriate nutrient(s)

CC for △

FIG. 5C

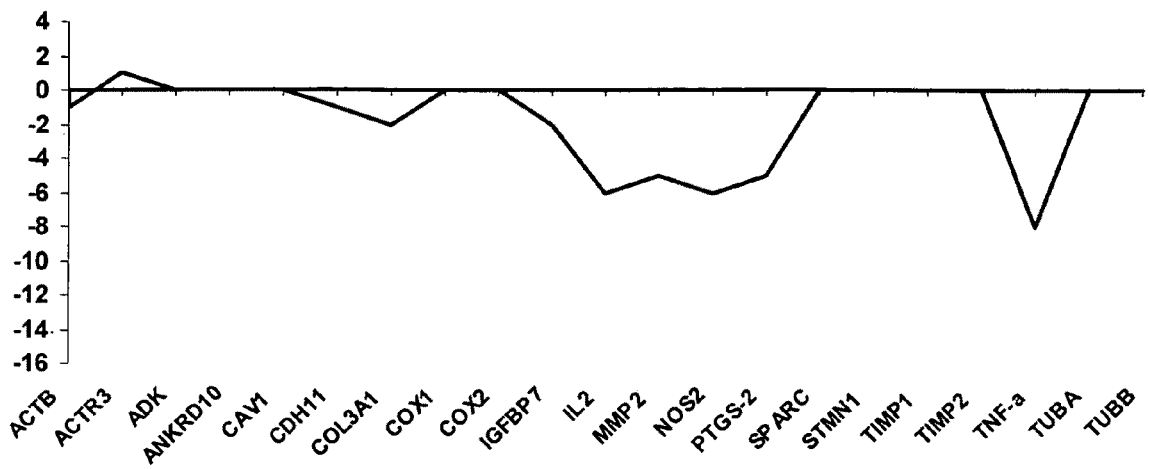
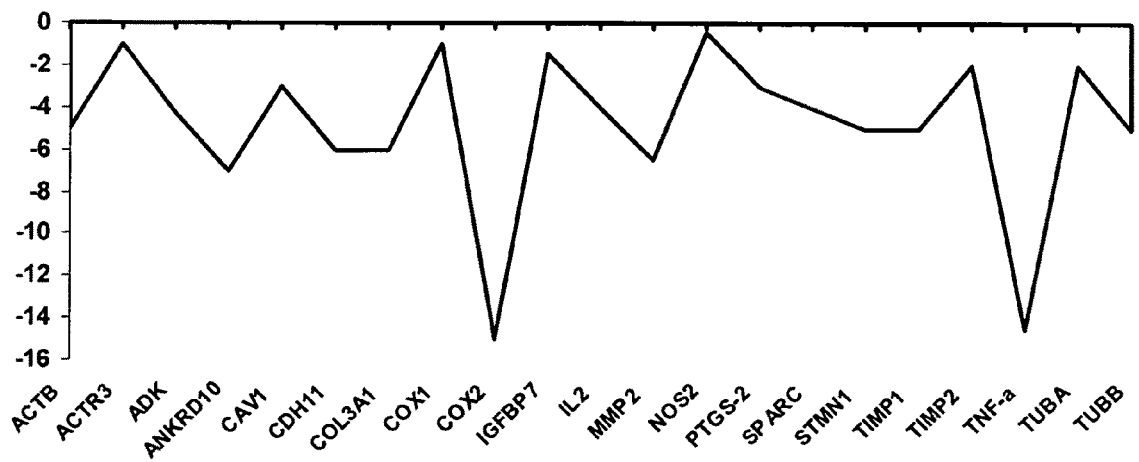
FIG. 9

DIAGNOSTIC SYSTEM FOR SELECTING NUTRITION AND PHARMACOLOGICAL PRODUCTS FOR ANIMALS

BACKGROUND

This disclosure is concerned with animal nutrition diagnosis. More particularly the disclosure is directed to the testing and diagnosis of genetic issues relating to nutrition issues and disorders of companion animals, for instance dogs and cats.

Further this disclosure relates to a method, system and apparatus for the management of nutrition assessment in relation to animals worldwide. In particular, the disclosure relates to a bioinformatics system and its implementation in relation to animal biological, genetic and nutrition data.

More specifically the disclosure is directed to animal nutrition diagnosis and care, animal well-being and nutrition, and methods and systems for enhanced determination of these factors.

Breeders, owners, and caregivers of animals which can be companions, such as dogs, cats, horses, farm, food, or zoo animals, and wildlife, have a need to understand the nutrition and biological attributes, and related genetic makeup and disorder background, particularly in relation to nutritional features.

Substantial investments in time, effort and financial resources are made by the breeders, owners, and caregivers of these animals, particularly purebred animals, to characterize their nutrition state. There is also a need to conduct periodic comprehensive nutrition assessments of animals.

The probability that an individual animal will develop a specific nutrition-related condition in its lifetime is a product of complex interactions between its genetic makeup, environmental influences including diet, and agents of disease (e.g., chemical, physical, or biological) that the animal encounters.

The physical attributes and other descriptive and nutrition assessment information are generally termed in this application as the phenotypic information. Genetic trait or disorder information is termed in this application as the genotypic information. Generally, these are two distinct and differing sets of information.

Current laboratory and research systems and computerization have not achieved comprehensive nutrition assessments of animals, and nor have communication protocols been used effectively in this technological area to facilitate such a relationship, or to provide relational bioinformatics database systems for management and dissemination of comprehensive and cumulative information for individual animals.

More specifically, it is necessary in animal nutrition diagnosis and care for comprehensive nutrition assessments of animals for diseases and disorders of animals be achieved in order to reduce morbidity and mortality, and improve the quality of life and lifespan. Currently this is not done in relation to the nutrition assessment data of an animal together with the genetic data related to that same animal. Current tests do not provide as much data as possible to attain correct nutritional diagnosis and disorder predictions with the net result of an improvement in the quality of life and increased longevity.

Various attempts have been made to customize, a nutrient or, food products for a specific animal and various methods have also been proposed, but these are not definitive when applied to different animals or species of animals.

The fields of nutrigenetics and nutrigenomics have opened the way in humans for "personalized nutrition", as pharmacogenetics and pharmacogenomics have led to the concept of "personalized medicine" and "designer drugs". Similar scientific advances and concepts are being applied to the nutrigenetics and nutrigenomics of animals. In other words, by understanding animal nutritional needs, animal nutritional status, animal physiological or pathophysiological conditions, animal functional genomic profiles and animal genotypes, nutrigenetics and nutrigenomics should enable better management or control of the health and well-being of individual animals or a group of animals by precisely matching their nutrient needs or dietary composition with their unique genetic makeup.

"DNA polymorphisms" (i.e. SNPs) have been used for animal genotyping, in order to identify breed characteristics, or disease susceptibility, or have been applied to group animal populations by one or more phenotypic traits according to the frequency of a set of genetic alleles.

The "functional genomic profile" is another technique used to identify breed characteristics, or disease susceptibility or is applied to group animal populations or an individual animal one or more by several phenotypic traits according to the pattern of gene expressions (genomics), or protein expressions (proteomics) or metabolites (metabolomics).

The specific interaction between the nutritional environment and the genome of an individual has been termed the molecular dietary signature of that individual It is important for nutritionists or other animal food professionals to prescribe or recommend nutrient needs or diets on the basis of more precise knowledge of how nutrients or food components interact at the level of the genome, where these constituents act by "up- or down-regulating" a set of target genes. Animal nutritionists or other animal food professionals should design nutrients or foods tailored to the genome or genomic profile or to prescribe or recommend the inclusion of specific molecules in the diets of animals to optimize physiological homeostasis, disease prevention and treatment, and productive or reproductive performances. Individualized nutrition requires an even more refined technique or approach than is currently available or applied.

The disclosure also relates to the application of pharmacogenetics to animals, namely the pharmacology dealing with the influence of genetic variation on the drug response of individual animals. It correlates the expression of genes or single-nucleotide genetic polymorphisms (called SNPs) with the efficacy or toxicity of a pharmaceutical product. The pharmacogenomics application of the disclosure relates to the identification and development to design and/or optimize pharmaceutical product therapy by taking the animal patient's genotype into account, and thereby improve pharmaceutical product efficacy with minimal adverse effects.

The disclosure also relates to pharmacogenomics as applied to a single or a few gene interactions with pharmaceutical products. The pharmacogenomics application of the disclosure considers the whole genome application of genetic technologies as they apply to the drugs and characterization of pharmaceutical products.

The development of genotype-specific pharmaceutical product therapy provides individuals with the opportunity for having uincreased efficacy and lower toxicity than currently available drugs. Several dozen polymorphisms of human pharmaceutical product—metabolizing enzymes have been characterized to date, but this has not been applied to animals who may have similar polymorphisms. The disclosure relates to the type and dose of pharmaceutical product prescribed for an animal as influenced by genotype.

SUMMARY

The disclosure uses genetic information of DNA polymorphism, the functional genomic profile, and the different response of an individual animal to a biologically active nutrient in order to identify and improve upon or optimize the nutrient composition of the diet for an individual animal.

A unique feature of the disclosure is that the response to a biologically active nutrient ingestion or exposure is a dynamic event since it depends upon the genetic variants of nutritionally inducible genes (polymorphisms, as SNPs) that can lead to a different effect of the biologically active nutrient in individual animals having different genotypes.

Effectively, the genotype of the individual animal is an essential component of this disclosure to permit the identification of the biologically active nutrient for that individual animal.

The assessment of the biologically active nutrient composition of the diet arises from using reference data relating to healthy animals with different genotypes, plus target data relating to animals affected with different physiological or pathophysiological states [termed "unhealthy animals"] and having different genotypes, and nutritional data relating to the different effects of nutritional compounds in healthy and unhealthy animals or groups of animals with different genotypes.

The assessment of the pharmacological product arises from using reference data relating to healthy animals with different genotypes, plus target data relating to animals affected with different physiological or pathophysiological states [termed "unhealthy animals"] and having different genotypes, and pharmacological data relating to the different effects of the pharmacological product in healthy and unhealthy animals or groups of animals with different genotypes.

Additional and further objects, features, and advantages of the present disclosure will be readily apparent to those skilled in the art.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 5A, 5B and 5C describe datasets showing the method of dynamic nutrient determination relative to FIGS. 6A and 6B.

FIG. 9 represents typical molecular dietary signatures respectively of two compounds, namely andrographolide and curcumin respectively.

DETAILED DESCRIPTION OF THE DISCLOSURE

Figure 1:
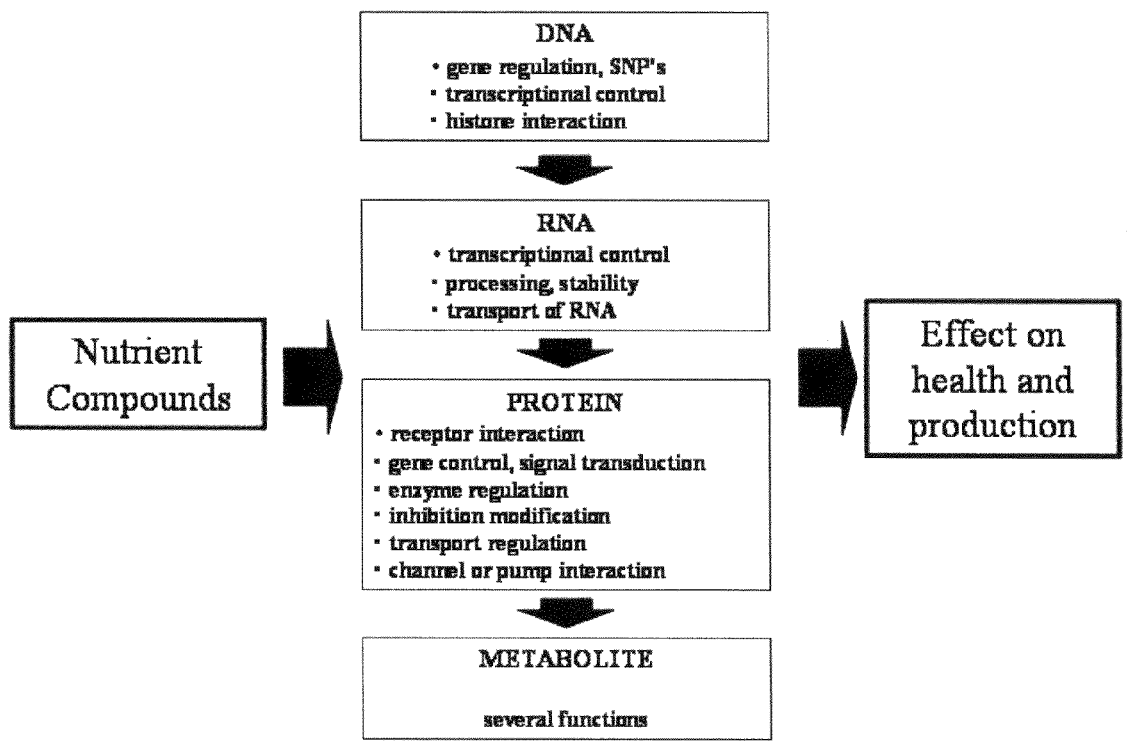
FIG. 1 describes the effect of a nutrient at different cellular and tissue levels.

The present disclosure provides methods and compositions for improving the health and/or well-being of an animal, in particular a companion-animal such as a dog or a cat. The disclosure-also provides for manufacturing, composing and providing the necessary biologically active nutrient or nutrients for animals.

The disclosure is concerned with nutritional genomics or nutrigenomics and nutrigenetics.

The disclosure includes a method of modulating the regulation of a gene or the protein expression or metabolites in an animal by nutritional management, including the step of analysing the gene or protein expressions or metabolites. Selected genes, proteins or metabolites in the samples are identified for a particular phenotypic parameter. The effect of a biologically active nutrient varies for different genotypes. A biologically active nutrient is provided to the animal to modulate the selected genes, proteins or metabolites so as to change the response of the animal to the particular phenotypic parameter in a desirable manner.

Typical genes, proteins and metabolites are, for example, those involved in the toxicology and nutrigenomics research (apoptosis, cell cycle, DNA damage signalling pathway, drug metabolism phase I and phase II enzymes, PI3K-AKT signalling pathway, toxicology and drug resistance), cytokines and inflammatory response (inflammatory cytokines and receptors, inflammatory response and autoimmunity, NFKβ signalling pathway, TNF ligand and receptor), metabolic diseases (diabetes, insulin signalling pathway, obesity, oxidative stress and antioxidant defences) and neurological disorders (depression, epilepsy, general anxiety disorders and panic disorders).

The animals can be selected from livestock, companion, sporting, working and different domesticated pet and laboratory animals, also including fish. These can include for example the following: birds, cat, cattle, dog, donkey, goat, guinea pig, hamster, horse, mouse, pig, poultry, quail, parrots, rabbit, rat, salmon, sheep, trout and turkey or exotic animals.

The phenotypic parameter can be, for example, growth, reproduction, lactation, maintenance, geriatric, inherited and acquired diseases, allergic, arthritic, autoimmune, inflammatory, metabolic and pathopsychological or psychological conditions.

The identification of the selected genes, proteins or metabolites in the sample can be effected by high throughput screening (HTS) techniques, such as microarray, pathway specific microarray, serial analysis of gene expression and gene sequencing. Alternative HTS methods to analyse the sample include proteomic and metabolomic assays.

The term "healthy" is a well defined term. In this application the term refers to an individual animal that has been determined to be well on the basis of physical examination, laboratory data of blood or other biological fluids or tissues, and the information provided by the animal's caregiver, owner or guardian.

The term "unhealthy" is a well defined term. In this application the term refers to an individual animal with physical or physiological or pathological or genetic deviation from the state of health.

The term "biologically active nutrient" in this application refers to a compound or composition or ingredient of an ingested material that has some biological measurable or documented effect in the body of an individual animal.

The method includes identifying a biologically active nutrient based on what is termed the "molecular dietary signature" that the biologically active nutrient induces in an individual animal, the molecular dietary signature being a variation of expression of a set of genes, protein or metabolites which may differ for the genotype of the individual animal.

The molecular dietary signature relates to the interaction between the nutritional environment and genome in an individual in the sense of nutritional genomics or nutrigenomics. The basic concept is that chemical nutrients affect gene expressions in a specific mode switching from health to a pathophysiological condition or vice versa. The advancement of knowledge in human and animal genomes and the spread of biotechnology offer the opportunity to individualize dietary intervention to prevent, mitigate or cure chronic diseases (i.e. individualized nutrition). The concept applies not only to companion pet animals, laboratory animals, but also to nutrient-genome interactions in farm animals. For farm animals, nutrigenomics can be applied for the improvement of productive performances, and the control of infectious and metabolic diseases, through the use of appropriated dietary compositions or supplements.

In companion pet animals, nutrigenomics can be directed to enhancement or maintenance of health and quality of life through the identification of the most suitable diet or supplementation to maintain or optimize the physiological health.

The animal genome and biotechnology systems, such as microarray platforms, can be used to modify the effect of nutrients on gene and protein expression profiles and the adaptation of animals to nutrient exposure, and as a mechanism to identify genetic variants with favorable or unfavorable traits. Nutrigenomics, namely the integration of functional genomics, nutrition, health and biological response, and the regulatory role of nutrients on gene expressions is enabled by microarray technology and integrated on an informatics platform. Nutrigenetics is the retrospective analysis of genetic variations among individuals with regard to their clinical response to specific nutrients.

The high throughput screening technologies are employed to identify a large number of markers or target molecules of a specific parameter treatment or pathology. This is applied to animal or pet nutrition to identify a set of genes, proteins, metabolites or other markers that are unique for a specific intake of each nutrient, chemical compound or xenobiotic. A specific nutrient affects body response in a form that is a molecular dietary signature.

This same concept as applied to gene expressions, measured with microarray technology, leads to the identification of a unique molecular dietary signature for each specific nutrient. In the case of gene expressions, the utilization of a public data repository allows the identification of a set of genes involved in biological processes, molecular function or cellular component, or in a mix of them, which are affected by the dietary change or composition. The three main classifications of gene functions are incorporated in the gene ontology project, which provides a controlled vocabulary to describe gene and gene product attributes in any organism. Other classifications are (KEGG, Kyoto Encyclopaedia of Gene and Genomes; and Biocarta) to identify the unique signature that a dietary change or composition is able to produce in an organism.

The signature of a particular nutrient can also vary from individual to individual, according to the DNA polymorphisms of the genes or genome. In the case that the genetic make-up of the individuals is known, the molecular dietary signature of mutant animals compared to that of wild-type animals forms a family of molecular signatures, which are used for the identification of the action of the nutrient.

EXAMPLE

Compound A is an anti-arthrosis natural plant extract which is fed to a group of 20 dogs, 10 healthy and 10 unhealthy dogs affected by arthrosis. The compound is fed for 15 days. Before and after the period of administration, a blood sample is drawn and used for a transcriptome analysis (gene expression) using a commercial oligomicroarray containing 44000 probes. The number of genes which significantly varied after the treatment is 73, when compared to those of the group of healthy animals that received a placebo.

Data mining using a public domain repository database and software indicated that the 73-gene variation of gene expression involved the Gene Ontology pathway response to stress, external stimuli, immune system process and cell communication. The average number of genes involved in each pathway is 15 (10 up-regulated and 5 down-regulated), 10 (5 up-regulated and 5 down-regulated), 23 (18 up-regulated and 5 down-regulated) and 25 (5 up-regulated and 20 down-regulated), respectively for a total of 73 genes (38 up-regulated and 35 down-regulated). These genes form a distinct cluster molecular dietary signature, which significantly differs from the level of expression of the placebo fed control group of dogs, and represent the action and response of the organism to the dietary compound. No other dietary compounds tested will produce the same molecular dietary signature when administered to dogs.

| Gene Ontology | Up-regulated | Down-regulated | Total |
| --- | --- | --- | --- |
| Response to stress | 10 | 5 | 15 |
| Response to external stimuli | 5 | 5 | 10 |
| Immune system process | 18 | 5 | 23 |
| Cell communication | 5 | 20 | 25 |
| Total | 38 | 35 | 73 |

However, in looking at the individual response for each dog of the group receiving Compound A, some variations occurred. In other words, if the average values are 38 genes up-regulated and 35 genes down-regulated, some of these genes will not change expression levels in some of the dogs receiving compound A. In the example, 5 of 10 dogs respond differently to the dietary administration of compound A.

| Gene Ontology | Up-regulated | Down-regulated | Total |
| --- | --- | --- | --- |
| Response to stress | 8 | 5 | 13 |
| Response to external stimuli | 5 | 2 | 7 |
| Immune system process | 10 | 5 | 15 |
| Cell communication | 4 | 18 | 22 |
| Total | 27 | 30 | 57 |

In the example, genotyping of these dogs indicated that the 5 individuals with a different response to the biologically active compound A presented a single nucleotide polymorphism (SNP) of the canine CYP1A2 gene that results in a deficiency of cytochrome P450 activity. For the biologically active compound A, two molecular dietary signatures are reported, one for each genotype.

There is a method of identifying a biologically active nutrient for an individual animal having a genotype, which comprises:

(a) using a "reference" dataset containing functional genomic profiles of biological samples of the genotypes of different animals of the species, the different animals being healthy animals;

(b) selecting a "target" dataset containing the functional genomic profile of biological samples of the genotypes of different animals, the different tanimals being unhealthy animals;

(c) using a "biologically active nutrient" dataset comprising different effects of biologically active nutritional components on functional genomic profiles of the different animals of different genotypes from those of the target group (b), the different genotypes being differently responsive to the same biologically active nutritional components; and (d) having the reference dataset or target dataset include an individual animal for which the biologocallly active nutrient is to be identified.

At least one of the "reference" or "target group" datasets is related with the "biologically active nutrient" dataset to identify a biologically active nutrient for the selected animal genotype to prevent, treat, control, or modulate a state of physiological homeostasis or pathophysiological condition of the individual animal in the reference dataset or target group.

The identification is based on the molecular dietary signature being the expression of a gene or a set of genes which may differ for the genotypes of different animals of the same species. The nutrient identification includes the molecular dietary signature that the biologically active nutrient induces in the individual animal.

The animal can be either a canine or a feline. The canine or feline is from the group consisting of one or more breed type, specific breed, chronological age, physiological age, activity level, healthy, and unhealthy.

The pathophysiological phenotypic conditions can be any one or more examples of any inherited or acquired diseases or conditions such as autoimmunity, anxiety, arthritis, depression, variable body condition score, immune suppression, inflammation, aural disease, skin, aging and behavioral changes, cancer or neoplasia, cardiovascular disease, ocular disease, orthopedic disease, endocrine disease, hematogical disease, kidney disease, gastrointestinal disorders including inflammatory bowel disease (IBD), acute or chronic diarrhea, exocrine pancreatic insufficiency, mal-digestion and pancreatitis, hepatic disorder, liver disease, obesity, dental disease, and pulmonary disease.

The data of the individual animal can be one or more data items related to genotype, including breed, breed(s) of parents, pedigree, sex, coat type, and evident hereditary conditions and disorders. Physiological related conditions include one or more of age, weight, veterinary medical history, reproductive history, health or unhealthy conditions, appetite, physical activity level, mental acuity, behavioral abnormalities and disposition.

The reference data can include one or more data of DNA, RNA, proteins, metabolites and biomarkers selected from an individual animal or groups of animals with different genotypes in physiological homeostasis.

The target group data can include one or more data of DNA, RNA, proteins, metabolites and biomarkers selected from an individual animal or groups of animals with different genotypes in non-physiological homeostasis.

The biologocallly active nutrient data can include one or more data of DNA, RNA, proteins, metabolites and biomarkers selected from an individual animal or groups of animals with different genotypes, the different genotypes being responsive differently to the same nutritional components.

The data comprise analytical data from a biological sample obtained from an individual animal.

The identified nutrient can be one or more of a food, part of a food, a supplement, a nutraceutical or any biologocalily active nutrient selected to enhance an aspect of health of an animal. Health can be promoted by preventing, attenuating or eliminating at least one disease state in one or more animals or by restoring physiological homeostasis.

A food composition is prepared as a result of the identified nutrient, achieved by this method.

The disclosure also includes a method of diagnosing a healthy, unhealthy or physiological disorder, or a predisposition to disease or physiological disorder for an individual animal having a genotype, comprising:

(a) using a "reference" dataset containing functional genomic profiles of biological samples of the genotypes of different animals of the species, the different animals being healthy animals;

(b) selecting a "target" dataset containing the functional genomic profile of biological samples of the genotypes-of different animals, the animals being unhealthy animals;

(c) using a "biologically active nutrient" dataset comprising different effects of biologically active nutritional components on functional genomic profiles of the different animals of different genotypes from those of the target group (b), the different genotypes being differently responsive to the same biologically active nutritional components; and (d) having the reference dataset or target dataset include an individual animal for which the biologocalily active nutrient is to be identified.

At least one of the "reference" or "target group" datasets is related with the "biologically active nutrient" dataset to identify a biologically active nutrient for the selected animal genotypes to prevent, treat, control, or modulate a state of physiological homeostasis or pathophysiological condition of the individual animal in the reference dataset or target group.

In another aspect of the disclosure there is a method of identifying a biologically active nutrient for animals, comprising:

(a) using a "reference" dataset containing functional genomic profiles of biological samples of the genotypes of different animals of the species, the different animals being healthy animals;

(b) selecting a "target group" dataset containing the functional genomic profile of biological samples of the genotypes of different animals, the animals being unhealthy animals;

(c) using a "biologically active nutrient" dataset comprising different effects of biologically active nutritional components on functional genomic profiles of the different animals of different genotypes from those of the target group (b), the different genotypes being differently responsive to the same biologically active nutritional components; and (d) having the reference group or target group include the animals.

At least one of the "reference" or "target group" datasets is related with the "biologically active nutrient" dataset to identify a biologically active nutrient for the selected animal genotypes to prevent, treat, control, or modulate a state of physiological homeostasis or pathophysiological condition of the animal in the reference dataset or target group. The analysis is affected by gene or protein expression or the metabolite expression in the biological samples of the target dataset.

The exact number of genes needed to create organisms has still to be defined for most of the animal species, and it is likely that the total number of transcripts ranges from 30,000 to 100,000. Irrespective of that number, the challenge remains to understand the role of the genes in terms of development, intake of nutrients, disease and physiological functions. The interaction between nutrients and cellular or genetic processes is a step in the post-genomic research and is a relatively new area of knowledge, referred as "nutritional genomics" or "nutrigenomics", a discipline aimed at the description of the global expression pattern of a cell or of tissues in different environmental conditions or the change of the expression patterns of these genes as a consequence of physiological cues, nutrition and diseases. The initial concept applied to humans, but also has been shown to apply to animals.

While nutrigenomics is the identification of the appropriate nutrient to modify the phenotype, based on nutrient-inducible genes, nutrigenetics represents the identification of the appropriate nutrient for a defined genotype. Nutrigenetics is an applied science, driven by the paradigms of nutritional pharmacology, the onset of genetic polymorphism, and of clinical experience. Nutrigenomics is a discovery science, driven by the paradigms of molecular biology, enabled by microarray technology, and integrated on an informatics platform.

The role of gene-nutrient interaction is recognized for some monogenic and multi-factorial defects. Monogenic diseases are determined by a single gene and multi-factorial diseases by the combination of several genes with other non-genetic factors. Sometimes, the classification may be an oversimplification, since monogenic diseases also may involve more than a single gene and environmental factors can modulate the expression of phenotype. Some classical monogenic diseases in humans are phenylketunuria, galactosemia, lactose intolerance and celiac disease. In most of the case of monogenic disease, dietary intervention can be used to avoid or treat the patients. In the case of phenylketunuria, an autosomal recessive defect resulting from a deficiency of phenylalanine hydroxylase which leads to mental retardation, a phenylalanine restricted diet avoids the severe consequences of the disease. Similarly, galactosemia, an autosomal defect, is related to the deficiency of one of the three main enzymes involved in galactose metabolism (galactose-1-phosphate uridyltransferase, galactokinase, uridine-diphosphate galactose-4' epimerase), impairing galactose metabolism, resulting in feeding difficulties, and prolonged conjugated hyperbilirubinemia during neonatal life. Avoidance of breast feeding and galactose in the diet prevent the consequences of this defect.

Among the multi-factorial chronic/age-related diseases, cardiovascular diseases, and metabolic syndrome, cancer, osteoporosis and neurological diseases are some classical examples in humans and these syndromes are generally associated with the aging process. Senescence is an obligate fate of cells, but gaining the knowledge of the gene-environment interactions can be effective in reducing the gap between normal and ideal—healthy—aging. Dietary factors are relevant for the onset and progression of degenerative diseases and solid scientific evidence has to be provided to support nutritional intervention. Also the multi-factorial chronic/age related diseases respond in a different way according to the genotype of the individual animal, leading to a so-called "individual susceptibility" or "genetic risk factor".

The disclosure integrates the concepts of nutrigenetics with that of nutrigenomics, considering:

(a) the different genetic make up of individual animals, or a group of them;

(b) the different functional genomic profile for different phenotypic classes of animals (namely healthy, unhealthy, affected, not affected, physiological states, pathophysiological conditions); and (c) the variable response of an individual animal or group of animals to a nutrient.

FIGS. 1 to 13 inclusive represent the concepts of nutrigenetics and nutrigenomics. The system and the method of the disclosure permits the design of food and nutrients for an individual animal, and to diagnose the healthy condition of an animal.

FIG. 1 shows in detail how a nutrient can affect the biological response of an animal at the DNA, RNA, protein or metabolite levels. Nutrients can affect gene transcriptions directly, as ligands for transcription factor receptors, or indirectly, as primary or secondary metabolic pathways, thereby altering concentrations of substrates or intermediates and signal transduction pathways and signaling. The alteration of expression of a subset of genes in the genome is achieved by acting at several levels (Clarke and Kim, 1998; Van Ommen, 2004), through effector genes, effects on enzymes and modification of metabolites and their concentrations.

The effect of a nutrient is thus related not only to the genetic background of the individual, i.e. the polymorphism of the DNA, but also to the interaction between nutrients and the coordinated regulation of gene expression, enzyme activities and metabolites. DNA variability among individuals (SNPs) is statistically associated with the effect of a nutrient on groups of animals, but does not consider the variations seen within individuals that relate to the effect that different environmental factors have on genotype.

The analysis of gene or protein expressions or metabolites in a biological sample permits accurate description of the physiological or patho-physiological conditions of the animal, thereby indicating which molecular, cellular or metabolic pathways need to be considered for dietary intervention.

The relevance of using gene expression data in relation to functional gene annotation is explained by the Gene Ontology (GO) project (http://www.geneontology.org/). This project provides a controlled vocabulary to describe the gene and gene product attributes in any organism. The GO project has developed three structured controlled vocabularies (ontologies) that describe gene products in terms of their associated biological processes, cellular components and molecular functions in a species-independent manner. According to GO, a single gene can be associated with different functions, for example Murine PI3K (phosphoinositide-3-kinase) has the following ontologies: biological process, negative regulation of apoptosis; biological process, protein amino acid phosphorylation; and molecular function, protein binding.

The multitasking role of this gene, as with many others, requires the understanding of the specific pathway or pathways involved in the observed biological response to the environment.

Another example is the v-raf-leukemia viral oncogene 1, which is associated with: biological process, apoptosis; biological process, cytoskeleton organization; cellular component, cytosol; and molecular function, protein kinase activity. Furthermore, these genes can be regulated from (upwards) or can regulate (downwards) other genes, thus altering one or more biological response, according to the type of environmental stimulus, its intensity and duration. The analysis of the polymorphisms of these multitasking genes indicate their genetic variability and can be statistically associated to a specific pathological state, which depends upon the design of the experiment, but does not identify which pathway is really associated in that particular individual. Instead, the simultaneous determination of a large number of genes expressed in a tissue or biological fluid and the use of appropriated informatic tools for data mining clearly indicate which molecular, cellular and metabolic pathway has been invoked by the environmental stimulus.

Figure 2:
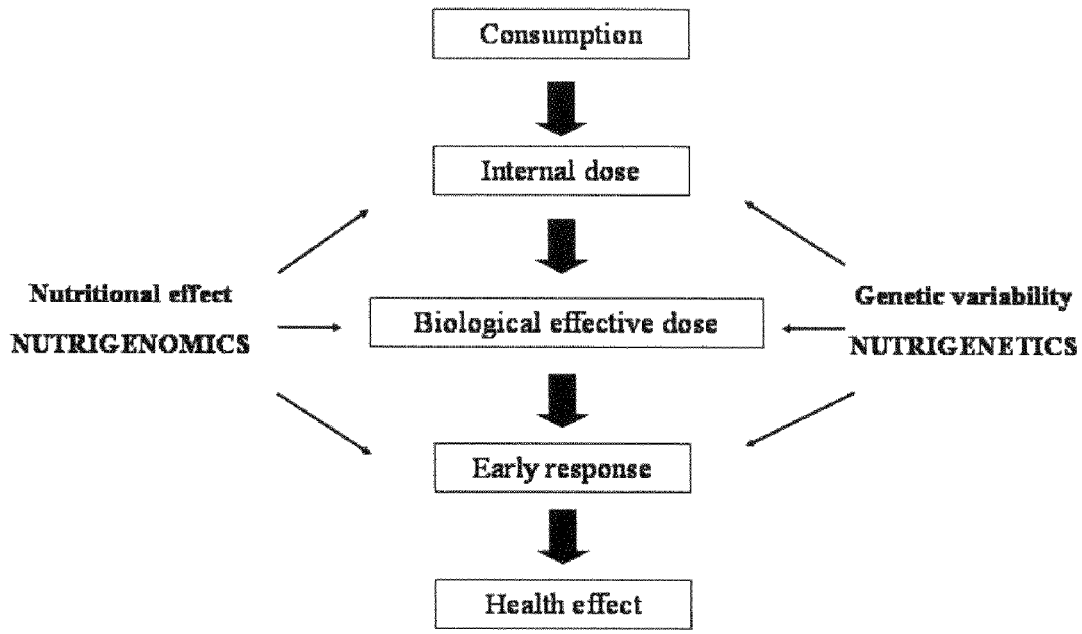
FIG. 2 describes the dynamic integration between nutrigenetic and nutrigenomic systems.

FIG. 2 summarizes the dynamic integration between the nutritional effect and the genetic variability. Nutrients interact with an animal phenotype by modulating the biological response (nutrigenomic effect) but the level of modulation depends upon the genotype of individual animals (nutrigenetic effect).

For instance, the assessment of SNPs of all the genes involved in the ADME is more closely related to the nutrigenetic effect of a composition, but does not take into account the complex interaction that the composition has at the molecular level, considering that genes have a multitasking action. The activation of the transcription of a gene or of a set of genes determines the activation of other genes, and the translated proteins can have a positive or negative feedback activity on the same gene from which they originated.

Figure 3:
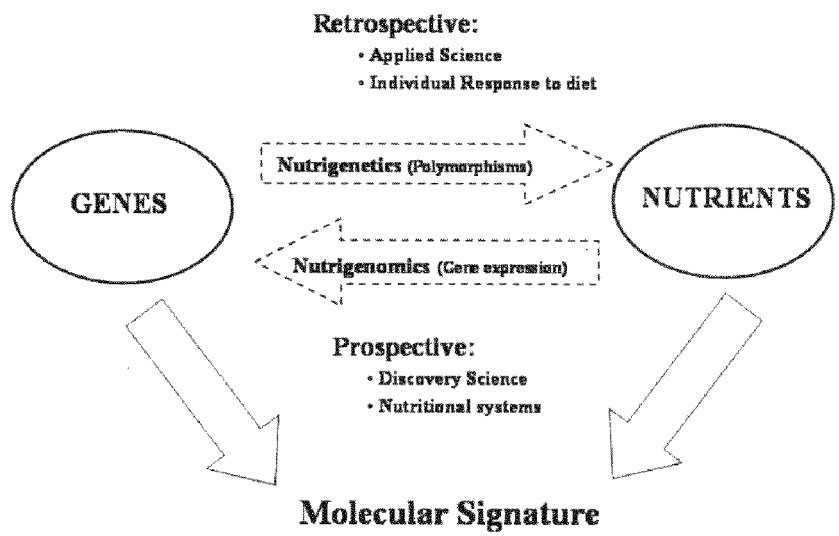
FIG. 3 describes the relationship between nutrigenomics and nutrigenetics, leading to a molecular dietary signature.

The integration between nutrigenetic and nutrigenomic effects is shown in FIG. 3. This leads to a unique fingerprint for each nutrient and for each group of animals sharing an identical genotype, whether this fingerprint is a "molecular dietary signature", in the case of RNA, or a "protein signature" in the case of proteome, or a "metabolic signature" in the case of metabolome.

This fingerprint arises from a retrospective analysis (i.e. SNPs of DNA) and from a perspective view of the interaction of a nutrient with cell activity at a molecular level and gives the "molecular dietary signature", in the case of RNA, or "protein signature" in the case of proteome, or "metabolic signature" in the case of metabolome.

Figure 4A:
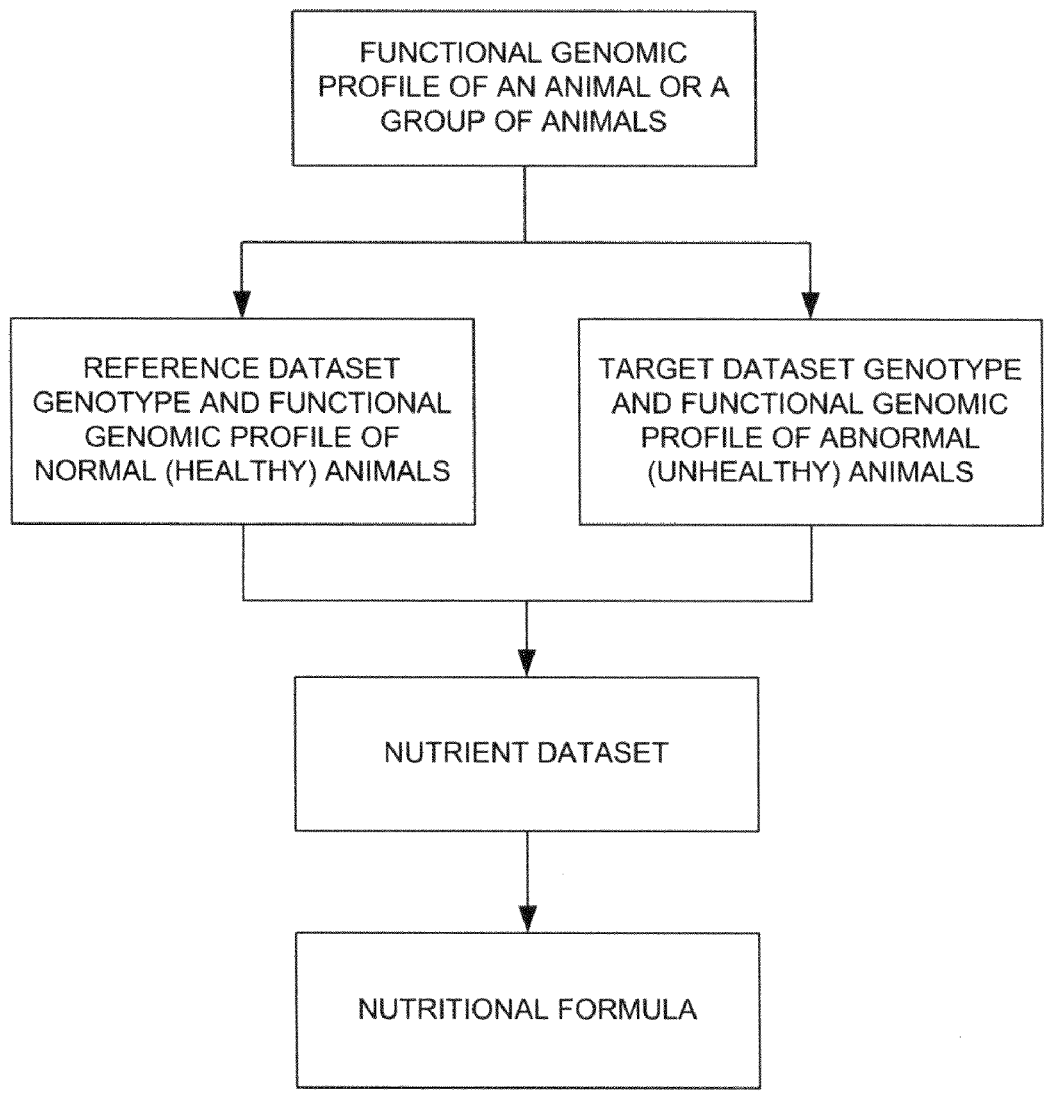
FIGS. 4A and 4B describes a flow diagram showing the method of dynamic nutrient determination.
Figure 4B:
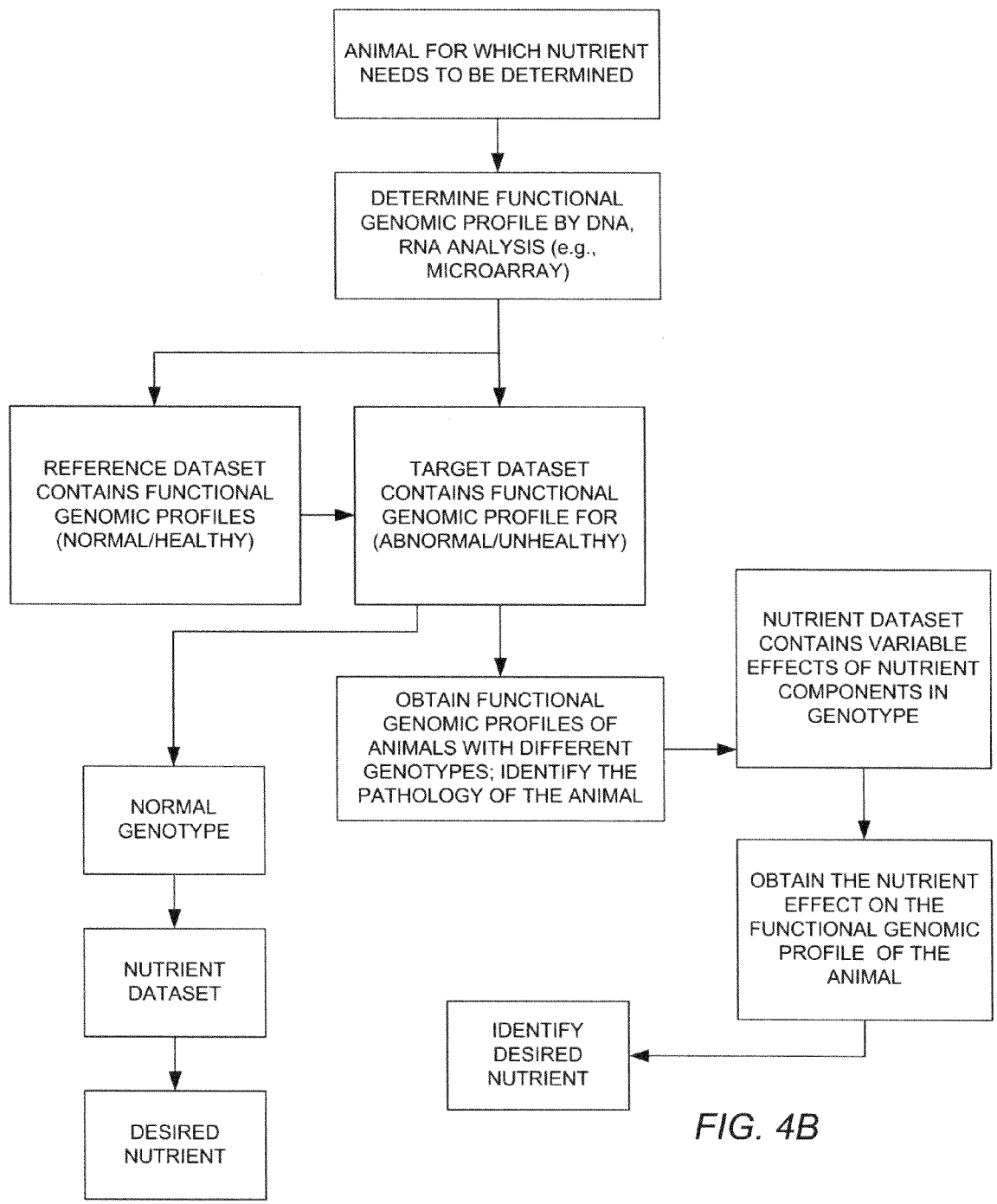

FIGS. 4A and 4B are flowcharts showing the method for designing a nutritional formula. For example, the genotype of the test animal is analyzed using a DNA microarray with 40,000 SNPs and the functional genomic profile is analyzed using a RNA microarray with 40000 probes of 60mer. The functional genomic profile is compared with a reference dataset, containing functional genomic profile for normal healthy animals having different genotypes. When the comparison is a match, a regular diet is designed by considering the genotype of the normal healthy animal. When there is no match with any of the existing functional genomic profile, the functional genomic profile of the test animal is compared with a target data set, containing functional genomic profile for the affected unhealthy animals having different genotypes.

The match of the test animal functional genomic profile with a functional genomic profile of the target dataset permits the identification of the involved pathological state. Selection of the required or recommended dietary ingredients or biologocallly active nutrient is determined by comparing the modification of the functional genomic profile due to the specific pathology identified with the data of the nutrient dataset, containing the functional genomic profile of the nutrient or nutrients for animals having different genotypes. In this respect, the biological response to a nutrient depends upon the genotype of the animal, and a biologocallly active nutrient could, for example, have a positive effect on a first genotype, a mild effect on a second genotype and no effect on a third genotype.

Figure 5A:
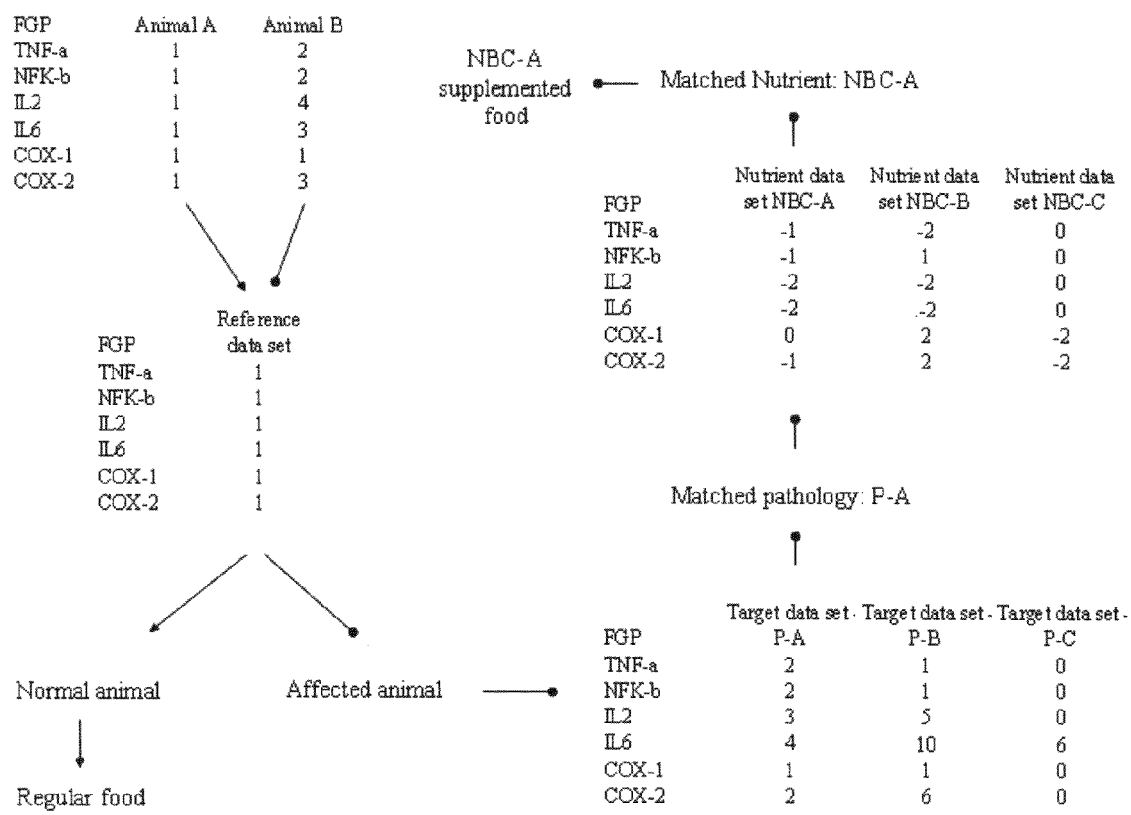

FIGS. 5A, 5B and 5C describe datasets showing the method of dynamic nutrient determination relative to FIG. 4. In the figure, the values of functional genomic profile represent the relative expressions of genes involved in inflammatory process measured with quantitative real time RT-PCR.

In the FIG. 5A, the functional genomic profile of two animals is compared to the functional genomic profile of reference data set. The match of the functional genomic profile with that of reference data set indicates a normal condition (Animal A), and the mismatch an abnormal unhealthy condition (Animal B). The comparison of functional genomic profile of the abnormal unhealthy animal (Animal B) with target data set allows one to identify the type of pathology (Pathology P-A), based on a matched functional genomic profile. The query of the biologocallly active nutrient data set indicates that the appropriated compound is NBC-A, since it has a reverse effect of the expression values of target genes. Compound NBC-A is used to supplement the diet of the animal (Animal A) to restore the animal's physiological homeostasis.

In the FIG. 5B, the functional genomic profile of two animals of different genotype but the same pathology is reported in the reference data set. The functional genomic profile for the same pathology differs between dogs and the relative values are reported in the target data set. Similarly to FIG. 5A, the match of functional genomic profile of the animals with the functional genomic profile of the target data set indicates the presence of the pathology. Searching the biologocallly active nutrient data set for a biologically active nutrient with an functional genomic profile able to counteract the pathology, it was determined that genotype A requires biologically active nutrient A and genotype B requires biologically active nutrient B to treat the same pathology. In the example, a different effect of biologically active nutrient A and biologically active nutrient B on animals with genotype A and B is shown.

In the FIG. 5C, the functional genomic profile of two animals of different genotype but the same pathology is reported in the reference dataset. The reference dataset contains the functional genomic profile of normal healthy animals with different genotypes (symbols). In the example, the functional genomic profile is considered based on four genes (G1, G2, G3 and G4). The functional genomic profile of two test animals of known genotypes (square and triangle) is compared with the functional genomic profile of reference and target datasets and the comparison indicates the presence of a pathological condition. For the square genotype, G3 was 1 instead of 2 and for triangle genotype G4 was 2 instead of 1.

The selection of the biologically active nutrient is based on the library of the functional genomic profile contained in the nutrient dataset. In the example, three compounds or constituents are reported, namely CA, CB and CC, with the relative functional genomic profile for the two genotypes (squares and triangles). As can be seen, the compounds vary between them and have a different effect on each of the two genotypes. For the square genotypes, the appropriated biologocalily active nutrient is CB, since it is able to increase the value of G3 by 1 unit, thereby restoring the value of 2 of the normal healthy animals. For triangle genotypes, the appropriate biologocallly active nutrient is CC, since it is able to reduce the value of G4 by 1 unit, thereby restoring the value of 1 of the normal healthy animals.

Figure 6A:
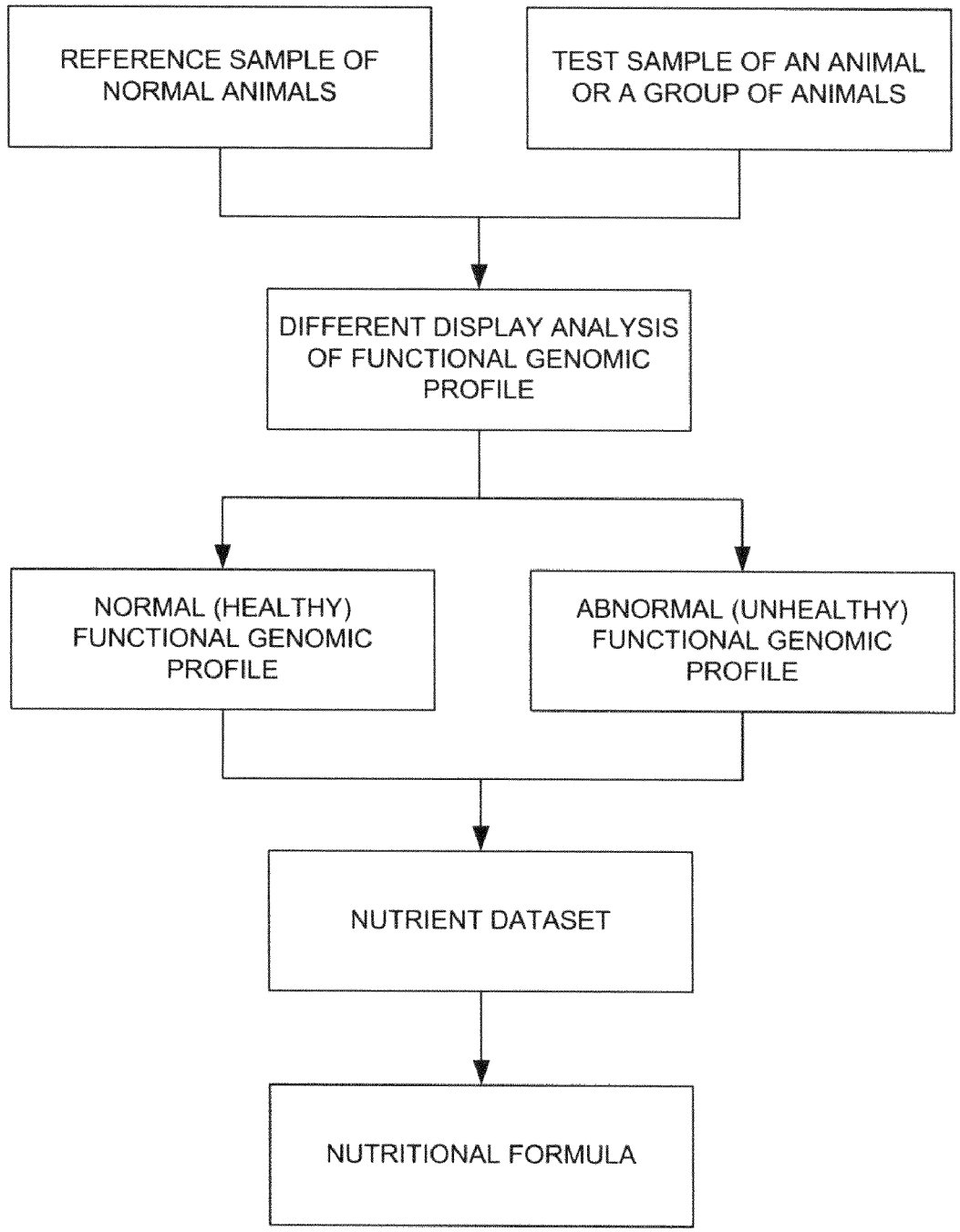
FIGS. 6A and 6B describe flow diagrams showing the method of dynamic nutrient determination using biological samples.
Figure 6B:
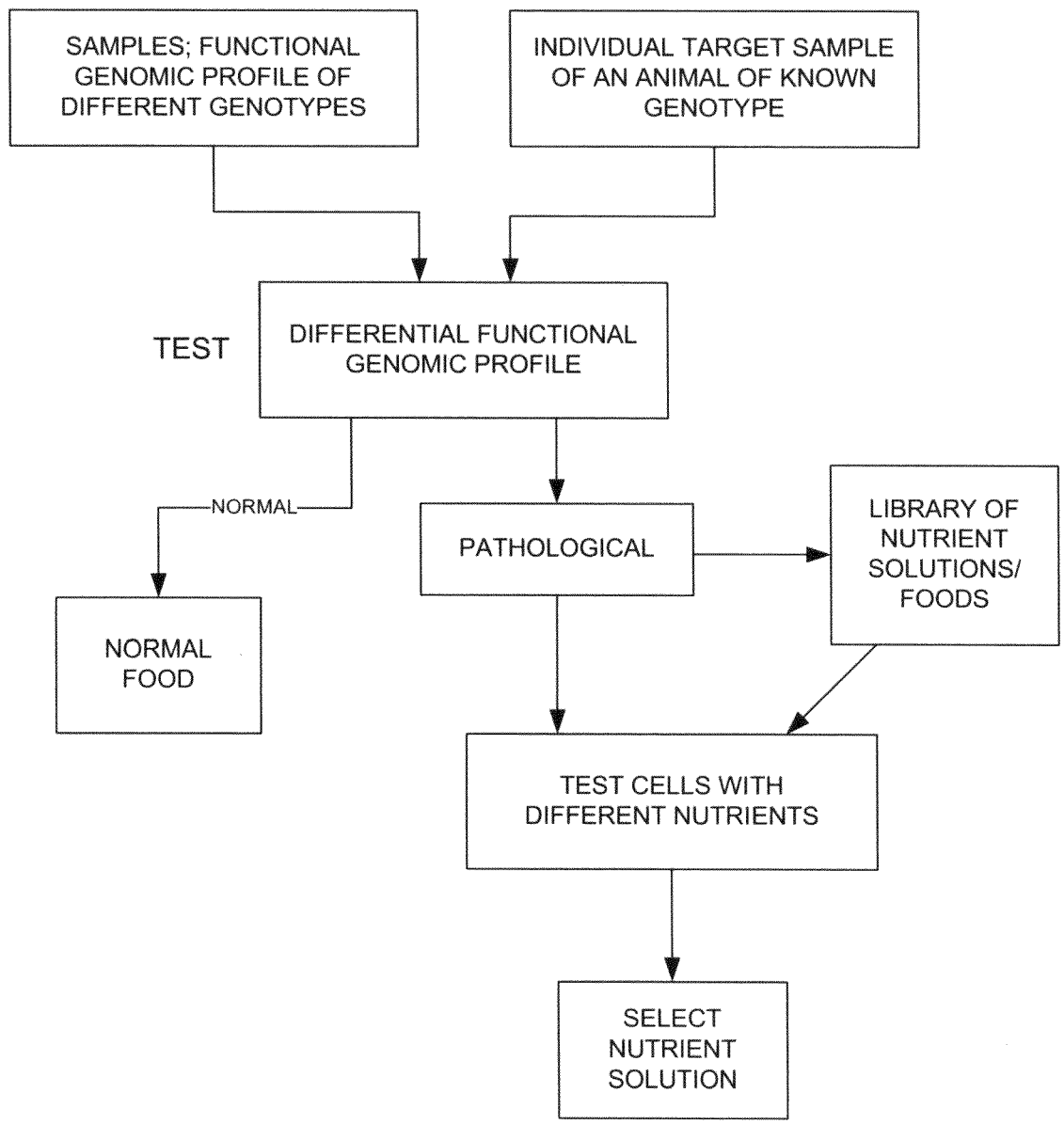

FIGS. 6A and 6B describe flow diagrams showing the method of dynamic nutrient determination using biological samples.

Figure 7:
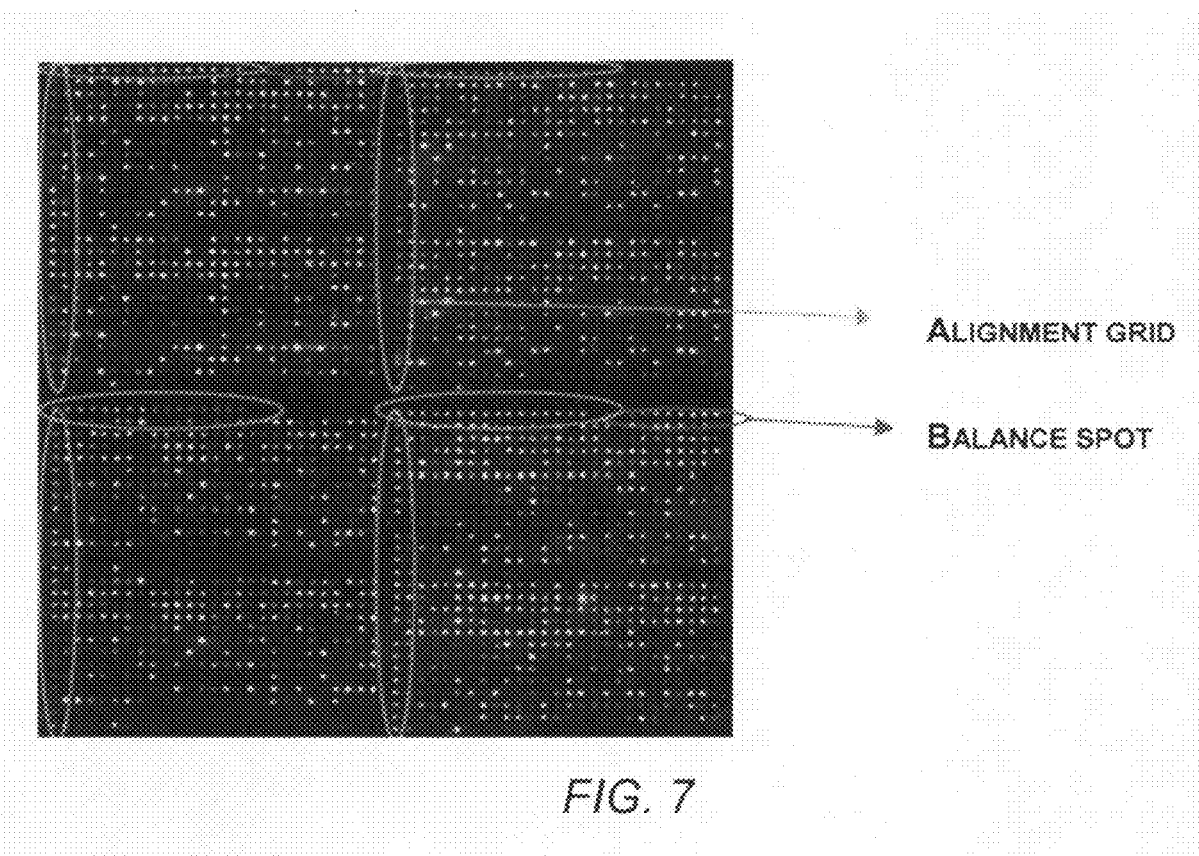
FIG. 7 describes a microarray hybridised with mRNA obtained from blood of a test animal, labelled with Cy3 dye (green), and a pool of mRNA of a pool of healthy animals of the same genotype, labelled with Cy5 dye (red).

FIG. 7 shows a microarray hybridised with mRNA obtained from blood of a test animal, labelled with Cy3 dye (green), and a pool of mRNA of a pool of healthy animals of the same genotype, labelled with Cy5 dye (red).

In the example, a direct comparison between the test animal and the normal healthy animals of the same genotype is performed by means of competitive hybridisation of mRNA on a microarray plafform. A library of pools of mRNA from blood or other biological fluid or tissue of healthy animals of different genotypes is stored and used to assess results obtained for a test animal of known genotype. The pool of mRNA from the blood plasma is selected that has the same genotype as the test animal and labelled with Cy3 dye (green).

The mRNA extracted from the whole blood is labelled with Cy5 dye (red) and the two labelled mRNAs are hybridised on a microarray containing 40,000 spots of probes of 60mer. After scanning and data processing the differential functional genomic profile of the test animal is compared to that of the pool of normal healthy animals. The colour of each spot varies from green to red. A green spot indicates the overexpression of test animal's profile compared to the results of the normal healthy pool. A red spot indicates under-expression of the test animal's profile as compared to results of the normal healthy pool. A yellow spot indicates no variations at the gene expression level of the spot. If the spot is yellow, the test animal is considered to be normal and healthy. If the spot is green or red, the test animal is considered to be affected and unhealthy. After having recorded all the spots and assigned each of them a numeric value according to the intensity of the colour of each spot, the relative value of expression of all the genes of the microarray are used for data mining, by means of bioinformatic tools (http://www.geneontology.org/; http://www.genome.ad.jp/kegg/ http://babelomics.bioinfo.cipf.es/index.html; http://david.abcc.ncifcrf.gov/) for gene functional annotation.

The process enables one to identify a set of genes and gene associated functions which are different or identical to those of normal healthy animals. This permits the diagnosis of the condition of the test animal. In the case that the functional genomic profile indicates a pathological condition in the test animal, the identification of the appropriated biologically active nutrient is achieved by using the cells (i.e. leukocytes) of the test animal in an in vitro assay.

Based on the identified pathology, a set of potential biologically active nutrients is selected from a library of nutrients of already known specific activity for this particular pathological state. These biologically active nutrients are incubated together with the cells of the test animals, the mRNA is extracted and the expressed functional genomic profile is measured with a custom array using real time RT-PCR. The custom array is designed to contain the over-or under-expressed genes of the test animal as compared to those of the pool of the normal healthy animals. The biologically active nutrient is thus selected according to its specific effect on the test animal for that particular pathological condition.

Figure 8:
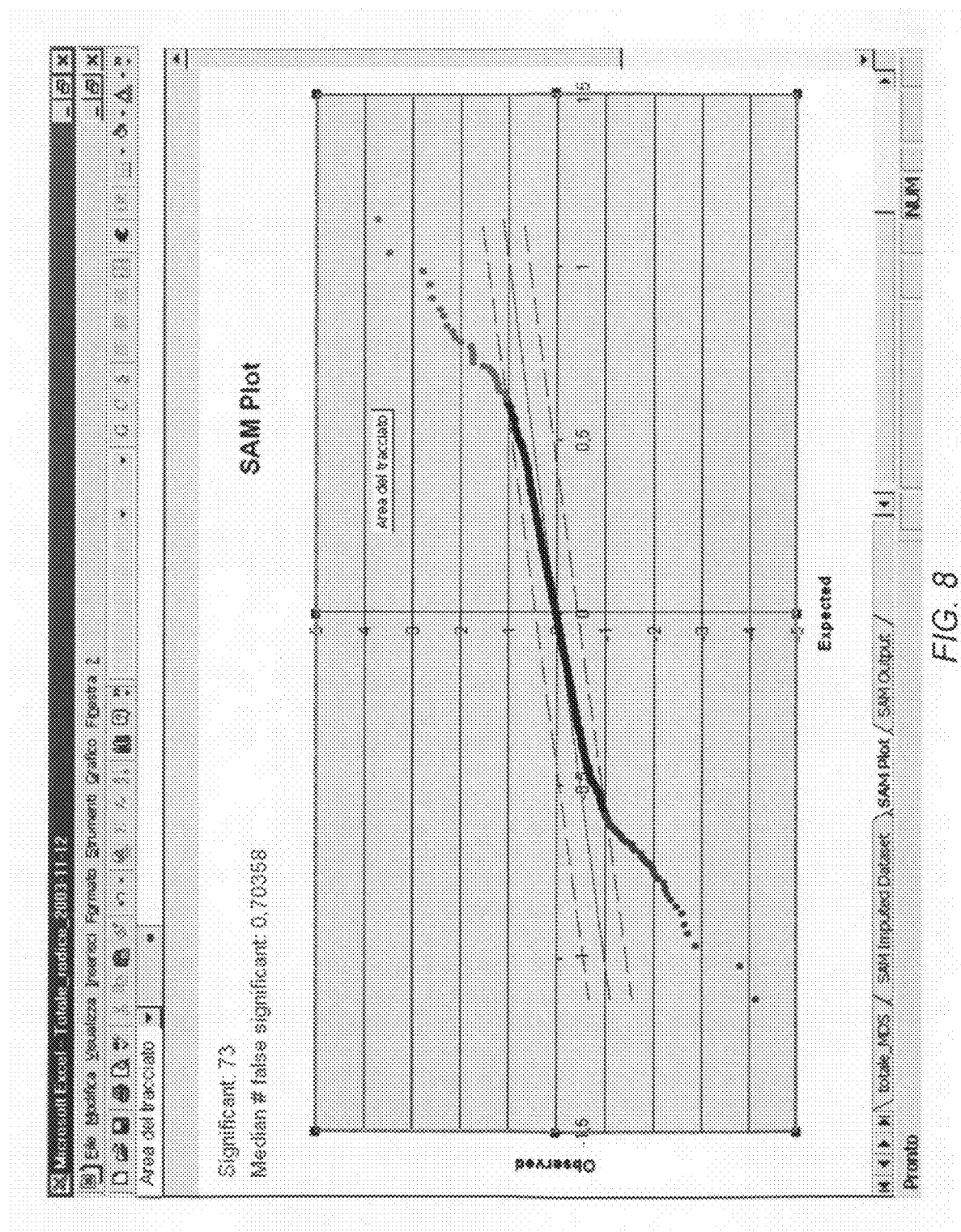
FIG. 8 shows the affect of image acquisition and a data processing system of the microarray. Spots are scanned, and the intensity of the colour converted in digits and then processed with SAM (statistical analysis of microarray) software, and this is illustrated graphically.
Figure 10:
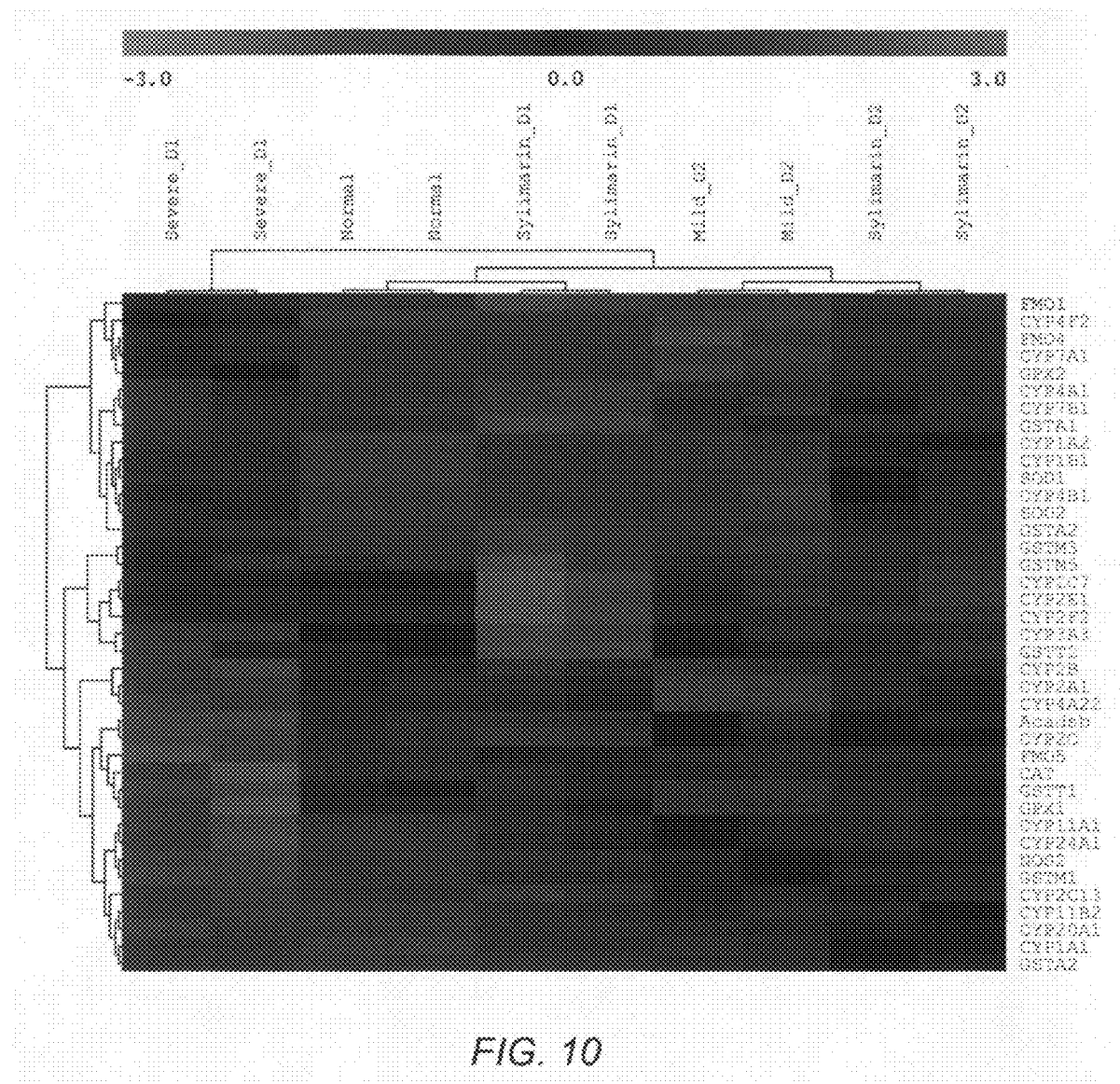
FIG. 10 is a heat map. The heat map shows the expression levels of the genes encoding for individual normal, healthy dogs of genotype D1 or D2, and unhealthy individual dogs severely (D1) and mildly (D2) affected with liver disease before and after sylimarin administration for 15 days. Gene expression values were normalised for the mean value of the row. Gene expression levels range from negative (green) to positive (red) and the graded intensity of the values are indicated by the line (from −3 to +3).
Figure 11:
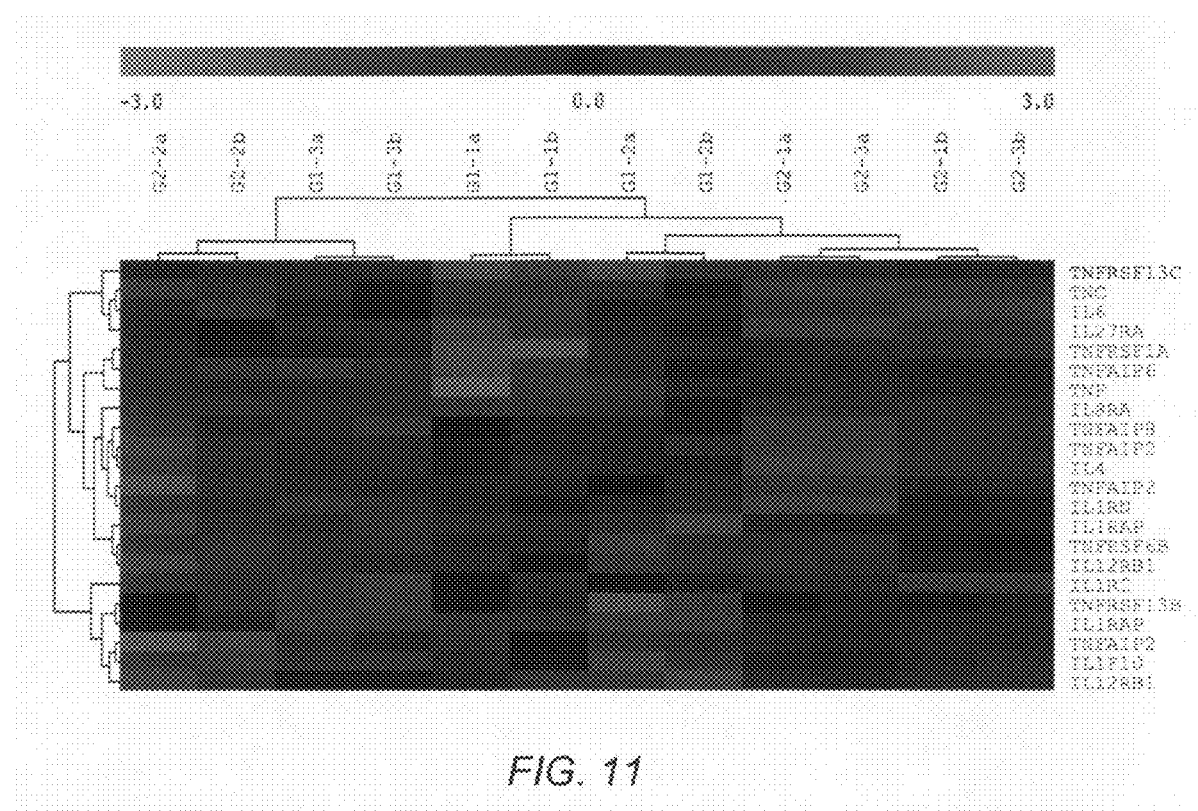
FIG. 11 is a heat map The heat map shows the expression levels of the genes encoding for individual normal healthy Sardinian (G1-1a; G1-1b) and Bergamasca (G2-1a; G2-1b) sheep, individual affected unhealthy Sardinian (G1-2a; G1-2b) and Bergamasca (G2-2a; G2-2b) sheep, and after individual treatments with *Echinacea angustifolia* of Sardinian (G1-3a; G1-3b) and Bergamasca (G2-3a; G2-3b) sheep. Gene expression values were normalised for the mean value of the row. Gene expression levels range from negative (green) to positive (red) and the graded intensity of the values are indicated by the line (from −3 to +3).
Figure 12:
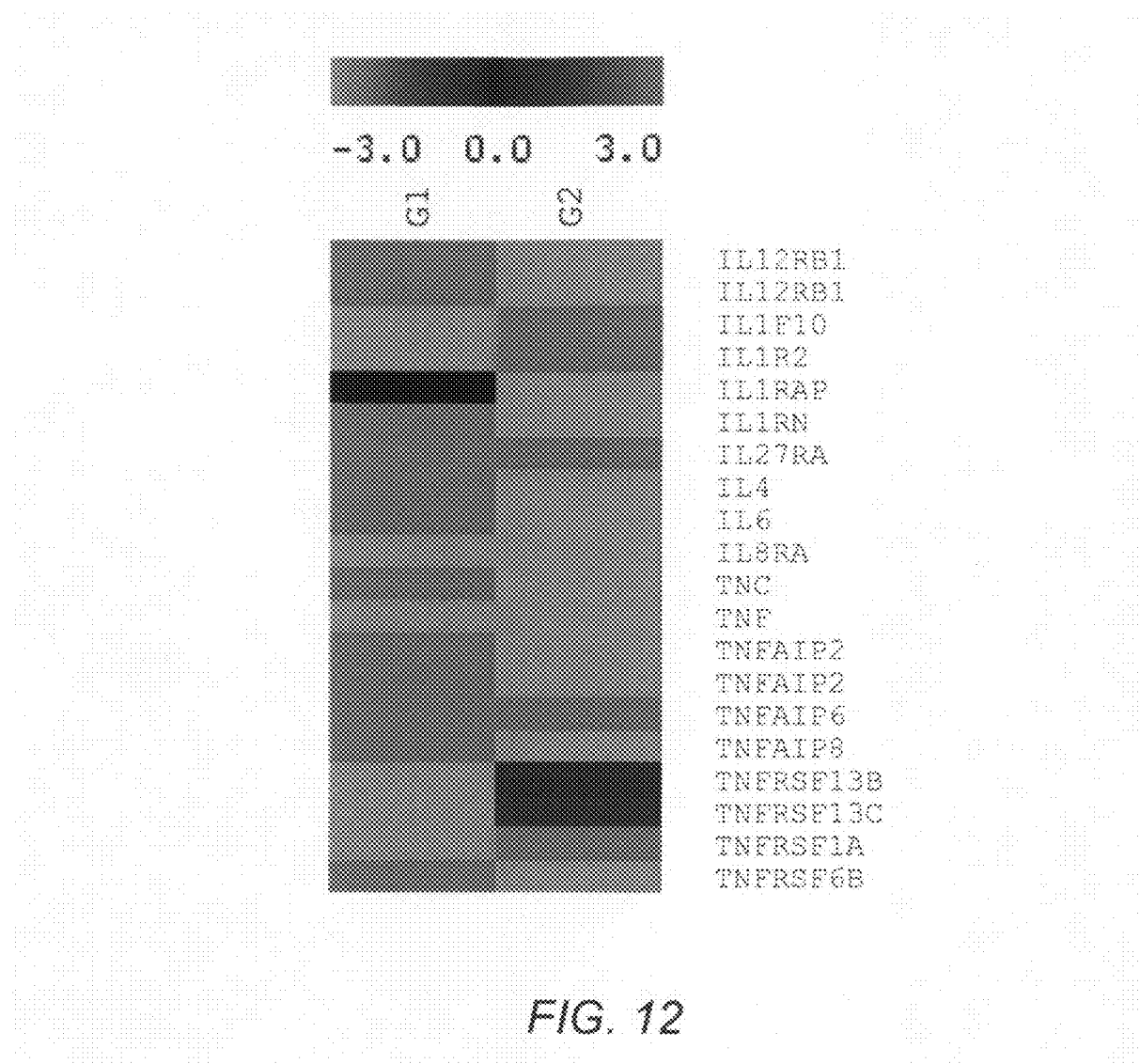
FIG. 12 is a heat map. The heat map shows the different molecular dietary signatures of *Echinacea angustifolia* on individual sheep of two different genotypes (G1 Sardinian; G2 Bergamasca).
Figure 13:
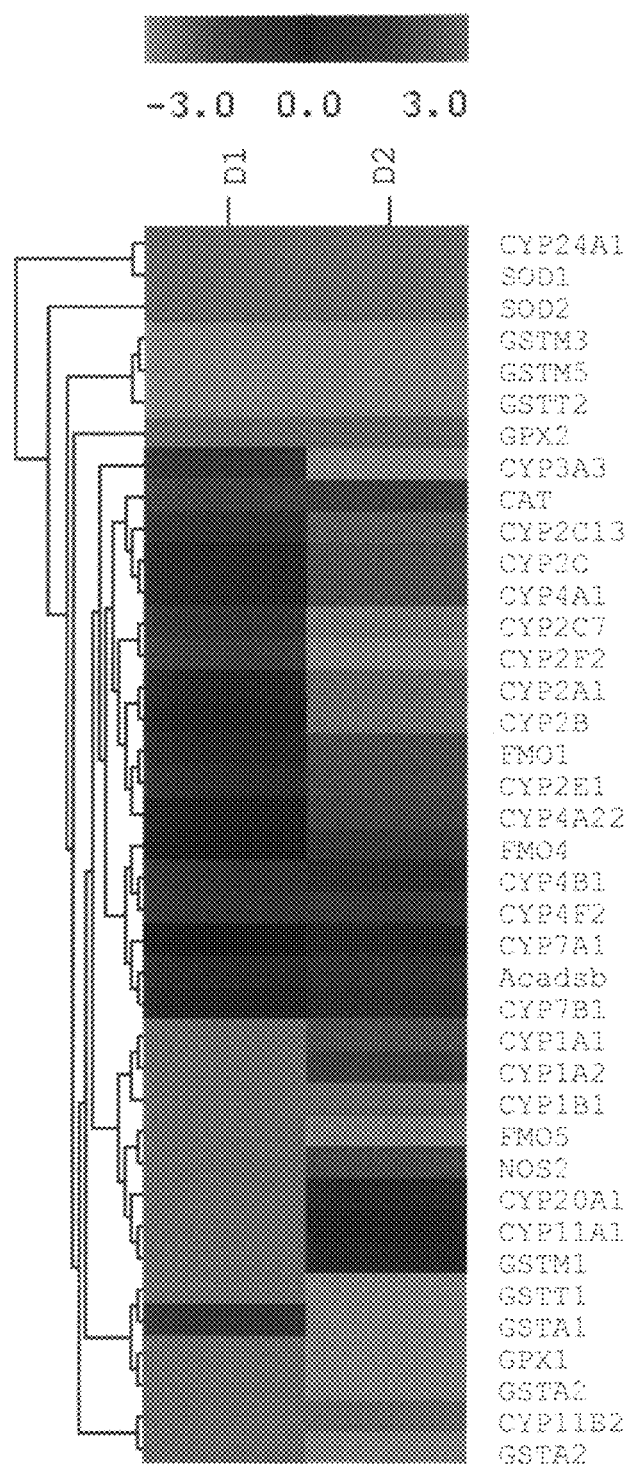
FIG. 13 is a heat map. The heat map shows the different molecular dietary signatures of sylimarin in individual dogs of two different genotypes (D1 or D2).

FIG. 8 shows the data processing system of the microarray. Spots are scanned, intensity of the colour is converted into numerical value digits and then is processed with SAM (statistical analysis of microarray) software. The plot of spos (genes) intensity of red and yellow colours leads to the identification of the genes that significantly differ from the straight line. An arbitrary value of the ratio is taken as threshold for the up (higher than 1.5) or down (lower than −1.5) regulated genes.

The system accesses biological samples by the method of dynamic nutrient determination, wherein the functional genomic profile of a reference data set pool of a biological sample for each genotype of the animals in physiological homeostasis is compared with the functional genomic profile of a test animal of a defined genotype. Mismatching indicates an abnormal unhealthy animal, which can be diagnosed according a library of functional genomic profiles from a pool of data obtained for animals with the same genotype and pathology. The mismatching requires a change of food.

FIG. 9, illustrates, respectively, two typical molecular dietary signatures of two different nutrients, namely, Curcumin and Andrographolide on a set of genes for animals with the same genotype.

The molecular dietary signature of the animal is the variation of a set of genes which differ for each animal genotype or phenotype or nutrient.

The protein signature is the variation of a set of metabolites which differs for each animal genotype or phenotype or nutrient.

The metabolic signature is the variation of a set of protein which differs for each animal genotype or phenotype or nutrient.

Generally, the phenotype is the genetic nature of an organism that is revealed by visible characteristics or measurable performance, in contradistinction to the genotype, which may not be evident without a breeding test or genetic map.

The term "phenotype" as used herein refers to the appearance of an individual resulting from the interaction of environmental factor with the genotype of the individual. "Phenotypic information" is the physical descriptive and health assessment profiles and characteristics such as the physiological, pathological, endocrinological, hematological, epidemiological, behavioral, and immunological data from parameters such as phenotype, breed, lifespan, health history, and presence of infectious diseases and metabolic disorders.

The term "genotype" refers to the genetic information carried both in chromosomes and extrachromosomally.

The "genotypic information" relates to genetic mapping, genetic background, and genetic screening databases. This includes data obtained from the pedigree, family history, heritable physical characteristics, genetic screening tests, DNA testing, genomic mapping, and related laboratory assessment of the gene product for known or suspected congenital and heritable traits. In this application, the term "gene product" means the specific phenotypic characteristic(s) resulting from the expression of the genotype, and may include certain specific laboratory or other test data.

The "genotypic information" typically relates to individual animals, or a group or class of animals. This genotypic information, namely the physical characteristics and genetic makeup (pedigree), heritable disorder history, and related health history of animals in the group is usually manually recorded by breeders, owners, and researchers of companion and other valued animals. The genetic constitution of an individual includes genes without visible effects as well as those revealed by the phenotype. It may refer to all the genes or to a single pair of alleles.

"Genotyping" refers to the process of determining the genotype of an individual by the use of biological assay, such as polymerase chain reaction (PCR), DNA sequencing, and DNA microarrays. The technique provides a measurement of the genetic variation between members of a species and is uses to investigate disease, productive, reproductive and nutrition-associated genes. The most common type of genetic variation is the single nucleotide polymorphisms (SNP) that is a single base pair mutation at a specific locus, usually consisting of two alleles. SNPs are often found to be associated with many diseases, productive and reproductive traits of animals and are becoming of particular interest in pharmacogenetic, pharmacogenomic, nutrigenetic and nutrigenomic studies.

A group of animals of the same specie having the same genotype includes individuals that share a minimum number of common SNPs or other DNA markers that are related to a defined characteristic. In that sense, one animal can be included in several genotype groups, according to the specific characteristic to which that the group relates.

In humans, the use of SNPs is being extended to the haplotype (HapMap project), which is attempting to provide the minimal set of SNPs needed to genotype the human genome. Similar haplotyping is being extended to animals.

SNPs can also provide a genetic fingerprint for use in identity testing.

The "group" can be defined at least in part by a physiological condition that is a product of interaction of the genotype with the environment of an animal or a group of animals. The term "physiological condition" refers to one or more of the physical, behavioral and biochemical attributes of an animal including its size, weight, age, sex, activity level, disposition, and condition of heath or disease.

"Functional Genomic Profile" as used in this disclosure includes DNA regions transcribed into RNA, expressed genes, expressed sequence tag (EST), micro RNA, translated proteins and their derived metabolites. A functional genomic profile can be established using any one or more of a genomic, proteomic or metabolomic approach. A functional genbmic profile can result from information from DNA, RNAs, peptides, proteins, or metabolites associated with a phenotypic condition of an animal in response to exposure to one or more biologically active nutrients.

Information for the Functional genomic profile as used in this disclosure is generated from biological samples by any technique known in the art of functional genomics. Examples of techniques useful in generating functional genomic analysis include, without limitation, the following techniques that can be used individually or in combination: (a) DNA, cDNA, RNAs and protein arrays and microarrays in the existing low and high density formats; (b) polymerase chain reaction (PCR) techniques including single and multiplexed quantitative real-time PCR techniques; (c) serial analysis of gene expression (SAGE); (d) DNA and RNA sequencing; (e) Southern blot analysis, Northern blot analysis and Western blot analysis; (f) gel electrophoresis, including two-color 2D gel methodologies, SDS-polyacrylamide gel electrophoresis (SDS-PAGE), and 2D PAGE; (g) protein sequencing, using variable existing mass spectrometry techniques; (h) metabolite analysis, using variable existing mass spectrometry techniques; (i) liquid chromatography by itself or in tandem with mass spectrometry techniques and other separative analytical techniques.

As used in this disclosure, the functional genomic profile extends beyond measurements of clinical pathology analytes such as complete blood count, serum chemistry, hormone assays and analysis.

The functional genomic profile of an animal can be associated with a "normal" or "abnormal" phenotype. A "normal" phenotype is one occurring in an animal exhibiting a condition of health as defined herein, and generally indicative of such a state. A "normal" phenotype is associated with physiological homeostasis, i.e., a tendency to stability of optimal bodily functions. An "abnormal" phenotype is one that is outside the range identified as "normal" and can be associated with a breakdown in physiological homeostasis or pathophysiological condition.

A functional genomic profile from a normal phenotype differs at least in one piece of data or information from the functional genomic profile of an abnormal phenotype. A progressive drift from normality can lead to the death of the individual, requiring an intervention to restore the physiological homeostasis to a healthy, normal condition.

A normal phenotype can present a functional genomic profile generally associated with an abnormal phenotype, indicating a latent non-physiological homeostasis or hereditary predisposition. This drift from the normality requires a preventive or prophylactic intervention to restore the physiological homeostasis to abnormal healthy condition.

"Biological samples" include for instance feces and urine, blood, lymph, tears, cheek swab, saliva, amniotic fluid, serum, prostatic and vaginal secretions, hair, tissue biopsies and necropsy specimens.

The "reference dataset" includes the functional genomic profile of biological samples and genotype information for the animals with normal phenotype, typically stored in digital form and organized in one to a plurality of databases.

The "target group dataset" contains the functional genomic profile of biological samples and genotype information for the animals in abnormal unhealthy conditions.

The "nutrient dataset" comprises genotype information and the different effects of biologocallly active nutrients on a functional genomic profile of animal of different genotypes.

The different genotypes respond differently to the same nutritional components, and according to the present disclosure, effects of biologocalily active nutrients on the functional genomic profile can be determined by controlled experiments in animals having different genotypes and exposed to different levels of, and/or different durations of exposure to, one or more biologocailly active nutrients.

In one embodiment, an alternative testing model of biologocalily active nutrients is an ex vivo model using tissue explants obtained from an animal of the same species and the same genotypes, and maintained outside the body of the animal.

The nutrition data set can include data not only on chemical or biological entities known as biologocallly active nutrients but on a variety of materials that have nutritional, or nutriceutical or pharmacological effect. All such materials are considered biologocallly active nutrients herein if a useful effect on expression of at least one gene, function of at least one protein or production of at least one metabolite is found. In one embodiment, biologocallly active nutrients of interest herein are materials having GRAS (generally regarded as safe) or equivalent status under U.S. FDA (Food and Drug Administration) regulations or counterpart regulations in other countries, or are eligible for such status. In other embodiments a biologocallly active nutrient can be a therapeutically or pharmacologically effective compound, e.g. a drug or herbal medicine.

Otherwise, the macronutrients required in a balanced animal diet (protein, carbohydrate, fat and fiber) are considered separately from biologocallly active nutrients such as those listed above in designing a nutritional formula, as will be discussed below.

Certain biological materials, especially botanical materials, can be considered biologocallly active nutrients and can, if desired, be included in the nutrition data set. In many of these, a bioactive chemical entity has been identified. Even where a bioactive component is known, other unknown, bioactive components may be present and contribute to the bioactive effect or effects of the biological material.

Examples of macronutrients are set out:
Macro-Nutrients
Chicken meat
Beef meat
Lamb meat
Horse meat
Turkey meat
Bison meat
Ostrich or Enu meat
Rabbit meat
Venison meat
Fish,
Egg
Rice
Carrot
Pumpkin
Peas
Beet, sugar pulp
Soy hulls
Potato
Oats
Oil, vegetable Examples of micronutrients and biologocallly active nutrients are set out:
Micro-Nutrients and Biologically Active Nutrients
Leucine
Isoleucine
Valine
Alanine
Glutamine
Taurine
L-Carnitine
*Portulaca oleracea*
*Andrographis paniculata*
*Butea frondosa*
*Sylibum marianum*
*Echinacea angustifolia*
*Curcuma longa*
*Eleutherococcus senticosus*
*Valeriana officinalis*
*Matricaria recutrita*
Conjugated linoleic acid
Na sulphate
Glucosamine HCl
*Vaccinum nirillus*
Vitamin E
Vitamin C
Vitamin B1
Vitamin B2
Di-methylglycine
g-orizanol
EPA+DHA
Green tea polyphenols Data defines the genotype and physiological condition of the individual animal for which a diet is designed, and a nutrition product or composition prepared. This includes the functional genomic profile. In order to design the nutritional formula, the input data for an animal is compared with reference data set and target data set to identify the normal or abnormal unhealthy conditions of the individual animal.

The nutrient data set contains the effects of biologocalily active nutrients on the functional genomic profile of an individual animal with different genotypes. The nutritional formula is computed to incorporate effective amounts of one or more biologocalily active nutrients according to the specific effects on the functional genomic profile in order to restore the physiological homeostasis. The nutritional formula can be computed as a dietary or nutritional supplement which can be related to, exclude, or include basic energy, protein, metabolic or other nutrient requirements.

Where a nutritional formula, food or composition is generated, the biolologically active nutrients and other components can be in any suitable form. For example, components can be expressed in terms of their content in a food composition (e.g., in % or in mg/g, usually on a dry matter basis), in terms of a daily dosage or allowance (e.g., in g/day), or optionally on a live weight basis (e.g., in mg/kg/day). An illustrative nutritional formula, food or nutrient composition can be obtained by the present disclosure and can for instance include any one or more of the exemplary macro-nutrients, micro-nutrients and/or additives set out above. The food composition could be one or more biologically active nutrient formulas selected from the exemplary macro-nutrients, micro-nutrient and/or additives setout above and self contained and/or added as a "sprinkle" supplement in a dry. liquid or semi-moist form to an existing regular or specialized or therapeutic diet.

Animals in conditions of health or disease are identified. Each sample is subjected to functional genomic analysis, for example using an established microarray technique, to evaluate an functional genomic profile for the animal that provided the sample, which reflects the genotype, and physiological, and pathophysiological or other condition of the animal at the time the sample was collected.

Biologically active nutrients are tested in one or more animal having different genotypes.

An end-product of one form of the disclosure is the nutritional formula, food or composition. A nutritional formula can be designed to provide a therapy for a state of disease or physiological disorder. The pet food can be manufactured to be customized to an individual animal providing the input data, or to an animal population represented by an animal providing the input data. The manufacture can be individually prepared in a manual form or automatically composed by an automated or computerized system.

The formulas, food or food composition is designed in a dynamic manner for individual animals so as to promote health. This can further include (1) restoring one or more constituents of the functional genomic profile to a healthy condition, including expression of a gene, function of a protein or production of a metabolite; (2) adapting or altering the nutritional management of an animal for specific stressful life stages, even where no disease or disorder is present or detectable, and (3) improving the health in offspring of the individual animal by promoting the health of an individual parent.

EXAMPLES

The disclosure can be further illustrated by the following examples.

Example 1

The example reports the method to build the reference data set, the target data set and the nutrient data set. In the example, the effect of sylimarin to treat liver disease of dogs with different genotypes is reported.

Construction of the Reference Data Set

Twenty normal, healthy dogs (with genotypes D1 or D2) was used to build the reference data set. Blood was sampled and total DNA and RNA extracted. DNA was used for genotyping and haplotype identification, using restriction fragment length polymorphism (RFLP) and gel electrophoresis, including nine known single polymorphisms (SNPs) along chromosome CF15. RNA was used for the determination of gene expressions, by means of a pathway specific microarray. The technique is based on the quantitative real time RT-PCR.

The functional genomic profile of a population of 20 mixed breed dogs, from 2 to 4 years old, in healthy clinical condition and considered normal, was measured using a pathway-specific microarray. The pathway for drug metabolizing enzymes was used, and included the genes reported in the table below.

| Gene symbol | Gene name |
|---|---|
| Acadsb | acyl-coenzyme A dehydrogenase, short/branched chain |
| CAT | catalase |
| CYP11A1 | cytochrome P450, family 11, subfamily A, polypeptide 1 |
| CYP11B2 | cytochrome P450, family 11, subfamily B, polypeptide 2 |
| CYP1A1 | cytochrome P450, family 1, subfamily A, polypeptide 1 |
| CYP1A2 | cytochrome P450, family 1, subfamily A, polypeptide 2 |
| CYP1B1 | cytochrome P450, family 1, subfamily B, polypeptide 1 |
| CYP20A1 | cytochrome P450, family 20, subfamily A, polypeptide 1 |
| CYP24A1 | cytochrome P450, family 24, subfamily A, polypeptide 1 |
| FMO1 | flavin containing monooxygenase 1 |
| FMO4 | flavin containing monooxygenase 4 |
| FMO5 | flavin containing monooxygenase 5 |
| NOS2 | nitric oxide synthase 2A |
| CYP2A1 | cytochrome P450, family 2, subfamily A |
| CYP2B | cytochrome P450, family 2, subfamily B |
| CYP2C | cytochrome P450, family 2, subfamily C |
| CYP2C13 | cytochrome P450, family 2, subfamily C, polypeptide 13 |
| CYP2C7 | cytochrome P450, family 2, subfamily C, polypeptide 7 |
| CYP2E1 | cytochrome P450, family 2, subfamily E, polypeptide 1 |
| CYP2F2 | cytochrome P450, family 2, subfamily F, polypeptide 2 |
| CYP3A3 | cytochrome P450, family 3, subfamily A3 |
| CYP4A1 | cytochrome P450, family 4, subfamily A, polypeptide 1 |
| CYP4A22 | cytochrome P450, family 4, subfamily A, polypeptide 22 |
| CYP4B1 | cytochrome P450, family 4, subfamily B, polypeptide 1 |
| CYP4F2 | cytochrome P450, family 4, subfamily F, polypeptide 2 |
| CYP7A1 | cytochrome P450, family 7, subfamily A, polypeptide 1 |
| CYP7B1 | cytochrome P450, family 7, subfamily B, polypeptide 1 |
| GSTM1 | glutathione S-transferase M1 |
| GSTM3 | glutathione S-transferase M3 |
| GSTM5 | glutathione S-transferase M5 |
| GSTT1 | glutathione S-transferase theta 1 |
| GSTT2 | glutathione S-transferase theta 2 |
| SOD1 | Superoxidodismutase 1 |
| SOD2 | Superoxidodismutase 2 |
| GPX1 | Glutathione peroxidase 1 |
| GPX2 | Glutathione peroxidase 2 |
| GSTA1 | glutathione S-transferase A1 |
| GSTA2 | glutathione S-transferase A2 |
| GSTA2 | glutathione S-transferase A4 |

No differences in the gene expression levels for this panel of genes were observed between the five haplotypes (A to E).

Values for gene expression of individual normal healthy dogs are part of the functional genomic profile of the reference data set, in this case being identical for dogs of genotypes D1 or D2. The functional genomic profile is the molecular dietary signature of normal, healthy dogs.

Construction of the Target Data Set

A second population of 30 dogs suffering liver diseases was screened for haplotypes. Blood was sampled and total DNA and RNA extracted. DNA was used for genotyping and haplotype identification and RNA for the determination of gene expressions, using the pathway specific microarray.

The expression profile of the dogs was clustered in two patterns, according to the severity of clinical symptoms, a so called Severe (D1, 18 dogs) and Mild (D2, 12 dogs), functional genomic profile of the two population differed, severely affected dogs (D1) showing an higher increase of detoxifying and antioxidant enzymes than the mildly affected dogs (D2).

The functional genomic profile in the target data set of the two defined genotypes is the molecular signature of liver disease for the dogs of genotypes D1 or D2.

Values for gene expression of individual unhealthy dogs severely and mildly affected with liver disease are part of the functional genomic profile of the target data set, in this case being different for genotypes D1 or D2.

The number of known haplotypes was 5 (from A to E, shown below), and an association is shown between those dogs with haplotypes including the causal variant of SNP "A" and "B" and the severity of liver diseases.

| | SNP profiling pattern of dogs | | | | | | | | |
|---|---|---|---|---|---|---|---|---|---|
| HAPLOTYPE | A | B | C | D | C | E | A | G | E | SNP Variant Response |
| 1 | A | C | T | T | T | C | A | C | C | Severe Illness |
| 2 | A | C | T | T | T | C | A | A | C | Severe Illness |
| 3 | T | G | T | A | T | C | G | C | C | Mild Illness |
| 4 | T | G | T | T | T | C | G | C | C | Mild Illness |
| 5 | A | C | A | T | A | G | A | C | G | Severe Illness |
| 6 | A | C | A | A | A | G | A | C | G | Severe Illness |
| | Causal variant | Causal variant | | | | | Causal variant | | |

Construction of the Nutrient Data Set

The two genotyped populations of 18 (D1) and 12 (D2) unhealthy dogs (30 overall) suffering from liver disease were fed orally with a standardized extract of *Sylibum marianum*, a dose of 1.5 mg/kg body weight of sylimarin for 15 days. At the end of the treatment, blood was collected from each of the individual animals of the severe (D1) and mild (D2) illness groups and their total RNA was extracted. The RNA of individuals animals of the severe and mild illness groups were analysed for gene expressions in duplicate using the pathway-specific microarray.

The gene expression profiles of individuals from these two populations of unhealthy dogs after 15 days of sylimarin treatment (severe D1 and mild D2) showed a different pattern.

The nutrient data set contains the molecular dietary signature of the sylimarin for individual dogs of genotypes D1 or D2. In the example, sylimarin supplementation can be used to effectively treat affected unhealthy dogs of the D1 genotype but not affected unhealthy dogs of the D2 genotype.

Expression levels of the genes encoding for individual normal healthy dogs of genotypes D1 or D2, and individual unhealthy dogs, severely (D1) and mildly (D2) affected with liver disease before and after sylimarin administration (Sylimarin D1 and Sylimarin D2) for 15 days.

| | GENE EXPRESSION LEVELS | | | | | | | | |
|---|---|---|---|---|---|---|---|---|---|
| | Normal | | Severe D1 | | Mild D2 | | Sylimarin D1 | | Sylimarin D2 | |
| | Mean | s.d. | Mean | s.d. | Mean | s.d. | Mean | s.d. | Mean | s.d. |
| Acadsb | 0.9 | 0.1 | 2.3 | 0.3 | 1.0 | 0.1 | 0.8 | 0.2 | 1.1 | 0.3 |
| CAT | 1.4 | 0.4 | 5.0 | 0.9 | 1.7 | 0.2 | 1.7 | 0.3 | 1.8 | 0.2 |
| CYP11A1 | 1.5 | 0.2 | 12.9 | 1.1 | 6.5 | 1.1 | 3.9 | 0.3 | 4.7 | 3.4 |
| CYP11B2 | 2.0 | 0.4 | 24.9 | 2.3 | 16.0 | 3.0 | 7.2 | 0.6 | 10.7 | 2.3 |
| CYP1A1 | 0.3 | 0.1 | 7.7 | 1.1 | 6.3 | 0.9 | 2.1 | 0.3 | 3.9 | 0.9 |
| CYP1A2 | 0.4 | 0.1 | 5.3 | 0.9 | 5.7 | 0.8 | 1.5 | 0.2 | 3.6 | 0.3 |
| CYP1B1 | 1.4 | 0.6 | 12.2 | 0.9 | 15.8 | 1.4 | 3.6 | 1.2 | 10.2 | 0.7 |
| CYP20A1 | 2.4 | 0.6 | 16.8 | 3.4 | 11.3 | 1.5 | 5.1 | 3.4 | 8.1 | 1.0 |
| CYP24A1 | 1.3 | 0.2 | 253.0 | 25.6 | 113.9 | 14.3 | 68.5 | 8.9 | 68.3 | 5.6 |
| FMO1 | 2.3 | 0.4 | 3.4 | 0.8 | 4.5 | 1.1 | 1.5 | 0.3 | 4.0 | 1.3 |
| FMO4 | 2.1 | 0.6 | 3.4 | 1.0 | 11.6 | 2.0 | 1.5 | 0.5 | 8.0 | 0.8 |
| FMO5 | 2.5 | 0.3 | 13.3 | 1.9 | 2.8 | 0.7 | 4.2 | 3.4 | 3.1 | 0.2 |
| NOS2 | 3.0 | 0.9 | 12.4 | 1.9 | 6.9 | 0.9 | 4.1 | 4.0 | 5.8 | 0.3 |
| CYP2A1 | 1.7 | 0.2 | 2.4 | 0.5 | 0.5 | 0.1 | 1.1 | 0.2 | 1.3 | 0.1 |
| CYP2B | 1.9 | 0.2 | 3.0 | 0.4 | 1.3 | 0.4 | 1.3 | 0.3 | 1.9 | 0.2 |
| CYP2C | 1.8 | 0.3 | 3.8 | 0.3 | 2.2 | 0.6 | 1.5 | 0.5 | 2.3 | 0.9 |
| CYP2C13 | 2.4 | 0.6 | 5.8 | 0.9 | 4.1 | 1.0 | 2.2 | 0.8 | 3.9 | 0.6 |
| CYP2C7 | 2.5 | 0.4 | 2.8 | 0.2 | 2.9 | 0.1 | 1.4 | 0.3 | 3.2 | 0.2 |
| CYP2E1 | 1.7 | 0.2 | 1.9 | 0.3 | 2.1 | 0.1 | 1.0 | 0.3 | 2.2 | 0.1 |
| CYP2F2 | 2.8 | 0.3 | 2.8 | 0.3 | 2.5 | 0.5 | 1.5 | 0.5 | 3.1 | 0.4 |
| CYP3A3 | 4.3 | 0.9 | 5.7 | 0.9 | 3.8 | 1.0 | 2.7 | 2.1 | 4.7 | 0.5 |
| CYP4A1 | 2.5 | 0.3 | 4.9 | 1.1 | 4.8 | 0.9 | 2.0 | 2.1 | 4.3 | 0.2 |
| CYP4A22 | 1.1 | 0.1 | 1.7 | 0.4 | 0.2 | 0.1 | 0.8 | 0.3 | 0.8 | 0.1 |
| CYP4B1 | 0.3 | 0.1 | 2.1 | 0.3 | 3.1 | 0.4 | 0.6 | 0.2 | 2.0 | 0.4 |
| CYP4F2 | 0.2 | 0.1 | 2.2 | 0.3 | 4.6 | 0.9 | 0.7 | 0.2 | 2.9 | 0.6 |
| CYP7A1 | 0.8 | 0.2 | 1.4 | 0.3 | 3.8 | 0.1 | 0.6 | 0.1 | 2.7 | 0.2 |
| CYP7B1 | 0.9 | 0.2 | 1.8 | 0.2 | 1.7 | 0.2 | 0.7 | 0.2 | 1.5 | 0.1 |
| GSTM1 | 1.3 | 0.4 | 13.3 | 1.8 | 6.3 | 0.8 | 3.9 | 3.8 | 4.5 | 0.2 |
| GSTM3 | 17.9 | 2.5 | 14.7 | 1.7 | 9.6 | 1.0 | 8.7 | 9.6 | 16.2 | 1.2 |

-continued

| | GENE EXPRESSION LEVELS | | | | | | | | |
|---|---|---|---|---|---|---|---|---|---|
| | Normal | | Severe D1 | | Mild D2 | | Sylimarin D1 | | Sylimarin D2 | |
| | Mean | s.d. | Mean | s.d. | Mean | s.d. | Mean | s.d. | Mean | s.d. |
| GSTM5 | 20.1 | 2.8 | 19.4 | 2.1 | 13.5 | 1.2 | 10.6 | 1.3 | 19.8 | 2.0 |
| GSTT1 | 12.8 | 2.6 | 27.1 | 2.0 | 7.8 | 0.9 | 10.7 | 2.0 | 12.2 | 0.9 |
| GSTT2 | 16.1 | 2.9 | 21.1 | 1.7 | 17.0 | 2.1 | 9.9 | 1.8 | 19.5 | 0.8 |
| SOD1 | 23.9 | 3.8 | 228.2 | 34.7 | 267.7 | 34.5 | 67.4 | 7.0 | 172.5 | 21.3 |
| SOD2 | 16.7 | 1.7 | 115.0 | 14.3 | 164.7 | 28.0 | 35.2 | 3.5 | 107.3 | 14.0 |
| GPX1 | 8.8 | 1.1 | 25.3 | 2.3 | 5.1 | 0.7 | 9.2 | 0.9 | 8.2 | 1.6 |
| GPX2 | 9.5 | 1.2 | 27.3 | 2.1 | 68.7 | 8.6 | 9.9 | 1.0 | 46.0 | 3.9 |
| GSTA1 | 11.8 | 1.9 | 18.8 | 2.0 | 16.8 | 2.3 | 8.2 | 0.5 | 16.8 | 3.0 |
| GSTA2 | 12.4 | 1.5 | 28.0 | 3.1 | 30.8 | 2.1 | 10.9 | 0.9 | 25.4 | 2.7 |
| GSTA2 | 14.1 | 2.0 | 50.2 | 5.6 | 39.7 | 3.4 | 17.2 | 2.1 | 31.8 | 4.5 |

Genotype induces a different response to sylimarin, a micro-nutrient, in dogs with haplotypes including the causal variant of SNP A and B. Sylimarin is one of the main bioactive compounds of the *Sylibum marianum* plant and is known to cleanse the liver and spare liver metabolism.

The heat map shows individual normal dogs of both the D1 or D2 genotypes, having negative (green) values for almost all the genes. Individual unhealthy dogs, severely affected with liver disease (D1) showed positive (red) values, indicating a gene over expression. Administration of sylimarin restored the normal values of the genes, which were clustered together. The pattern of expression of the individual unhealthy dogs mildly affected with liver disease (D2) was different from that of individual dogs severely affected with liver disease (D1), indicating a different state of their liver disease. Sylimarin administration to these individual D2 dogs was neither able to restore the normal condition, nor to change the pattern of gene expression in comparison to the. condition seen in the individual D2 dogs before the treatment. This is apparent from the cluster analysis, since the gene expression of the individual mildly affected dogs before and after sylimarin administration remained clustered together.

Molecular Dietary Signature

Effect of sylimarin administration on individual unhealthy dogs of Genotypes D1 or D2 affected by liver disease Values shown are changes of gene expression.

Molecular Dietary Signature (MDS):

MDS_D1=(Severe_D1-Normal)-Sylimarin_D1

MDS_D2=(Mild_D2-Normal)-Sylimarin_D2

| MEAN CHANGES OF GENE EXPRESSION | | |
|---|---|---|
| GENE | MDS_D1 | MDS_D2 |
| Acadsb | 0.5 | −1.0 |
| CAT | 1.8 | −1.6 |
| CYP11A1 | 7.6 | 0.3 |
| CYP11B2 | 15.7 | 3.4 |
| CYP1A1 | 5.3 | 2.2 |
| CYP1A2 | 3.4 | 1.8 |
| CYP1B1 | 7.2 | 4.3 |
| CYP20A1 | 9.2 | 0.8 |
| CYP24A1 | 183.1 | 44.2 |
| FMO1 | −0.4 | −1.9 |
| FMO4 | −0.1 | 1.5 |
| FMO5 | 6.5 | −2.9 |
| NOS2 | 5.3 | −1.9 |
| CYP2A1 | −0.4 | −2.4 |
| CYP2B | −0.2 | −2.5 |
| CYP2C | 0.5 | −2.0 |
| CYP2C13 | 1.2 | −2.2 |
| CYP2C7 | −1.1 | −2.7 |
| CYP2E1 | −0.7 | −1.9 |
| CYP2F2 | −1.5 | −3.4 |
| CYP3A3 | −1.2 | −5.2 |
| CYP4A1 | 0.4 | −1.9 |
| CYP4A22 | −0.1 | −1.7 |
| CYP4B1 | 1.2 | 0.8 |
| CYP4F2 | 1.3 | 1.5 |
| CYP7A1 | 0.0 | 0.3 |
| CYP7B1 | 0.2 | −0.7 |
| GSTM1 | 8.0 | 0.4 |
| GSTM3 | −12.0 | −24.6 |
| GSTM5 | −11.3 | −26.4 |
| GSTT1 | 3.6 | −17.1 |
| GSTT2 | −4.9 | −18.6 |
| SOD1 | 136.9 | 71.4 |
| SOD2 | 63.1 | 40.7 |
| GPX1 | 7.3 | −12.0 |
| GPX2 | 7.9 | 13.2 |
| GSTA1 | −1.1 | −11.8 |
| GSTA2 | 4.7 | −7.1 |
| GSTA2 | 18.9 | −6.1 |

The heat map shows the molecular dietary signature of sylimarin on genotype D1 and D2.

Comparing the functional genomic profile of a test sample of dog with known genotype with the reference and target dat set The diagnosis of liver disease in a dog can be performed determining the functional genomic profile of a blood sample, using the patter designed microarray.

The DNA of the individual dog needs to be genotyped for the known SNP, enabling to identify the presence of a causal variant of SNP A and B.

The comparison of values for gene expression of the sample of an individual test dog of a defined genotype (D1 or D2) with the gene expression of the reference and target data sets permits identification of the presence of liver disease.

According to the genotype, sylimarin is administered. If genotype is D1, sylimarin is effective in treating the liver disease, if the genotype is D2 another biologically active nutrient needs to be used.

Example 2

This is the use of individual samples from normal healthy sheep with different genotypes to diagnose disease conditions in affected unhealthy sheep, and identifies the nutrient composition to add to the feed to restore the health of the unhealthy sheep.

Reference Data Set

The individual blood samples were obtained from 20 normal healthy sheep of the Sardinian breed and 20 normal healthy sheep of the Bergamsca breed. The animals, selected within the flocks, were female, clinically healthy, not pregnant and not lactating and in normal body condition score. The age of the sheep ranged from 3 to 5 years. These animals represented the reference dataset for the two genotypes (G1 or G2).

Target Data Set

A second population of individual sheep was selected from the two breed flocks, Sardinian and Bergamasca, for having an inflammatory condition of laminitis. The number of individual affected unhealthy sheep was 10 for each breed. The sheep were female, not pregnant and not lactating and in normal body condition score. The age of the sheep ranged from 3 to 5 years. These animals represented the target dataset for the two genotypes (G1 or G2).

Nutrient Data Set

The animals were fed a maintenance ration, based on hay and concentrate, supplemented with 2 mg/kg body weight of dry extract of *Echinacea angustifolia* for 20 days. The samples collected from each of the animals after the treatment showed the effect of *Echinacea angustifolia* (nutrient dataset) for the two genotypes (G1 or G2). Animals after the treatment represented the nutrient data set.

Blood was sampled from each sheep of the reference, target and nutrient datasets and mRNA was extracted employing PAXgene blood RNA kit (PreAnalitiX—Qiagen). The mRNA from the individual healthy and unhealthy sheep of each breed and dataset and their individual gene expressions were analysed in duplicate using a custom microarray.

The probes of the microarray were designed with Oligowiz software, from a collection of gene sequences and EST and clustered, producing 12.194 Unigenes—NCBI. For each cluster two 35-40mer probes were designed. Quality check of all mRNA samples was performed with Agilent 2100 bio analyser. Two rounds of amplification of the target genes were performed with Ambion Amino Allyl MessageAmpTM II mRNA Amplification Kit. Labeling of target genes was achieved with Cy5 fluorophore, in duplicate, hybridized to microarray and scanned.

Scanning and image acquisition. Raw data were normalized using the function "Normalize Gene/Row Vectors" of MeV software and a two way analysis of variance (fixed factors genotype, G1 or G2; datasets, reference, target and nutrient), was performed with ANOVA (MeV software v4.1—TIGR). Results were considered statistically significant for p-values<0.01.

Hierarchical clustering analysis of differentially expressed genes and heat maps were generated for genes which were significantly different for interaction, treatment and time of sampling. (MeV software v 4.1—TIGR). Genes were annotated with HomoloGene system (about 50% of the genes present on the array have been annotated).

The number of genes which significantly differed in the individual sheep was 20 between genotypes and 12 between datasets. The interaction of genotype X dataset showed 20 genes differently expressed. In this example, only this last set of genes is reported.

As can be seen from the Tables, the two G1 or G2 genotypes of the individual normal healthy sheep showed different basal values of expression for the 20 genes, indicating the effect of the individuals of the two different breeds. Also the individual affected unhealthy sheep—i.e. with laminitis presented a different response to their inflammatory conditions. The administration of *Echinacea angustifolia* for 20 days was not able to restore the normal condition in the individual G1 Sardinian sheep. Conversely, the individual sheep of G2 Bergamasca breed responded positively to the treatment and the level of expression of the genes were similar to that of individual normal healthy animals of the reference dataset.

| | MEAN GENE EXPRESSION LEVELS | | | | | |
|---|---|---|---|---|---|---|
| Symbol | G1 Normal | G2 Normal | G1 Abnormal | G2 Abnormal | G1 Treated | G2 Treated |
| IL12RB1 | 111.71 | 113.32 | 96.50 | 151.59 | 133.20 | 116.75 |
| IL12RB1 | 97.73 | 154.96 | 108.07 | 168.91 | 137.83 | 152.11 |
| IL1F10 | 55.26 | 44.39 | 61.52 | 36.05 | 36.67 | 46.02 |
| IL1R2 | 204.99 | 233.22 | 199.82 | 145.04 | 186.25 | 234.70 |
| IL1RAP | 81.74 | 94.73 | 95.27 | 106.08 | 95.23 | 95.26 |
| IL1RN | 341.33 | 231.38 | 275.11 | 552.67 | 589.34 | 228.83 |
| IL27RA | 194.46 | 246.16 | 176.93 | 149.70 | 212.99 | 249.06 |
| IL4 | 97.25 | 68.70 | 77.13 | 93.49 | 90.59 | 69.78 |
| IL6 | 175.83 | 169.35 | 174.58 | 192.55 | 177.54 | 171.65 |
| IL8RA | 245.94 | 229.87 | 344.28 | 276.43 | 314.39 | 233.77 |
| TNC | 32.32 | 27.63 | 27.94 | 44.40 | 36.95 | 28.92 |
| TNF | 243.28 | 250.19 | 212.80 | 375.71 | 158.65 | 252.77 |
| TNFAIP2 | 181.50 | 150.84 | 174.51 | 191.25 | 184.31 | 150.80 |
| TNFAIP3 | 84.48 | 70.67 | 89.36 | 158.22 | 123.87 | 70.15 |
| TNFAIP6 | 29.90 | 52.14 | 36.56 | 21.54 | 52.95 | 50.84 |
| TNFAIP8 | 73.25 | 57.66 | 73.02 | 98.36 | 99.72 | 57.19 |
| TNFRSF13B | 96.70 | 91.02 | 119.69 | 89.34 | 75.10 | 90.07 |
| TNFRSF13C | 79.68 | 55.92 | 60.92 | 56.58 | 56.63 | 55.76 |
| TNFRSF1A | 97.06 | 112.97 | 107.37 | 102.81 | 99.32 | 114.12 |
| TNFRSF6B | 54.62 | 53.62 | 42.17 | 87.42 | 78.79 | 54.59 |

Hierarchical clustering, reported in the heat map figure, further shows the different molecular dietary signature of the individual sheep of the two breeds, as well as the positive therapeutic action of *Echinacea angustifolia*, in restoring the individual affected unhealthy sheep to the individual normal healthy condition. This is apparent from the homogeneous cluster that G2-1a and G2-1b produced with G2-3a and G2-3b.

The molecular dietary signatures of *Echinacea angustifolia* on the two genotypes are reported in the heat map.

Comparing the functional genomic profile of a test sample of sheep with known genotype with the reference and target dataset The diagnosis of inflammatory conditions in a sheep can be performed determining the functional genomic profile of a blood sample, using a gene expression microarray.

Genetic data of the individual sheep (i.e. breed) needs to be recorded.

The comparison of values for gene expression of the sample of an individual test sheep of a defined breed (G2 or G2) with the gene expression of the reference and target dataset permits the identification of the presence of inflammatory conditions.

According to the breed, *Echinacia angustifolia* is administered. If genotype is G1, *Echinacia angustifolia* is ineffective in treating the inflammatory conditions, if the genotype is G2 *Echinacia angustifolia* is effective in treating the inflammatory conditions.

Example 3

Using the technique of Example 1, the biologically active nutrient for kidney disease is identified. The relevant genes for this identification would include:

| Gene symbol | Description |
| --- | --- |
| A2M | alpha-2-macroglobulin |
| ABCB7 | ATP-binding cassette, sub-family B (MDR/TAP), member 7 |
| ABCC2 | ATP-binding cassette, sub-family C (CFTR/MRP), member 2 |
| ABI1 | abI-interactor 1 |
| ABL1 | c-abl oncogene 1, receptor tyrosine kinase |
| ABP1 | amiloride binding protein 1 (amine oxidase (copper-containing)) |
| ACAN | aggrecan |
| ACE | angiotensin I converting enzyme (peptidyl-dipeptidase A) 1 |
| ACY1 | aminoacylase 1 |
| ACYP2 | acylphosphatase 2, muscle type |
| ADAM10 | ADAM metallopeptidase domain 10 |
| ADAM28 | ADAM metallopeptidase domain 28 |
| ADAM9 | ADAM metallopeptidase domain 9 (meltrin gamma) |
| ADAMTS13 | ADAM metallopeptidase with thrombospondin type 1 motif, 13 |
| ADAMTS4 | ADAM metallopeptidase with thrombospondin type 1 motif, 4 |
| ADAMTS5 | ADAM metallopeptidase with thrombospondin type 1 motif, 5 |
| ADC | arginine decarboxylase |
| ADCY1 | adenylate cyclase 1 (brain) |
| ADI1 | acireductone dioxygenase 1 |
| ADORA2B | adenosine A2b receptor |
| ADRB3 | adrenergic, beta-3-, receptor |
| ADSL | adenylosuccinate lyase |
| AGER | advanced glycosylation end product-specific receptor |
| AGMAT | agmatine ureohydrolase (agmatinase) |
| AGT | angiotensinogen (serpin peptidase inhibitor, clade A, member 8) |
| AKR1C3 | aldo-keto reductase family 1, member C3 (3-alpha hydroxysteroid dehydrogenase, type II) |
| AKT1 | v-akt murine thymoma viral oncogene homolog 1 |
| AKT2 | v-akt murine thymoma viral oncogene homolog 2 |
| ALB | albumin |
| ALLC | allantoicase |
| AOC2 | amine oxidase, copper containing 2 (retina-specific) |
| AOC3 | amine oxidase, copper containing 3 (vascular adhesion protein 1) |
| AQP1 | aquaporin 1 (Colton blood group) |
| AQP10 | aquaporin 10 |
| AQP11 | aquaporin 11 |
| AQP2 | aquaporin 2 (collecting duct) |
| AQP3 | aquaporin 3 (Gill blood group) |
| AQP4 | aquaporin 4 |
| AQP7 | aquaporin 7 |
| AQP8 | aquaporin 8 |
| AQP9 | aquaporin 9 |
| AREG | amphiregulin (schwannoma-derived growth factor) |
| ARG1 | arginase, liver |
| ARG2 | arginase, type II |
| ARHGAP5 | Rho GTPase activating protein 5 |
| ASL | argininosuccinate lyase |
| ASS1 | argininosuccinate synthetase 1 |
| B2M | beta-2-microglobulin |
| BATF3 | basic leucine zipper transcription factor, ATF-like 3 |
| CA1 | carbonic anhydrase I |
| CA2 | carbonic anhydrase II |
| CA9 | carbonic anhydrase IX |
| CALR | calreticulin |
| CAV1 | caveolin 1, caveolae protein, 22 kDa |
| CCL4 | chemokine (C-C motif) ligand 4 |
| CCL5 | chemokine (C-C motif) ligand 5 |
| CCNE2 | cyclin E2 |
| CCR3 | chemokine (C-C motif) receptor 3 |
| CCR5 | chemokine (C-C motif) receptor 5 |
| CDH1 | cadherin 1, type 1, E-cadherin (epithelial) |
| CDH5 | cadherin 5, type 2 (vascular endothelium) |
| CEACAM5 | carcinoembryonic antigen-related cell adhesion molecule 5 |
| CEBPB | CCAAT/enhancer binding protein (C/EBP), beta |
| CES1 | carboxylesterase 1 (monocyte/macrophage serine esterase 1) |
| CFLAR | CASP8 and FADD-like apoptosis regulator |
| CGB5 | chorionic gonadotropin, beta polypeptide 5 |
| CLDN4 | claudin 4 |
| CLU | clusterin |
| COL18A1 | collagen, type XVIII, alpha 1 |
| COL1A1 | collagen, type I, alpha 1 |
| COL1A2 | collagen, type I, alpha 2 |
| COL3A1 | collagen, type III, alpha 1 |
| COL4A1 | collagen, type IV, alpha 1 |
| COL4A2 | collagen, type IV, alpha 2 |
| COL4A3 | collagen, type IV, alpha 3 (Goodpasture antigen) |

| Gene symbol | Description |
| --- | --- |
| COL4A4 | collagen, type IV, alpha 4 |
| COL4A5 | collagen, type IV, alpha 5 |
| COL4A6 | collagen, type IV, alpha 6 |
| CPS1 | carbamoyl-phosphate synthetase 1, mitochondrial |
| CREB1 | cAMP responsive element binding protein 1 |
| CRP | C-reactive protein, pentraxin-related |
| CRYAB | crystallin, alpha B |
| CSDA | cold shock domain protein A |
| CSF3 | colony stimulating factor 3 (granulocyte) |
| CSK | c-src tyrosine kinase |
| CSPG4 | chondroitin sulfate proteoglycan 4 |
| CTGF | connective tissue growth factor |
| CXCL12 | chemokine (C—X—C motif) ligand 12 (stromal cell-derived factor 1) |
| CXCL5 | chemokine (C—X—C motif) ligand 5 |
| CXCL6 | chemokine (C—X—C motif) ligand 6 (granulocyte chemotactic protein 2) |
| CXCR4 | chemokine (C—X—C motif) receptor 4 |
| CYP1A2 | cytochrome P450, family 1, subfamily A, polypeptide 2 |
| CYP2B6 | cytochrome P450, family 2, subfamily B, polypeptide 6 |
| CYR61 | cysteine-rich, angiogenic inducer, 61 |
| EGFR | epidermal growth factor receptor (erythroblastic leukemia viral (v-erb-b) oncogene homolog, avian) |
| EIF4B | eukaryotic translation initiation factor 4B |
| ELAVL1 | ELAV (embryonic lethal, abnormal vision, Drosophila)-like 1 (Hu antigen R) |
| ELF3 | E74-like factor 3 (ets domain transcription factor, epithelial-specific) |
| ENPP1 | ectonucleotide pyrophosphatase/phosphodiesterase 1 |
| EPHA2 | EPH receptor A2 |
| EPHX2 | epoxide hydrolase 2, cytoplasmic |
| EPO | erythropoietin |
| ERBB4 | v-erb-a erythroblastic leukemia viral oncogene homolog 4 (avian) |
| ESR2 | estrogen receptor 2 (ER beta) |
| ETS1 | v-ets erythroblastosis virus E26 oncogene homolog 1 (avian) |
| ETV1 | ets variant gene 1 |
| ETV4 | ets variant gene 4 (E1A enhancer binding protein, E1AF) |
| ETV5 | ets variant gene 5 (ets-related molecule) |
| ETV7 | ets variant gene 7 (TEL2 oncogene) |
| F12 | coagulation factor XII (Hageman factor) |
| F13A1 | coagulation factor XIII, A1 polypeptide |
| F13A2 | coagulation factor XIII, A2 polypeptide |
| F2 | coagulation factor II (thrombin) |
| F2R | coagulation factor II (thrombin) receptor |
| F5 | coagulation factor V (proaccelerin, labile factor) |
| FABP2 | fatty acid binding protein 2, intestinal |
| FASLG | Fas ligand (TNF superfamily, member 6) |
| FBLN2 | fibulin 2 |
| FGA | fibrinogen alpha chain |
| FGF13 | fibroblast growth factor 13 |
| FGF2 | fibroblast growth factor 2 (basic) |
| FGF4 | fibroblast growth factor 4 (heparin secretory transforming protein 1, Kaposi sarcoma oncogene) |
| FGF5 | fibroblast growth factor 5 |
| FH | fumarate hydratase |
| FKBP1A | FK506 binding protein 1A, 12 kDa |
| FLG | filaggrin |
| FN1 | fibronectin 1 |
| FOLH1 | folate hydrolase (prostate-specific membrane antigen) 1 |
| FOSB | FBJ murine osteosarcoma viral oncogene homolog B |
| FOSL1 | FOS-like antigen 1 |
| FURIN | furin (paired basic amino acid cleaving enzyme) |
| G6PC | glucose-6-phosphatase, catalytic subunit |
| GADD45B | growth arrest and DNA-damage-inducible, beta |
| GATM | glycine amidinotransferase (L-arginine:glycine amidinotransferase) |
| GBP1 | guanylate binding protein 1, interferon-inducible, 67 kDa |
| GC | group-specific component (vitamin D binding protein) |
| GCGR | glucagon receptor |
| GGT1 | gamma-glutamyltransferase 1 |
| GH1 | growth hormone 1 |
| GHRH | growth hormone releasing hormone |
| GHRL | ghrelin/obestatin prepropeptide |
| GLB1 | galactosidase, beta 1 |
| GLO1 | glyoxalase I |
| GLS | glutaminase |
| GLS2 | glutaminase 2 (liver, mitochondrial) |
| GLUD1 | glutamate dehydrogenase 1 |
| GLUL | glutamate-ammonia ligase (glutamine synthetase) |
| GNMT | glycine N-methyltransferase |
| GOT1 | glutamic-oxaloacetic transaminase 1, soluble (aspartate aminotransferase 1) |

-continued

| Gene symbol | Description |
|---|---|
| GOT2 | glutamic-oxaloacetic transaminase 2, mitochondrial (aspartate aminotransferase 2) |
| GPRC6A | G protein-coupled receptor, family C, group 6, member A |
| GPT | glutamic-pyruvate transaminase (alanine aminotransferase) |
| GRLF1 | glucocorticoid receptor DNA binding factor 1 |
| GRN | granulin |
| HBEGF | heparin-binding EGF-like growth factor |
| HELLS | helicase, lymphoid-specific |
| HGF | hepatocyte growth factor (hepapoietin A; scatter factor) |
| HIF1A | hypoxia-inducible factor 1, alpha subunit (basic helix-loop-helix transcription factor) |
| HIST2H3C | histone cluster 2, H3c |
| HLA-DRB1 | major histocompatibility complex, class II, DR beta 1 |
| HLA-G | major histocompatibility complex, class I, G |
| HNF4A | hepatocyte nuclear factor 4, alpha |
| HP | haptoglobin |
| HPSE | heparanase |
| HPX | hemopexin |
| HRH2 | histamine receptor H2 |
| HSBP1 | heat shock factor binding protein 1 |
| HSP90AA2 | heat shock protein 90 kDa alpha (cytosolic), class A member 2 |
| HSPA1A | heat shock 70 kDa protein 1A |
| HSPA4L | heat shock 70 kDa protein 4-like |
| HSPA8 | heat shock 70 kDa protein 8 |
| HSPB2 | heat shock 27 kDa protein 2 |
| HSPD1 | heat shock 60 kDa protein 1 (chaperonin) |
| HSPE1 | heat shock 10 kDa protein 1 (chaperonin 10) |
| IBSP | integrin-binding sialoprotein |
| ICAM1 | intercellular adhesion molecule 1 |
| IGF1R | insulin-like growth factor 1 receptor |
| IGF2 | insulin-like growth factor 2 (somatomedin A) |
| IL10 | interleukin 10 |
| IL11RA | interleukin 11 receptor, alpha |
| IL13 | interleukin 13 |
| IL17RA | interleukin 17 receptor A |
| IL18 | interleukin 18 (interferon-gamma-inducing factor) |
| IL1B | interleukin 1, beta |
| IL5 | interleukin 5 (colony-stimulating factor, eosinophil) |
| IL6 | interleukin 6 (interferon, beta 2) |
| IL8 | interleukin 8 |
| IL8RB | interleukin 8 receptor, beta |
| ILK | integrin-linked kinase |
| ITGA2B | integrin, alpha 2b (platelet glycoprotein IIb of IIb/IIIa complex, antigen CD41) |
| ITGA3 | integrin, alpha 3 (antigen CD49C, alpha 3 subunit of VLA-3 receptor) |
| ITGA4 | integrin, alpha 4 (antigen CD49D, alpha 4 subunit of VLA-4 receptor) |
| ITGAV | integrin, alpha V (vitronectin receptor, alpha polypeptide, antigen CD51) |
| ITGB1 | integrin, beta 1 (fibronectin receptor, beta polypeptide, antigen CD29 includes MDF2, MSK12) |
| ITGB3 | integrin, beta 3 (platelet glycoprotein IIIa, antigen CD61) |
| ITGB4 | integrin, beta 4 |
| ITGB6 | integrin, beta 6 |
| ITGB8 | integrin, beta 8 |
| ITIH4 | inter-alpha (globulin) inhibitor H4 (plasma Kallikrein-sensitive glycoprotein) |
| IVL | involucrin |
| JPH4 | junctophilin 4 |
| JUN | jun oncogene |
| JUNB | jun B proto-oncogene |
| KDR | kinase insert domain receptor (a type III receptor tyrosine kinase) |
| KLF12 | Kruppel-like factor 12 |
| KLKB1 | kallikrein B, plasma (Fletcher factor) 1 |
| KRT14 | keratin 14 (epidermolysis bullosa simplex, Dowling-Meara, Koebner) |
| KRT18 | keratin 18 |
| KRT5 | keratin 5 (epidermolysis bullosa simplex, Dowling-Meara/Kobner/Weber-Cockayne types) |
| KRT8 | keratin 8 |
| LALBA | lactalbumin, alpha- |
| LAMC2 | laminin, gamma 2 |
| LCN1 | lipocalin 1 (tear prealbumin) |
| LCN2 | lipocalin 2 |
| LEF1 | lymphoid enhancer-binding factor 1 |
| LGALS7 | lectin, galactoside-binding, soluble, 7 |
| LIMS1 | LIM and senescent cell antigen-like domains 1 |
| LOC732415 | similar to Matrix metalloproteinase-19 precursor (MMP-19) (Matrix metalloproteinase RASI) (MMP-18) |
| LOX | lysyl oxidase |
| LPA | lipoprotein, Lp(a) |
| LRP1 | low density lipoprotein-related protein 1 (alpha-2-macroglobulin receptor) |
| LRPAP1 | low density lipoprotein receptor-related protein associated protein 1 |
| MAOA | monoamine oxidase A |

-continued

| Gene symbol | Description |
|---|---|
| MAOB | monoamine oxidase B |
| MAP2K1 | mitogen-activated protein kinase kinase 1 |
| MAP2K2 | mitogen-activated protein kinase kinase 2 |
| MAP2K3 | mitogen-activated protein kinase kinase 3 |
| MAP2K5 | mitogen-activated protein kinase kinase 5 |
| MAP2K6 | mitogen-activated protein kinase kinase 6 |
| MAP3K1 | mitogen-activated protein kinase kinase kinase 1 |
| MAP3K7 | mitogen-activated protein kinase kinase kinase 7 |
| MAPK1 | mitogen-activated protein kinase 1 |
| MAPK10 | mitogen-activated protein kinase 10 |
| MAPK11 | mitogen-activated protein kinase 11 |
| MAPK14 | mitogen-activated protein kinase 14 |
| MAPK3 | mitogen-activated protein kinase 3 |
| MAPK7 | mitogen-activated protein kinase 7 |
| MAPK8 | mitogen-activated protein kinase 8 |
| MAPK9 | mitogen-activated protein kinase 9 |
| MAPT | microtubule-associated protein tau |
| MAZ | MYC-associated zinc finger protein (purine-binding transcription factor) |
| MBP | myelin basic protein |
| MCCC1 | methylcrotonoyl-Coenzyme A carboxylase 1 (alpha) |
| MCHR1 | melanin-concentrating hormone receptor 1 |
| MCRS1 | microspherule protein 1 |
| MDH1 | malate dehydrogenase 1, NAD (soluble) |
| MDH2 | malate dehydrogenase 2, NAD (mitochondrial) |
| MEP1B | meprin A, beta |
| MEPE | matrix, extracellular phosphoglycoprotein with ASARM motif (bone) |
| MIF | macrophage migration inhibitory factor (glycosylation-inhibiting factor) |
| MIP | major intrinsic protein of lens fiber |
| MKI67 | antigen identified by monoclonal antibody Ki-67 |
| MLNR | motilin receptor |
| MMP1 | matrix metallopeptidase 1 (interstitial collagenase) |
| MMP10 | matrix metallopeptidase 10 (stromelysin 2) |
| MMP11 | matrix metallopeptidase 11 (stromelysin 3) |
| MMP12 | matrix metallopeptidase 12 (macrophage elastase) |
| MMP13 | matrix metallopeptidase 13 (collagenase 3) |
| MMP14 | matrix metallopeptidase 14 (membrane-inserted) |
| MMP15 | matrix metallopeptidase 15 (membrane-inserted) |
| MMP16 | matrix metallopeptidase 16 (membrane-inserted) |
| MMP17 | matrix metallopeptidase 17 (membrane-inserted) |
| MMP19 | matrix metallopeptidase 19 |
| MMP2 | matrix metallopeptidase 2 (gelatinase A, 72 kDa gelatinase, 72 kDa type IV collagenase) |
| MMP20 | matrix metallopeptidase 20 |
| MMP21 | matrix metallopeptidase 21 |
| MMP23A | matrix metallopeptidase 23A (pseudogene) |
| MMP23B | matrix metallopeptidase 23B |
| MMP24 | matrix metallopeptidase 24 (membrane-inserted) |
| MMP25 | matrix metallopeptidase 25 |
| MMP26 | matrix metallopeptidase 26 |
| MMP27 | matrix metallopeptidase 27 |
| MMP28 | matrix metallopeptidase 28 |
| MMP3 | matrix metallopeptidase 3 (stromelysin 1, progelatinase) |
| MMP7 | matrix metallopeptidase 7 (matrilysin, uterine) |
| MMP8 | matrix metallopeptidase 8 (neutrophil collagenase) |
| MMP9 | matrix metallopeptidase 9 (gelatinase B, 92 kDa gelatinase, 92 kDa type IV collagenase) |
| MPV17 | MpV17 mitochondrial inner membrane protein |
| MRC1 | mannose receptor, C type 1 |
| MRC2 | mannose receptor, C type 2 |
| MRGPRX1 | MAS-related GPR, member X1 |
| MSBP3 | minisatellite binding protein 3, 115 kDa |
| MSH6 | mutS homolog 6 (*E. coli*) |
| MUC1 | mucin 1, cell surface associated |
| MYLK | myosin light chain kinase |
| NAGLU | N-acetylglucosaminidase, alpha- |
| NAGS | N-acetylglutamate synthase |
| NAMPT | nicotinamide phosphoribosyltransferase |
| NANOS1 | nanos homolog 1 (*Drosophila*) |
| NCL | nucleolin |
| NCOR2 | nuclear receptor co-repressor 2 |
| NFAT5 | nuclear factor of activated T-cells 5, tonicity-responsive |
| NFKB1 | nuclear factor of kappa light polypeptide gene enhancer in B-cells 1 |
| NKRF | NFKB repressing factor |
| NOS1 | nitric oxide synthase 1 (neuronal) |
| NOS2A | nitric oxide synthase 2A (inducible, hepatocytes) |
| NOS3 | nitric oxide synthase 3 (endothelial cell) |
| NPEPPS | aminopeptidase puromycin sensitive |
| NPY5R | neuropeptide Y receptor Y5 |

-continued

| Gene symbol | Description |
|---|---|
| NR1H2 | nuclear receptor subfamily 1, group H, member 2 |
| NR1I3 | nuclear receptor subfamily 1, group I, member 3 |
| NR4A1 | nuclear receptor subfamily 4, group A, member 1 |
| NRP2 | neuropilin 2 |
| NTRK1 | neurotrophic tyrosine kinase, receptor, type 1 |
| OAT | ornithine aminotransferase (gyrate atrophy) |
| OCLN | occludin |
| ODC1 | ornithine decarboxylase 1 |
| OPTC | opticin |
| OTC | ornithine carbamoyltransferase |
| OVOS | ovostatin |
| OXA1L | oxidase (cytochrome c) assembly 1-like |
| P4HB | procollagen-proline, 2-oxoglutarate 4-dioxygenase (proline 4-hydroxylase), beta polypeptide |
| PAH | phenylalanine hydroxylase |
| PC | pyruvate carboxylase |
| PCK2 | phosphoenolpyruvate carboxykinase 2 (mitochondrial) |
| PCNT | pericentrin |
| PCSK6 | proprotein convertase subtilisin/kexin type 6 |
| PCSK7 | proprotein convertase subtilisin/kexin type 7 |
| PDIA2 | protein disulfide isomerase family A, member 2 |
| PF4 | platelet factor 4 (chemokine (C—X—C motif) ligand 4) |
| PHB | prohibitin |
| PHEX | phosphate regulating endopeptidase homolog, X-linked |
| PI3 | peptidase inhibitor 3, skin-derived (SKALP) |
| PIK3C2A | phosphoinositide-3-kinase, class 2, alpha polypeptide |
| PLA2G1B | phospholipase A2, group IB (pancreas) |
| PLAU | plasminogen activator, urokinase |
| PLEKHF1 | pleckstrin homology domain containing, family F (with FYVE domain) member 1 |
| PLG | plasminogen |
| PLXNB1 | plexin B1 |
| PLXNC1 | plexin C1 |
| POR | P450 (cytochrome) oxidoreductase |
| PPARA | peroxisome proliferator-activated receptor alpha |
| PPARG | peroxisome proliferator-activated receptor gamma |
| PPIA | peptidylprolyl isomerase A (cyclophilin A) |
| PRDM2 | PR domain containing 2, with ZNF domain |
| PREP | prolyl endopeptidase |
| PRKACA | protein kinase, cAMP-dependent, catalytic, alpha |
| PRKCA | protein kinase C, alpha |
| PRKG1 | protein kinase, cGMP-dependent, type I |
| PRSS2 | protease, serine, 2 (trypsin 2) |
| PRSS7 | protease, serine, 7 (enterokinase) |
| PRTN3 | proteinase 3 |
| PSG2 | pregnancy specific beta-1-glycoprotein 2 |
| PSMB8 | proteasome (prosome, macropain) subunit, beta type, 8 (large multifunctional peptidase 7) |
| PSMC6 | proteasome (prosome, macropain) 26S subunit, ATPase, 6 |
| PTAFR | platelet-activating factor receptor |
| PTEN | phosphatase and tensin homolog |
| PTGER4 | prostaglandin E receptor 4 (subtype EP4) |
| PTGIR | prostaglandin I2 (prostacyclin) receptor (IP) |
| PTGIS | prostaglandin I2 (prostacyclin) synthase |
| PTGS2 | prostaglandin-endoperoxide synthase 2 (prostaglandin G/H synthase and cyclooxygenase) |
| PTK2 | PTK2 protein tyrosine kinase 2 |
| PTK7 | PTK7 protein tyrosine kinase 7 |
| PTN | pleiotrophin |
| PTTG1 | pituitary tumor-transforming 1 |
| PYGB | phosphorylase, glycogen; brain |
| RAB8A | RAB8A, member RAS oncogene family |
| RAC1 | ras-related C3 botulinum toxin substrate 1 (rho family, small GTP binding protein Rac1) |
| RAD51 | RAD51 homolog (RecA homolog, E. coli) (S. cerevisiae) |
| RBP4 | retinol binding protein 4, plasma |
| RECK | reversion-inducing-cysteine-rich protein with kazal motifs |
| RELA | v-rel reticuloendotheliosis viral oncogene homolog A (avian) |
| RETN | resistin |
| RHOA | ras homolog gene family, member A |
| RLN1 | relaxin 1 |
| RLN2 | relaxin 2 |
| RPE | ribulose-5-phosphate-3-epimerase |
| RRM2 | ribonucleotide reductase M2 polypeptide |
| RUNX2 | runt-related transcription factor 2 |
| S100A8 | S100 calcium binding protein A8 |
| SAT1 | spermidine/spermine N1-acetyltransferase 1 |
| SAT2 | spermidine/spermine N1-acetyltransferase family member 2 |

-continued

| Gene symbol | Description |
|---|---|
| SERPINA3 | serpin peptidase inhibitor, clade A (alpha-1 antiproteinase, antitrypsin), member 3 |
| SERPINA7 | serpin peptidase inhibitor, clade A (alpha-1 antiproteinase, antitrypsin), member 7 |
| SERPINB1 | serpin peptidase inhibitor, clade B (ovalbumin), member 1 |
| SERPINB3 | serpin peptidase inhibitor, clade B (ovalbumin), member 3 |
| SERPINE1 | serpin peptidase inhibitor, clade E (nexin, plasminogen activator inhibitor type 1), member 1 |
| SERPINF2 | serpin peptidase inhibitor, clade F (alpha-2 antiplasmin, pigment epithelium derived factor), member 2 |
| SERPINH1 | serpin peptidase inhibitor, clade H (heat shock protein 47), member 1, (collagen binding protein 1) |
| SFN | stratifin |
| SLAMF7 | SLAM family member 7 |
| SLC14A2 | solute carrier family 14 (urea transporter), member 2 |
| SLC17A5 | solute carrier family 17 (anion/sugar transporter), member 5 |
| SLC1A3 | solute carrier family 1 (glial high affinity glutamate transporter), member 3 |
| SLC25A10 | solute carrier family 25 (mitochondrial carrier; dicarboxylate transporter), member 10 |
| SLC25A12 | solute carrier family 25 (mitochondrial carrier, Aralar), member 12 |
| SLC25A13 | solute carrier family 25, member 13 (citrin) |
| SLC25A15 | solute carrier family 25 (mitochondrial carrier; ornithine transporter) member 15 |
| SLC25A2 | solute carrier family 25 (mitochondrial carrier; ornithine transporter) member 2 |
| SLC2A1 | solute carrier family 2 (facilitated glucose transporter), member 1 |
| SLC2A10 | solute carrier family 2 (facilitated glucose transporter), member 10 |
| SLC2A3 | solute carrier family 2 (facilitated glucose transporter), member 3 |
| SLC2A5 | solute carrier family 2 (facilitated glucose/fructose transporter), member 5 |
| SLC2A6 | solute carrier family 2 (facilitated glucose transporter), member 6 |
| SLC2A8 | solute carrier family 2, (facilitated glucose transporter) member 8 |
| SLC2A9 | solute carrier family 2 (facilitated glucose transporter), member 9 |
| SLC37A4 | solute carrier family 37 (glucose-6-phosphate transporter), member 4 |
| SLC38A1 | solute carrier family 38, member 1 |
| SLPI | secretory leukocyte peptidase inhibitor |
| SLPI | secretory leukocyte peptidase inhibitor |
| SMAD1 | SMAD family member 1 |
| SMPD2 | sphingomyelin phosphodiesterase 2, neutral membrane (neutral sphingomyelinase) |
| SMPD3 | sphingomyelin phosphodiesterase 3, neutral membrane (neutral sphingomyelinase II) |
| SMS | spermine synthase |
| SNAI1 | snail homolog 1 (*Drosophila*) |
| SNAP23 | synaptosomal-associated protein, 23 kDa |
| SNAPIN | SNAP-associated protein |
| SOD3 | superoxide dismutase 3, extracellular |
| SPARC | secreted protein, acidic, cysteine-rich (osteonectin) |
| SPOCK3 | sparc/osteonectin, cwcv and kazal-like domains proteoglycan (testican) 3 |
| SPP1 | secreted phosphoprotein 1 |
| SRM | spermidine synthase |
| STAR | steroidogenic acute regulatory protein |
| STAT3 | signal transducer and activator of transcription 3 (acute-phase response factor) |
| STX4 | syntaxin 4 |
| SUMO1 | SMT3 suppressor of mif two 3 homolog 1 (*S. cerevisiae*) |
| TAT | tyrosine aminotransferase |
| TEK | TEK tyrosine kinase, endothelial |
| TFAP2A | transcription factor AP-2 alpha (activating enhancer binding protein 2 alpha) |
| TFAP2B | transcription factor AP-2 beta (activating enhancer binding protein 2 beta) |
| TFAP2C | transcription factor AP-2 gamma (activating enhancer binding protein 2 gamma) |
| TFPI2 | tissue factor pathway inhibitor 2 |
| TGFB1 | transforming growth factor, beta 1 |
| TGM2 | transglutaminase 2 (C polypeptide, protein-glutamine-gamma-glutamyltransferase) |
| THBS1 | thrombospondin 1 |
| THBS2 | thrombospondin 2 |
| TIMP1 | TIMP metallopeptidase inhibitor 1 |
| TIMP2 | TIMP metallopeptidase inhibitor 2 |
| TIMP3 | TIMP metallopeptidase inhibitor 3 |
| TIMP4 | TIMP metallopeptidase inhibitor 4 |
| TNF | tumor necrosis factor (TNF superfamily, member 2) |
| TP53 | tumor protein p53 |
| TRH | thyrotropin-releasing hormone |
| TSPAN7 | tetraspanin 7 |
| TTR | transthyretin |
| TUBB | tubulin, beta |
| TUSC4 | tumor suppressor candidate 4 |
| TYRP1 | tyrosinase-related protein 1 |
| UCN | urocortin |
| UMOD | uromodulin |
| UTS2R | urotensin 2 receptor |
| VAMP2 | vesicle-associated membrane protein 2 (synaptobrevin 2) |
| VCAM1 | vascular cell adhesion molecule 1 |
| VCL | vinculin |
| VEGFA | vascular endothelial growth factor A |
| VTN | vitronectin |

-continued

| Gene symbol | Description |
| --- | --- |
| WASF3 | WAS protein family, member 3 |
| WEE1 | WEE1 homolog (*S. pombe*) |
| YBX1 | Y box binding protein 1 |
| ZEB2 | zinc finger E-box binding homeobox 2 |
| ZNF148 | zinc finger protein 148 |
| ZNF267 | zinc finger protein 267 |
| ZNF318 | zinc finger protein 318 |

Example 4

Using the technique of Example 1, the biologically active nutrient for inflammatory and immune disease is identified. The relevant genes for this identification would include:

| Gene symbol | Description |
| --- | --- |
| AKT1 | v-akt murine thymoma viral oncogene homolog 1 |
| AMHR2 | anti-Mullerian hormone receptor, type II |
| APAF1 | apoptotic peptidase activating factor 1 |
| APEX1 | APEX nuclease (multifunctional DNA repair enzyme) 1 |
| APOBEC1 | apolipoprotein B mRNA editing enzyme, catalytic polypeptide 1 |
| ATAD5 | ATPase family, AAA domain containing 5 |
| BAD | BCL2-antagonist of cell death |
| BAG1 | BCL2-associated athanogene |
| BAG2 | BCL2-associated athanogene 2 |
| BAG3 | BCL2-associated athanogene 3 |
| BAG4 | BCL2-associated athanogene 4 |
| BAG5 | BCL2-associated athanogene 5 |
| BAK1 | BCL2-antagonist/killer 1 |
| BAX | BCL2-associated X protein |
| BBC3 | BCL2 binding component 3 |
| BCAP29 | B-cell receptor-associated protein 29 |
| BCAP31 | B-cell receptor-associated protein 31 |
| BCL10 | B-cell CLL/lymphoma 10 |
| BCL2 | B-cell CLL/lymphoma 2 |
| BCL2A1 | BCL2-related protein A1 |
| BCL2L1 | BCL2-like 1 |
| BCL2L10 | BCL2-like 10 (apoptosis facilitator) |
| BCL2L11 | BCL2-like 11 (apoptosis facilitator) |
| BCL2L12 | BCL2-like 12 (proline rich) |
| BCL2L13 | BCL2-like 13 (apoptosis facilitator) |
| BCL2L14 | BCL2-like 14 (apoptosis facilitator) |
| BCL2L15 | BCL2-like 15 |
| BCL2L2 | BCL2-like 2 |
| BCL2L7P1 | BCL2-like 7 pseudogene 1 |
| BCL2L7P2 | BCL2-like 7 pseudogene 2 |
| BID | BH3 interacting domain death agonist |
| BIK | BCL2-interacting killer (apoptosis-inducing) |
| BIRC2 | baculoviral IAP repeat-containing 2 |
| BIRC5 | baculoviral IAP repeat-containing 5 (survivin) |
| BMF | Bcl2 modifying factor |
| BNIP1 | BCL2/adenovirus E1B 19 kDa interacting protein 1 |
| BNIP2 | BCL2/adenovirus E1B 19 kDa interacting protein 2 |
| BOK | BCL2-related ovarian killer |
| CAMKK1 | calcium/calmodulin-dependent protein kinase kinase 1, alpha |
| CARD10 | caspase recruitment domain family, member 10 |
| CARD8 | caspase recruitment domain family, member 8 |
| CASP1 | caspase 1, apoptosis-related cysteine peptidase (interleukin 1, beta, convertase) |
| CASP3 | caspase 3, apoptosis-related cysteine peptidase |
| CASP7 | caspase 7, apoptosis-related cysteine peptidase |
| CASP8 | caspase 8, apoptosis-related cysteine peptidase |
| CC2D1A | coiled-coil and C2 domain containing 1A |
| CHUK | conserved helix-loop-helix ubiquitous kinase |
| CIAPIN1 | cytokine induced apoptosis inhibitor 1 |
| CNDP2 | CNDP dipeptidase 2 (metallopeptidase M20 family) |
| COP1 | caspase-1 dominant-negative inhibitor pseudo-ICE |
| CP | ceruloplasmin (ferroxidase) |

-continued

| Gene symbol | Description |
|---|---|
| CREBBP | CREB binding protein (Rubinstein-Taybi syndrome) |
| CXCL12 | chemokine (C—X—C motif) ligand 12 (stromal cell-derived factor 1) |
| CXCL5 | chemokine (C—X—C motif) ligand 5 |
| CYCS | cytochrome c, somatic |
| CYP24A1 | cytochrome P450, family 24, subfamily A, polypeptide 1 |
| DDIT3 | DNA-damage-inducible transcript 3 |
| EDN1 | endothelin 1 |
| EGF | epidermal growth factor (beta-urogastrone) |
| EGFR | epidermal growth factor receptor |
| EIF4A1 | eukaryotic translation initiation factor 4A, isoform 1 |
| EIF4A2 | eukaryotic translation initiation factor 4A, isoform 2 |
| EP300 | E1A binding protein p300 |
| F3 | coagulation factor III (thromboplastin, tissue factor) |
| FAIM3 | Fas apoptotic inhibitory molecule 3 |
| FAS | Fas (TNF receptor superfamily, member 6) |
| FASLG | Fas ligand (TNF superfamily, member 6) |
| FGF1 | fibroblast growth factor 1 (acidic) |
| FGF10 | fibroblast growth factor 10 |
| FGF11 | fibroblast growth factor 11 |
| FGF12 | fibroblast growth factor 12 |
| FGF13 | fibroblast growth factor 13 |
| FGF14 | fibroblast growth factor 14 |
| FGF16 | fibroblast growth factor 16 |
| FGF17 | fibroblast growth factor 17 |
| FGF18 | fibroblast growth factor 18 |
| FGF19 | fibroblast growth factor 19 |
| FGF2 | fibroblast growth factor 2 (basic) |
| FGF20 | fibroblast growth factor 20 |
| FGF21 | fibroblast growth factor 21 |
| FGF22 | fibroblast growth factor 22 |
| FGF3 | fibroblast growth factor 3 |
| FGF4 | fibroblast growth factor 4 |
| FGF5 | fibroblast growth factor 5 |
| FGF6 | fibroblast growth factor 6 |
| FGF7 | fibroblast growth factor 7 (keratinocyte growth factor) |
| FGF8 | fibroblast growth factor 8 (androgen-induced) |
| FGF9 | fibroblast growth factor 9 (glia-activating factor) |
| HRAS | v-Ha-ras Harvey rat sarcoma viral oncogene homolog |
| HRB | HIV-1 Rev binding protein |
| HRK | harakiri, BCL2 interacting protein (contains only BH3 domain) |
| HSP90AA1 | heat shock protein 90 kDa alpha (cytosolic), class A member 1 |
| HSPA4 | heat shock 70 kDa protein 4 |
| HSPA8 | heat shock 70 kDa protein 8 |
| HTRA2 | HtrA serine peptidase 2 |
| ICAM1 | intercellular adhesion molecule 1 |
| IER3 | immediate early response 3 |
| IFNA4 | interferon, alpha 4 |
| IFNAR1 | interferon (alpha, beta and omega) receptor 1 |
| IFNAR2 | interferon (alpha, beta and omega) receptor 2 |
| IFNG | interferon, gamma |
| IGF1 | insulin-like growth factor 1 (somatomedin C) |
| IL10 | interleukin 10 |
| IL15RA | interleukin 15 receptor, alpha |
| IL17B | interleukin 17B |
| IL18BP | interleukin 18 binding protein |
| IL18R1 | interleukin 18 receptor 1 |
| IL18RAP | interleukin 18 receptor accessory protein |
| IL1A | interleukin 1, alpha |
| IL1B | interleukin 1, beta |
| IL1F10 | interleukin 1 family, member 10 (theta) |
| IL1F6 | interleukin 1 family, member 6 (epsilon) |
| IL1F8 | interleukin 1 family, member 8 (eta) |
| IL1R1 | interleukin 1 receptor, type I |
| IL1R2 | interleukin 1 receptor, type II |
| IL1RAP | interleukin 1 receptor accessory protein |
| IL1RAPL1 | interleukin 1 receptor accessory protein-like 1 |
| IL1RAPL2 | interleukin 1 receptor accessory protein-like 2 |
| IL1RL1 | interleukin 1 receptor-like 1 |
| IL1RL2 | interleukin 1 receptor-like 2 |
| IL1RN | interleukin 1 receptor antagonist |
| IL6 | interleukin 6 (interferon, beta 2) |
| IRAK1 | interleukin-1 receptor-associated kinase 1 |
| IRAK1 | interleukin-1 receptor-associated kinase 1 |
| IRAK2 | interleukin-1 receptor-associated kinase 2 |
| IRAK4 | interleukin-1 receptor-associated kinase 4 |
| IRF1 | interferon regulatory factor 1 |

-continued

| Gene symbol | Description |
|---|---|
| IRF9 | interferon regulatory factor 9 |
| ITGB4 | integrin, beta 4 |
| JAG1 | jagged 1 (Alagille syndrome) |
| JAK1 | Janus kinase 1 (a protein tyrosine kinase) |
| JUN | jun oncogene |
| JUNB | jun B proto-oncogene |
| KDSR | 3-ketodihydrosphingosine reductase |
| KGFLP1 | keratinocyte growth factor-like protein 1 |
| LAG3 | lymphocyte-activation gene 3 |
| LAMA2 | laminin, alpha 2 (merosin, congenital muscular dystrophy) |
| LBR | lamin B receptor |
| MAP2K1 | mitogen-activated protein kinase kinase 1 |
| MAP2K3 | mitogen-activated protein kinase kinase 3 |
| MAP2K4 | mitogen-activated protein kinase kinase 4 |
| MAP2K6 | mitogen-activated protein kinase kinase 6 |
| MAP3K1 | mitogen-activated protein kinase kinase kinase 1 |
| MAP3K14 | mitogen-activated protein kinase kinase kinase 14 |
| MAP3K3 | mitogen-activated protein kinase kinase kinase 3 |
| MAP3K7 | mitogen-activated protein kinase kinase kinase 7 |
| MAP3K7IP1 | mitogen-activated protein kinase kinase kinase 7 interacting protein 1 |
| MAP3K7IP2 | mitogen-activated protein kinase kinase kinase 7 interacting protein 2 |
| MAP3K7IP3 | mitogen-activated protein kinase kinase kinase 7 interacting protein 3 |
| MAPK1 | mitogen-activated protein kinase 1 |
| MAPK10 | mitogen-activated protein kinase 10 |
| MAPK14 | mitogen-activated protein kinase 14 |
| MAPK3 | mitogen-activated protein kinase 3 |
| MAPK8 | mitogen-activated protein kinase 8 |
| MAPK8IP2 | mitogen-activated protein kinase 8 interacting protein 2 |
| MAPK9 | mitogen-activated protein kinase 9 |
| MAPKAPK2 | mitogen-activated protein kinase-activated protein kinase 2 |
| MIRN15A | microRNA 15a |
| MKI67 | antigen identified by monoclonal antibody Ki-67 |
| MOAP1 | modulator of apoptosis 1 |
| MRPL41 | mitochondrial ribosomal protein L41 |
| MSH2 | mutS homolog 2, colon cancer, nonpolyposis type 1 (*E. coli*) |
| MSH6 | mutS homolog 6 (*E. coli*) |
| MUL1 | mitochondrial ubiquitin ligase activator of NFKB 1 |
| MYC | v-myc myelocytomatosis viral oncogene homolog (avian) |
| MYD88 | myeloid differentiation primary response gene (88) |
| NFATC1 | nuclear factor of activated T-cells, cytoplasmic, calcineurin-dependent 1 |
| NFATC2 | nuclear factor of activated T-cells, cytoplasmic, calcineurin-dependent 2 |
| NFKB1 | nuclear factor of kappa light polypeptide gene enhancer in B-cells 1 |
| NFKB2 | nuclear factor of kappa light polypeptide gene enhancer in B-cells 2 (p49/p100) |
| NFKBIA | nuclear factor of kappa light polypeptide gene enhancer in B-cells inhibitor, alpha |
| NFKBIB | nuclear factor of kappa light polypeptide gene enhancer in B-cells inhibitor, beta |
| NFKBID | nuclear factor of kappa light polypeptide gene enhancer in B-cells inhibitor, delta |
| NFKBIE | nuclear factor of kappa light polypeptide gene enhancer in B-cells inhibitor, epsilon |
| NFKBIE | nuclear factor of kappa light polypeptide gene enhancer in B-cells inhibitor, epsilon |
| NFKBIZ | nuclear factor of kappa light polypeptide gene enhancer in B-cells inhibitor, zeta |
| NKAP | NFKB activating protein |
| NKAPL | NFKB activating protein-like |
| NKIRAS1 | NFKB inhibitor interacting Ras-like 1 |
| NKIRAS2 | NFKB inhibitor interacting Ras-like 2 |
| NKRF | NFKB repressing factor |
| NLRP1 | NLR family, pyrin domain containing 1 |
| NOD2 | nucleotide-binding oligomerization domain containing 2 |
| NOS2A | nitric oxide synthase 2A (inducible, hepatocytes) |
| NOX4 | NADPH oxidase 4 |
| PAWR | PRKC, apoptosis, WT1, regulator |
| PI3 | peptidase inhibitor 3, skin-derived (SKALP) |
| PLCG2 | phospholipase C, gamma 2 (phosphatidylinositol-specific) |
| PLEKHG5 | pleckstrin homology domain containing, family G (with RhoGef domain) member 5 |
| PMAIP1 | phorbol-12-myristate-13-acetate-induced protein 1 |
| PPP1CA | protein phosphatase 1, catalytic subunit, alpha isoform |
| PPP1CB | protein phosphatase 1, catalytic subunit, beta isoform |
| PPP1CC | protein phosphatase 1, catalytic subunit, gamma isoform |
| PPP1R13L | protein phosphatase 1, regulatory (inhibitor) subunit 13 like |
| PPP1R1B | protein phosphatase 1, regulatory (inhibitor) subunit 1B |
| PPP2CA | protein phosphatase 2 (formerly 2A), catalytic subunit, alpha isoform |
| PPP2R4 | protein phosphatase 2A activator, regulatory subunit 4 |
| PPP2R5A | protein phosphatase 2, regulatory subunit B', alpha isoform |
| PRKACA | protein kinase, cAMP-dependent, catalytic, alpha |
| PRKCA | protein kinase C, alpha |
| PRKCZ | protein kinase C, zeta |
| PSIP1 | PC4 and SFRS1 interacting protein 1 |
| PTGIR | prostaglandin I2 (prostacyclin) receptor (IP) |

-continued

| Gene symbol | Description |
| --- | --- |
| PTGS2 | prostaglandin-endoperoxide synthase 2 (prostaglandin G/H synthase and cyclooxygenase) |
| PTGS2 | prostaglandin-endoperoxide synthase 2 (prostaglandin G/H synthase and cyclooxygenase) |
| REL | v-rel reticuloendotheliosis viral oncogene homolog (avian) |
| RELA | v-rel reticuloendotheliosis viral oncogene homolog A (avian) |
| RELB | v-rel reticuloendotheliosis viral oncogene homolog B |
| RIPK1 | receptor (TNFRSF)-interacting serine-threonine kinase 1 |
| RNF216 | ring finger protein 216 |
| RNF216L | ring finger protein 216-like |
| RNF25 | ring finger protein 25 |
| ROS1 | c-ros oncogene 1, receptor tyrosine kinase |
| RPL17 | ribosomal protein L17 |
| RTN3 | reticulon 3 |
| SATB1 | SATB homeobox 1 |
| SCNN1B | sodium channel, nonvoltage-gated 1, beta |
| SCNN1G | sodium channel, nonvoltage-gated 1, gamma |
| SERPINE1 | serpin peptidase inhibitor, clade E (nexin, plasminogen activator inhibitor type 1), member 1 |
| SIRT5 | sirtuin (silent mating type information regulation 2 homolog) 5 |
| SLC34A3 | solute carrier family 34 (sodium phosphate), member 3 |
| ST2 | suppression of tumorigenicity 2 |
| STAT1 | signal transducer and activator of transcription 1, 91 kDa |
| STAT2 | signal transducer and activator of transcription 2, 113 kDa |
| TANK | TRAF family member-associated NFKB activator |
| TBK1 | TANK-binding kinase 1 |
| TBKBP1 | TBK1 binding protein 1 |
| TGFB1 | transforming growth factor, beta 1 |
| TICAM2 | toll-like receptor adaptor molecule 2 |
| TMED4 | transmembrane emp24 protein transport domain containing 4 |
| TNF | tumor necrosis factor (TNF superfamily, member 2) |
| TNFAIP1 | tumor necrosis factor, alpha-induced protein 1 (endothelial) |
| TNFRSF10D | tumor necrosis factor receptor superfamily, member 10d, decoy with truncated death domain |
| TNFRSF11A | tumor necrosis factor receptor superfamily, member 11a, NFKB activator |
| TNFRSF11B | tumor necrosis factor receptor superfamily, member 11b |
| TNFRSF1A | tumor necrosis factor receptor superfamily, member 1A |
| TNFRSF4 | tumor necrosis factor receptor superfamily, member 4 |
| TNFSF10 | tumor necrosis factor (ligand) superfamily, member 10 |
| TNFSF11 | tumor necrosis factor (ligand) superfamily, member 11 |
| TNFSF14 | tumor necrosis factor (ligand) superfamily, member 14 |
| TOLLIP | toll interacting protein |
| TP53 | tumor protein p53 |
| TP53BP2 | tumor protein p53 binding protein, 2 |
| TRAF1 | TNF receptor-associated factor 1 |
| TRAF2 | TNF receptor-associated factor 2 |
| TRAF3 | TNF receptor-associated factor 3 |
| TRAF3IP2 | TRAF3 interacting protein 2 |
| TRAF5 | TNF receptor-associated factor 5 |
| TRAF6 | TNF receptor-associated factor 6 |
| TRAF6 | TNF receptor-associated factor 6 |
| TRIM38 | tripartite motif-containing 38 |
| TYK2 | tyrosine kinase 2 |

Example 5

Using the technique of Example 1, the biologically active nutrient for gastro intestinal disease is identified. The relevant genes for this identification would include:

| Gene symbol | Description |
| --- | --- |
| ALDH1A1 | aldehyde dehydrogenase 1 family, member A1 |
| ATP7B | ATPase, Cu++ transporting, beta polypeptide |
| CEBPB | CCAAT/enhancer binding protein (C/EBP), beta |
| CES1 | carboxylesterase 1 (monocyte/macrophage serine esterase 1) |
| CETP | cholesteryl ester transfer protein, plasma |
| CHUK | conserved helix-loop-helix ubiquitous kinase |
| CP | ceruloplasmin (ferroxidase) |
| CXCL12 | chemokine (C—X—C motif) ligand 12 (stromal cell-derived factor 1) |
| CXCL5 | chemokine (C—X—C motif) ligand 5 |
| CYP1A2 | cytochrome P450, family 1, subfamily A, polypeptide 2 |
| CYP2C19 | cytochrome P450, family 2, subfamily C, polypeptide 19 |

-continued

| Gene symbol | Description |
|---|---|
| CYP2C8 | cytochrome P450, family 2, subfamily C, polypeptide 8 |
| CYP2C9 | cytochrome P450, family 2, subfamily C, polypeptide 9 |
| CYP2J2 | cytochrome P450, family 2, subfamily J, polypeptide 2 |
| CYP3A | cytochrome P450, family 3, subfamily A |
| CYP3A4 | cytochrome P450, family 3, subfamily A, polypeptide 4 |
| CYP3A5 | cytochrome P450, family 3, subfamily A, polypeptide 5 |
| CYP51A1 | cytochrome P450, family 51, subfamily A, polypeptide 1 |
| DDX11 | DEAD/H (Asp-Glu-Ala-Asp/His) box polypeptide 11 |
| DHFR | dihydrofolate reductase |
| ECSIT | ECSIT homolog (*Drosophila*) |
| EDN1 | endothelin 1 |
| EFNB3 | ephrin-B3 |
| FGF19 | fibroblast growth factor 19 |
| FMO3 | flavin containing monooxygenase 3 |
| FOXO3 | forkhead box O3 |
| GSTA2 | glutathione S-transferase A2 |
| GSTM1 | glutathione S-transferase M1 |
| GSTM3 | glutathione S-transferase M3 (brain) |
| GSTP1 | glutathione S-transferase pi 1 |
| GSTT1 | glutathione S-transferase theta 1 |
| HMOX1 | heme oxygenase (decycling) 1 |
| HSF1 | heat shock transcription factor 1 |
| HSPB2 | heat shock 27 kDa protein 2 |
| IGHG1 | immunoglobulin heavy constant gamma 1 (G1m marker) |
| IGKC | immunoglobulin kappa constant |
| IKBKB | inhibitor of kappa light polypeptide gene enhancer in B-cells, kinase beta |
| IL10 | interleukin 10 |
| IL17B | interleukin 17B |
| IL18R1 | interleukin 18 receptor 1 |
| IL18RAP | interleukin 18 receptor accessory protein |
| IL1A | interleukin 1, alpha |
| IL1B | interleukin 1, beta |
| IL1F10 | interleukin 1 family, member 10 (theta) |
| IL1F6 | interleukin 1 family, member 6 (epsilon) |
| IL1F8 | interleukin 1 family, member 8 (eta) |
| IL1R1 | interleukin 1 receptor, type I |
| IL1R2 | interleukin 1 receptor, type II |
| IL1RAP | interleukin 1 receptor accessory protein |
| IL1RAPL1 | interleukin 1 receptor accessory protein-like 1 |
| IL1RAPL2 | interleukin 1 receptor accessory protein-like 2 |
| IL1RL1 | interleukin 1 receptor-like 1 |
| IL1RL2 | interleukin 1 receptor-like 2 |
| IL1RN | interleukin 1 receptor antagonist |
| IL2RG | interleukin 2 receptor, gamma (severe combined immunodeficiency) |
| IL6 | interleukin 6 (interferon, beta 2) |
| IRAK1 | interleukin-1 receptor-associated kinase 1 |
| IRAK2 | interleukin-1 receptor-associated kinase 2 |
| IRAK4 | interleukin-1 receptor-associated kinase 4 |
| IRF1 | interferon regulatory factor 1 |
| JUN | jun oncogene |
| KGFLP1 | keratinocyte growth factor-like protein 1 |
| LAG3 | lymphocyte-activation gene 3 |
| LBR | lamin B receptor |
| MAP2K3 | mitogen-activated protein kinase kinase 3 |
| MAP2K4 | mitogen-activated protein kinase kinase 4 |
| MAP2K6 | mitogen-activated protein kinase kinase 6 |
| MAP3K1 | mitogen-activated protein kinase kinase kinase 1 |
| MAP3K14 | mitogen-activated protein kinase kinase kinase 14 |
| MAP3K7 | mitogen-activated protein kinase kinase kinase 7 |
| MAP3K7IP1 | mitogen-activated protein kinase kinase kinase 7 interacting protein 1 |
| MAP3K7IP2 | mitogen-activated protein kinase kinase kinase 7 interacting protein 2 |
| MAP3K7IP3 | mitogen-activated protein kinase kinase kinase 7 interacting protein 3 |
| MAPK10 | mitogen-activated protein kinase 10 |
| MAPK14 | mitogen-activated protein kinase 14 |
| MAPK8 | mitogen-activated protein kinase 8 |
| MAPK8IP2 | mitogen-activated protein kinase 8 interacting protein 2 |
| MAPK9 | mitogen-activated protein kinase 9 |
| MT2A | metallothionein 2A |
| MTHFR | 5,10-methylenetetrahydrofolate reductase (NADPH) |
| MUC1 | mucin 1, cell surface associated |
| MYC | v-myc myelocytomatosis viral oncogene homolog (avian) |
| MYCN | v-myc myelocytomatosis viral related oncogene, neuroblastoma derived (avian) |
| MYD88 | myeloid differentiation primary response gene (88) |
| NFKB1 | nuclear factor of kappa light polypeptide gene enhancer in B-cells 1 |
| NFKB2 | nuclear factor of kappa light polypeptide gene enhancer in B-cells 2 (p49/p100) |
| NFKBIA | nuclear factor of kappa light polypeptide gene enhancer in B-cells inhibitor, alpha |
| NFKBIB | nuclear factor of kappa light polypeptide gene enhancer in B-cells inhibitor, beta |

-continued

| Gene symbol | Description |
| --- | --- |
| NFKBIE | nuclear factor of kappa light polypeptide gene enhancer in B-cells inhibitor, epsilon |
| NFYA | nuclear transcription factor Y, alpha |
| NR1I2 | nuclear receptor subfamily 1, group I, member 2 |
| NR1I3 | nuclear receptor subfamily 1, group I, member 3 |
| PI3 | peptidase inhibitor 3, skin-derived (SKALP) |
| POR | P450 (cytochrome) oxidoreductase |
| PPARA | peroxisome proliferator-activated receptor alpha |
| PPARD | peroxisome proliferator-activated receptor delta |
| PPARG | peroxisome proliferator-activated receptor gamma |
| PPARGC1A | peroxisome proliferator-activated receptor gamma, coactivator 1 alpha |
| PPARGC1B | peroxisome proliferator-activated receptor gamma, coactivator 1 beta |
| PRIC285 | peroxisomal proliferator-activated receptor A interacting complex |
| PRKCZ | protein kinase C, zeta |
| PTGS2 | prostaglandin-endoperoxide synthase 2 |
| RARA | retinoic acid receptor, alpha |
| RIPK1 | receptor (TNFRSF)-interacting serine-threonine kinase 1 |
| RNF216 | ring finger protein 216 |
| RNF216L | ring finger protein 216-like |
| RXRA | retinoid X receptor, alpha |
| RXRB | retinoid X receptor, beta |
| SCNN1B | sodium channel, nonvoltage-gated 1, beta |
| SCNN1G | sodium channel, nonvoltage-gated 1, gamma |
| SERPINE1 | serpin peptidase inhibitor, clade E |
| SIGIRR | single immunoglobulin and toll-interleukin 1 receptor (TIR) domain |
| SIRT1 | sirtuin (silent mating type information regulation 2 homolog) 1 (*S. cerevisiae*) |
| SLC34A3 | solute carrier family 34 (sodium phosphate), member 3 |
| ST2 | suppression of tumorigenicity 2 |
| TGFB1 | transforming growth factor, beta 1 |
| TICAM2 | toll-like receptor adaptor molecule 2 |
| TNF | tumor necrosis factor (TNF superfamily, member 2) |
| TNFAIP1 | tumor necrosis factor, alpha-induced protein 1 (endothelial) |
| TOLLIP | toll interacting protein |
| TP53 | tumor protein p53 |
| TP73 | tumor protein p73 |
| TRAF6 | TNF receptor-associated factor 6 |
| TRIM38 | tripartite motif-containing 38 |
| UBE2N | ubiquitin-conjugating enzyme E2N (UBC13 homolog, yeast) |
| UBE2V1 | ubiquitin-conjugating enzyme E2 variant 1 |

Example 6

Using the technique of Example 1, the biologically active nutrient for liver situations is identified. The relevant genes for this identification would include:

| Gene symbol | Description |
| --- | --- |
| AFP | alpha-fetoprotein |
| AGMAT | agmatine ureohydrolase (agmatinase) |
| AGTR1 | angiotensin II receptor, type 1 |
| ALB | albumin |
| ALDH2 | aldehyde dehydrogenase 2 family (mitochondrial) |
| ALDH3A1 | aldehyde dehydrogenase 3 family, memberA1 |
| ALDH9A1 | aldehyde dehydrogenase 9 family, member A1 |
| ALDOB | aldolase B, fructose-bisphosphate |
| ALPP | alkaline phosphatase, placental (Regan isozyme) |
| ANGPT2 | angiopoietin 2 |
| ANKH | ankylosis, progressive homolog (mouse) |
| ANPEP | alanyl (membrane) aminopeptidase |
| ASL | argininosuccinate lyase |
| ASS1 | argininosuccinate synthetase 1 |
| BMP6 | bone morphogenetic protein 6 |
| BMP8B | bone morphogenetic protein 8b |
| BTBD1 | BTB (POZ) domain containing 1 |
| BTD | biotinidase |
| CA2 | carbonic anhydrase II |
| CA3 | carbonic anhydrase III, muscle specific |
| CABIN1 | calcineurin binding protein 1 |
| CALR | calreticulin |

| Gene symbol | Description |
|---|---|
| CASP3 | caspase 3, apoptosis-related cysteine peptidase |
| CASP4 | caspase 4, apoptosis-related cysteine peptidase |
| CASP5 | caspase 5, apoptosis-related cysteine peptidase |
| CASP8 | caspase 8, apoptosis-related cysteine peptidase |
| CASP9 | caspase 9, apoptosis-related cysteine peptidase |
| CAT | catalase |
| CDH1 | cadherin 1, type 1, E-cadherin (epithelial) |
| CDH5 | cadherin 5, type 2 (vascular endothelium) |
| CDK7 | cyclin-dependent kinase 7 |
| CDKN1A | cyclin-dependent kinase inhibitor 1A (p21, Cip1) |
| CDKN2A | cyclin-dependent kinase inhibitor 2A (melanoma, p16, inhibits CDK4) |
| CDKN3 | cyclin-dependent kinase inhibitor 3 (CDK2-associated dual specificity phosphatase) |
| CLIC1 | chloride intracellular channel 1 |
| CP | ceruloplasmin (ferroxidase) |
| CPB1 | carboxypeptidase B1 (tissue) |
| CPD | carboxypeptidase D |
| CPE | carboxypeptidase E |
| CPS1 | carbamoyl-phosphate synthetase 1, mitochondrial |
| CPT1A | carnitine palmitoyltransferase 1A (liver) |
| CR1 | complement component (3b/4b) receptor 1 (Knops blood group) |
| CRABP1 | cellular retinoic acid binding protein 1 |
| CRAT | carnitine acetyltransferase |
| CREB3 | cAMP responsive element binding protein 3 |
| CREBBP | CREB binding protein (Rubinstein-Taybi syndrome) |
| CREBL1 | cAMP responsive element binding protein-like 1 |
| CYP17A1 | cytochrome P450, family 17, subfamily A, polypeptide 1 |
| CYP1A1 | cytochrome P450, family 1, subfamily A, polypeptide 1 |
| CYP1A2 | cytochrome P450, family 1, subfamily A, polypeptide 2 |
| CYP2A6 | cytochrome P450, family 2, subfamily A, polypeptide 6 |
| CYP2C19 | cytochrome P450, family 2, subfamily C, polypeptide 19 |
| CYP2C9 | cytochrome P450, family 2, subfamily C, polypeptide 9 |
| CYP2D6 | cytochrome P450, family 2, subfamily D, polypeptide 6 |
| CYP2E1 | cytochrome P450, family 2, subfamily E, polypeptide 1 |
| CYP3A4 | cytochrome P450, family 3, subfamily A, polypeptide 4 |
| CYP3A5 | cytochrome P450, family 3, subfamily A, polypeptide 5 |
| DCN | decorin |
| DCTD | dCMP deaminase |
| DPP4 | dipeptidyl-peptidase 4 (CD26, adenosine deaminase complexing protein 2) |
| DUOX1 | dual oxidase 1 |
| E2F1 | E2F transcription factor 1 |
| E4F1 | E4F transcription factor 1 |
| EGF | epidermal growth factor (beta-urogastrone) |
| EGFR | epidermal growth factor receptor (erythroblastic leukemia viral (v-erb-b) oncogene homolog, avian) |
| EGR2 | early growth response 2 (Krox-20 homolog, Drosophila) |
| EGR3 | early growth response 3 |
| ENG | endoglin (Osler-Rendu-Weber syndrome 1) |
| ENO1 | enolase 1, (alpha) |
| ESR1 | estrogen receptor 1 |
| ESR2 | estrogen receptor 2 (ER beta) |
| ESRRB | estrogen-related receptor beta |
| F10 | coagulation factor X |
| F8 | coagulation factor VIII, procoagulant component |
| FADD | Fas (TNFRSF6)-associated via death domain |
| FAH | fumarylacetoacetate hydrolase (fumarylacetoacetase) |
| FAP | fibroblast activation protein, alpha |
| FAS | Fas (TNF receptor superfamily, member 6) |
| FASLG | Fas ligand (TNF superfamily, member 6) |
| FASN | fatty acid synthase |
| FASTK | Fas-activated serine/threonine kinase |
| FBP2 | fructose-1,6-bisphosphatase 2 |
| FBXL2 | F-box and leucine-rich repeat protein 2 |
| FGL1 | fibrinogen-like 1 |
| FGL2 | fibrinogen-like 2 |
| FIGF | c-fos induced growth factor (vascular endothelial growth factor D) |
| FRY | furry homolog (Drosophila) |
| FTH1 | ferritin, heavy polypeptide 1 |
| G3BP1 | GTPase activating protein (SH3 domain) binding protein 1 |
| G6PD | glucose-6-phosphate dehydrogenase |
| GALE | UDP-galactose-4-epimerase |
| GAPDH | glyceraldehyde-3-phosphate dehydrogenase |
| GJB1 | gap junction protein, beta 1, 32 kDa |
| GLUD1 | glutamate dehydrogenase 1 |
| GLUL | glutamate-ammonia ligase (glutamine synthetase) |

-continued

| Gene symbol | Description |
| --- | --- |
| GOLGA4 | golgi autoantigen, golgin subfamily a, 4 |
| GOLM1 | golgi membrane protein 1 |
| GP2 | glycoprotein 2 (zymogen granule membrane) |
| GP6 | glycoprotein VI (platelet) |
| GPA33 | glycoprotein A33 (transmembrane) |
| GPC3 | glypican 3 |
| GPT | glutamic-pyruvate transaminase (alanine aminotransferase) |
| GPT2 | glutamic pyruvate transaminase (alanine aminotransferase) 2 |
| GPX1 | glutathione peroxidase 1 |
| GPX2 | glutathione peroxidase 2 (gastrointestinal) |
| GPX5 | glutathione peroxidase 5 (epididymal androgen-related protein) |
| GSR | glutathione reductase |
| GSTM1 | glutathione S-transferase M1 |
| GSTP1 | glutathione S-transferase pi 1 |
| GSTT1 | glutathione S-transferase theta 1 |
| GUSB | glucuronidase, beta |
| HBXIP | hepatitis B virus x interacting protein |
| HDAC1 | histone deacetylase 1 |
| HDDC2 | HD domain containing 2 |
| HIC1 | hypermethylated in cancer 1 |
| HNF4A | hepatocyte nuclear factor 4, alpha |
| HNRNPA1 | heterogeneous nuclear ribonucleoprotein A1 |
| HNRNPA2B1 | heterogeneous nuclear ribonucleoprotein A2/B1 |
| HNRNPC | heterogeneous nuclear ribonucleoprotein C (C1/C2) |
| ICAM1 | intercellular adhesion molecule 1 |
| ICAM3 | intercellular adhesion molecule 3 |
| IKBKB | inhibitor of kappa light polypeptide gene enhancer in B-cells, kinase beta |
| IKBKE | inhibitor of kappa light polypeptide gene enhancer in B-cells, kinase epsilon |
| IL10 | interleukin 10 |
| IL10RA | interleukin 10 receptor, alpha |
| IL10RB | interleukin 10 receptor, beta |
| IL12A | interleukin 12A (natural killer cell stimulatory factor 1, cytotoxic lymphocyte maturation factor 1, p35) |
| IL12B | interleukin 12B (natural killer cell stimulatory factor 2, cytotoxic lymphocyte maturation factor 2, p40) |
| IL12RB1 | interleukin 12 receptor, beta 1 |
| IL15 | interleukin 15 |
| IL18 | interleukin 18 (interferon-gamma-inducing factor) |
| IL18BP | interleukin 18 binding protein |
| IL18R1 | interleukin 18 receptor 1 |
| IL19 | interleukin 19 |
| IL1A | interleukin 1, alpha |
| IL1B | interleukin 1, beta |
| IL1R1 | interleukin 1 receptor, type I |
| IL1RAP | interleukin 1 receptor accessory protein |
| IL1RAPL2 | interleukin 1 receptor accessory protein-like 2 |
| IL1RL1 | interleukin 1 receptor-like 1 |
| IL1RN | interleukin 1 receptor antagonist |
| IL2 | interleukin 2 |
| IL20 | interleukin 20 |
| IL22 | interleukin 22 |
| IL28A | interleukin 28A (interferon, lambda 2) |
| IL2RA | interleukin 2 receptor, alpha |
| IL2RB | interleukin 2 receptor, beta |
| IL4 | interleukin 4 |
| IL4R | interleukin 4 receptor |
| IL6 | interleukin 6 (interferon, beta 2) |
| IL6R | interleukin 6 receptor |
| IL7 | interleukin 7 |
| IL7R | interleukin 7 receptor |
| IL8 | interleukin 8 |
| IL8RA | interleukin 8 receptor, alpha |
| IL8RB | interleukin 8 receptor, beta |
| ILF2 | interleukin enhancer binding factor 2, 45 kDa |
| ILF3 | interleukin enhancer binding factor 3, 90 kDa |
| ITGA4 | integrin, alpha 4 (antigen CD49D, alpha 4 subunit of VLA-4 receptor) |
| ITGAL | integrin, alpha L (antigen CD11A (p180), lymphocyte function-associated antigen 1; alpha polypeptide) |
| ITGB1 | integrin, beta 1 (fibronectin receptor, beta polypeptide, antigen CD29 includes MDF2, MSK12) |
| ITIH4 | inter-alpha (globulin) inhibitor H4 (plasma Kallikrein-sensitive glycoprotein) |
| ITPR2 | inositol 1,4,5-triphosphate receptor, type 2 |
| JAG1 | jagged 1 (Alagille syndrome) |
| JAK1 | Janus kinase 1 (a protein tyrosine kinase) |

-continued

| Gene symbol | Description |
|---|---|
| KHK | ketohexokinase (fructokinase) |
| LAMB2 | laminin, beta 2 (laminin S) |
| LARGE | like-glycosyltransferase |
| LCAT | lecithin-cholesterol acyltransferase |
| LCK | lymphocyte-specific protein tyrosine kinase |
| LCN1 | lipocalin 1 (tear prealbumin) |
| LCP1 | lymphocyte cytosolic protein 1 (L-plastin) |
| LDLR | low density lipoprotein receptor (familial hypercholesterolemia) |
| LECT2 | leukocyte cell-derived chemotaxin 2 |
| LEF1 | lymphoid enhancer-binding factor 1 |
| LEP | leptin |
| LEPR | leptin receptor |
| LSL | Leptin, serum levels of |
| LTA | lymphotoxin alpha (TNF superfamily, member 1) |
| LTB | lymphotoxin beta (TNF superfamily, member 3) |
| LTBP2 | latent transforming growth factor beta binding protein 2 |
| LTBR | lymphotoxin beta receptor (TNFR superfamily, member 3) |
| LTF | lactotransferrin |
| MAGEA1 | melanoma antigen family A, 1 (directs expression of antigen MZ2-E) |
| MAGEA4 | melanoma antigen family A, 4 |
| MAP2K4 | mitogen-activated protein kinase kinase 4 |
| MAP2K6 | mitogen-activated protein kinase kinase 6 |
| MAP2K7 | mitogen-activated protein kinase kinase 7 |
| MAP3K14 | mitogen-activated protein kinase kinase kinase 14 |
| MAP4K4 | mitogen-activated protein kinase kinase kinase kinase 4 |
| MAPK1 | mitogen-activated protein kinase 1 |
| MAPK10 | mitogen-activated protein kinase 10 |
| MAPK14 | mitogen-activated protein kinase 14 |
| MAPK8 | mitogen-activated protein kinase 8 |
| MARCKS | myristoylated alanine-rich protein kinase C substrate |
| MARCKSL1 | MARCKS-like 1 |
| MAT1A | methionine adenosyltransferase I, alpha |
| MAZ | MYC-associated zinc finger protein (purine-binding transcription factor) |
| MBL1P1 | mannose-binding lectin (protein A) 1, pseudogene 1 |
| MBL2 | mannose-binding lectin (protein C) 2, soluble (opsonic defect) |
| MBP | myelin basic protein |
| MCM2 | minichromosome maintenance complex component 2 |
| MCM7 | minichromosome maintenance complex component 7 |
| MCRS1 | microspherule protein 1 |
| MDM2 | Mdm2 p53 binding protein homolog (mouse) |
| MEMO1 | mediator of cell motility 1 |
| MET | met proto-oncogene (hepatocyte growth factor receptor) |
| MGAT3 | mannosyl (beta-1,4-)-glycoprotein beta-1,4-N-acetylglucosaminyltransferase |
| MGAT5 | mannosyl (alpha-1,6-)-glycoprotein beta-1,6-N-acetyl-glucosaminyltransferase |
| MGMT | O-6-methylguanine-DNA methyltransferase |
| NAGLU | N-acetylglucosaminidase, alpha- |
| NAT1 | N-acetyltransferase 1 (arylamine N-acetyltransferase) |
| NAT2 | N-acetyltransferase 2 (arylamine N-acetyltransferase) |
| NCL | nucleolin |
| NCOA6 | nuclear receptor coactivator 6 |
| NDRG1 | N-myc downstream regulated gene 1 |
| NFIL3 | nuclear factor, interleukin 3 regulated |
| NFKB1 | nuclear factor of kappa light polypeptide gene enhancer in B-cells 1 |
| NFKBIB | nuclear factor of kappa light polypeptide gene enhancer in B-cells inhibitor, beta |
| NFKBIL1 | nuclear factor of kappa light polypeptide gene enhancer in B-cells inhibitor-like 1 |
| NINJ1 | ninjurin 1 |
| NNMT | nicotinamide N-methyltransferase |
| NOS2A | nitric oxide synthase 2A (inducible, hepatocytes) |
| NOSTRIN | nitric oxide synthase trafficker |
| PAX5 | paired box 5 |
| PDCD1 | programmed cell death 1 |
| PDGFB | platelet-derived growth factor beta polypeptide (simian sarcoma viral (v-sis) oncogene homolog) |
| PDLIM3 | PDZ and LIM domain 3 |
| PDXP | pyridoxal (pyridoxine, vitamin B6) phosphatase |
| PI4KA | phosphatidylinositol 4-kinase, catalytic, alpha |
| PIAS1 | protein inhibitor of activated STAT, 1 |
| PIAS3 | protein inhibitor of activated STAT, 3 |
| PIK3R1 | phosphoinositide-3-kinase, regulatory subunit 1 (alpha) |
| PIN1 | peptidylprolyl cis/trans isomerase, NIMA-interacting 1 |
| PITX1 | paired-like homeodomain 1 |
| PNKD | paroxysmal nonkinesigenic dyskinesia |

-continued

| Gene symbol | Description |
|---|---|
| PPARA | peroxisome proliferator-activated receptor alpha |
| PPAT | phosphoribosyl pyrophosphate amidotransferase |
| PPIA | peptidylprolyl isomerase A (cyclophilin A) |
| PPIB | peptidylprolyl isomerase B (cyclophilin B) |
| PPIG | peptidylprolyl isomerase G (cyclophilin G) |
| PPM2C | protein phosphatase 2C, magnesium-dependent, catalytic subunit |
| PPP2R4 | protein phosphatase 2A activator, regulatory subunit 4 |
| PRDX2 | peroxiredoxin 2 |
| PRF1 | perforin 1 (pore forming protein) |
| PRKACA | protein kinase, cAMP-dependent, catalytic, alpha |
| PRKCB1 | protein kinase C, beta 1 |
| PRKCZ | protein kinase C, zeta |
| PRKG1 | protein kinase, cGMP-dependent, type I |
| PRL | prolactin |
| PRM1 | protamine 1 |
| PRMT1 | protein arginine methyltransferase 1 |
| PRSM2 | protease, metallo, 2 |
| PRSS1 | protease, serine, 1 (trypsin 1) |
| PRTN3 | proteinase 3 |
| PTBP1 | polypyrimidine tract binding protein 1 |
| PTBP2 | polypyrimidine tract binding protein 2 |
| PTEN | phosphatase and tensin homolog |
| PTGS1 | prostaglandin-endoperoxide synthase 1 (prostaglandin G/H synthase and cyclooxygenase) |
| PTGS2 | prostaglandin-endoperoxide synthase 2 (prostaglandin G/H synthase and cyclooxygenase) |
| PTMA | prothymosin, alpha |
| PTPLAD1 | protein tyrosine phosphatase-like A domain containing 1 |
| PTPN11 | protein tyrosine phosphatase, non-receptor type 11 |
| PTPN3 | protein tyrosine phosphatase, non-receptor type 3 |
| PTPRC | protein tyrosine phosphatase, receptor type, C |
| PTPRCAP | protein tyrosine phosphatase, receptor type, C-associated protein |
| PVR | poliovirus receptor |
| RELA | v-rel reticuloendotheliosis viral oncogene homolog A (avian) |
| REXO1L1 | REX1, RNA exonuclease 1 homolog (S. cerevisiae)-like 1 |
| RSAD2 | radical S-adenosyl methionine domain containing 2 |
| RSF1 | remodeling and spacing factor 1 |
| RXRA | retinoid X receptor, alpha |
| S100B | S100 calcium binding protein B |
| SCARB1 | scavenger receptor class B, member 1 |
| SCARB2 | scavenger receptor class B, member 2 |
| SCLY | selenocysteine lyase |
| SULT1A3 | sulfotransferase family, cytosolic, 1A, phenol-preferring, member 3 |
| SULT2B1 | sulfotransferase family, cytosolic, 2B, member 1 |
| SUOX | sulfite oxidase |
| TBK1 | TANK-binding kinase 1 |
| TBP | TATA box binding protein |
| TBX21 | T-box 21 |
| TCEA1 | transcription elongation factor A (SII), 1 |
| TCF3 | transcription factor 3 (E2A immunoglobulin enhancer binding factors E12/E47) |
| TDF | tumor differentiation factor |
| TERT | telomerase reverse transcriptase |
| TG | thyroglobulin |
| TGFA | transforming growth factor, alpha |
| TGFB1 | transforming growth factor, beta 1 |
| TGFB3 | transforming growth factor, beta 3 |
| TGFBR1 | transforming growth factor, beta receptor 1 |
| TGFBRAP1 | transforming growth factor, beta receptor associated protein 1 |
| TGIF1 | TGFB-induced factor homeobox 1 |
| THBS2 | thrombospondin 2 |
| THBS4 | thrombospondin 4 |
| THOC1 | THO complex 1 |
| THPO | thrombopoietin |
| THY1 | Thy-1 cell surface antigen |
| TK1 | thymidine kinase 1, soluble |
| TK2 | thymidine kinase 2, mitochondrial |
| TKT | transketolase |
| TOP1 | topoisomerase (DNA) I |
| TXN | thioredoxin |
| TXNIP | thioredoxin interacting protein |
| UBD | ubiquitin D |
| UBE2B | ubiquitin-conjugating enzyme E2B (RAD6 homolog) |
| UBE2E3 | ubiquitin-conjugating enzyme E2E 3 (UBC4/5 homolog, yeast) |
| UBE2K | ubiquitin-conjugating enzyme E2K (UBC1 homolog, yeast) |
| UBE2L3 | ubiquitin-conjugating enzyme E2L 3 |

| Gene symbol | Description |
|---|---|
| UBE3A | ubiquitin protein ligase E3A |
| UBQLN1 | ubiquilin 1 |
| UCK1 | uridine-cytidine kinase 1 |
| VDR | vitamin D (1,25-dihydroxyvitamin D3) receptor |
| VEGFA | vascular endothelial growth factor A |
| VWCE | von Willebrand factor C and EGF domains |
| WHSC2 | Wolf-Hirschhorn syndrome candidate 2 |
| XRCC1 | X-ray repair complementing defective repair in Chinese hamster cells 1 |

EXAMPLE 7

Using the technique of Example 1, the biologically active nutrient for anxiety syndromes is identified. The relevant genes for this identification would include:

| Gene symbol | Description |
|---|---|
| ABCA1 | ATP-binding cassette, sub-family A (ABC1), member 1 |
| ABCC9 | ATP-binding cassette, sub-family C (CFTR/MRP), member 9 |
| ADARB1 | adenosine deaminase, RNA-specific, B1 (RED1 homolog rat) |
| ADAT1 | adenosine deaminase, tRNA-specific 1 |
| ADCY10 | adenylate cyclase 10 (soluble) |
| ADCYAP1 | adenylate cyclase activating polypeptide 1 (pituitary) |
| ADM | adrenomedullin |
| ADORA1 | adenosine A1 receptor |
| ADORA2A | adenosine A2a receptor |
| ADORA3 | adenosine A3 receptor |
| ADRA1B | adrenergic, alpha-1B-, receptor |
| ADRBK1 | adrenergic, beta, receptor kinase 1 |
| AGT | angiotensinogen (serpin peptidase inhibitor, clade A, member 8) |
| AGTR1 | angiotensin II receptor, type 1 |
| ANK2 | ankyrin 2, neuronal |
| ANXA3 | annexin A3 |
| ANXA4 | annexin A4 |
| AP1G1 | adaptor-related protein complex 1, gamma 1 subunit |
| AP1G1 | adaptor-related protein complex 1, gamma 1 subunit |
| APBA1 | amyloid beta (A4) precursor protein-binding, family A, member 1 |
| APBA2 | amyloid beta (A4) precursor protein-binding, family A, member 2 |
| APBB1IP | amyloid beta (A4) precursor protein-binding, family B, member 1 interacting protein |
| ARCN1 | archain 1 |
| ARR3 | arrestin 3, retinal (X-arrestin) |
| ATP2A1 | ATPase, Ca++ transporting, cardiac muscle, fast twitch 1 |
| ATP2A2 | ATPase, Ca++ transporting, cardiac muscle, slow twitch 2 |
| ATP2A3 | ATPase, Ca++ transporting, ubiquitous |
| ATP4B | ATPase, H+/K+ exchanging, beta polypeptide |
| ATP6V1B1 | ATPase, H+ transporting, lysosomal 56/58 kDa, V1 subunit B1 |
| ATP8B1 | ATPase, class I, type 8B, member 1 |
| ATR | ataxia telangiectasia and Rad3 related |
| AVPR1A | arginine vasopressin receptor 1A |
| AVPR1B | arginine vasopressin receptor 1B |
| BDKRB2 | bradykinin receptor B2 |
| BDNF | brain-derived neurotrophic factor |
| BECN1 | beclin 1, autophagy related |
| BET1 | blocked early in transport 1 homolog (S. cerevisiae) |
| BET1L | blocked early in transport 1 homolog (S. cerevisiae)-like |
| CACNA1A | calcium channel, voltage-dependent, P/Q type, alpha 1A subunit |
| CACNA1A | calcium channel, voltage-dependent, P/Q type, alpha 1A subunit |
| CACNA1B | calcium channel, voltage-dependent, N type, alpha 1B subunit |
| CACNA1C | calcium channel, voltage-dependent, L type, alpha 1C subunit |
| CACNA1D | calcium channel, voltage-dependent, L type, alpha 1D subunit |
| CALB1 | calbindin 1, 28 kDa |
| CALCR | calcitonin receptor |
| CALM1 | calmodulin 1 (phosphorylase kinase, delta) |
| CALM3 | calmodulin 3 (phosphorylase kinase, delta) |
| CALR | calreticulin |
| CAMK2A | calcium/calmodulin-dependent protein kinase (CaM kinase) II alpha |
| CAMK2B | calcium/calmodulin-dependent protein kinase (CaM kinase) II beta |
| CAMK2G | calcium/calmodulin-dependent protein kinase (CaM kinase) II gamma |

-continued

| Gene symbol | Description |
|---|---|
| CAMK2G | calcium/calmodulin-dependent protein kinase (CaM kinase) II gamma |
| CANT1 | calcium activated nucleotidase 1 |
| CANX | calnexin |
| CAPN1 | calpain 1, (mu/l) large subunit |
| CASK | calcium/calmodulin-dependent serine protein kinase (MAGUK family) |
| CASR | calcium-sensing receptor (hypocalciuric hypercalcemia 1, severe neonatal hyperparathyroidism) |
| CAV1 | caveolin 1, caveolae protein, 22 kDa |
| CAV1 | caveolin 1, caveolae protein, 22 kDa |
| CAV2 | caveolin 2 |
| CCNB1 | cyclin B1 |
| CRH | corticotropin releasing hormone |
| CRHR1 | corticotropin releasing hormone receptor 1 |
| DNM1 | dynamin 1 |
| DRD5 | dopamine receptor D5 |
| EGR1 | early growth response 1 |
| EMP2 | epithelial membrane protein 2 |
| ERN1 | endoplasmic reticulum to nucleus signaling 1 |
| ERN2 | endoplasmic reticulum to nucleus signaling 2 |
| F2R | coagulation factor II (thrombin) receptor |
| F2RL1 | coagulation factor II (thrombin) receptor-like 1 |
| F2RL2 | coagulation factor II (thrombin) receptor-like 2 |
| FAS | Fas (TNF receptor superfamily, member 6) |
| FBP1 | fructose-1,6-bisphosphatase 1 |
| FBP2 | fructose-1,6-bisphosphatase 2 |
| FIG4 | FIG4 homolog (S. cerevisiae) |
| FLNA | filamin A, alpha (actin binding protein 280) |
| FLNB | filamin B, beta (actin binding protein 278) |
| FLNC | filamin C, gamma (actin binding protein 280) |
| FLOT1 | flotillin 1 |
| FLOT1 | flotillin 1 |
| GABBR1 | gamma-aminobutyric acid (GABA) B receptor, 1 |
| GABBR2 | gamma-aminobutyric acid (GABA) B receptor, 2 |
| GAL | galanin prepropeptide |
| GAP43 | growth associated protein 43 |
| GGA1 | golgi associated, gamma adaptin ear containing, ARF binding protein 1 |
| GHRL | ghrelin/obestatin prepropeptide |
| GJA8 | gap junction protein, alpha 8, 50 kDa |
| GLP1R | glucagon-like peptide 1 receptor |
| GNRHR | gonadotropin-releasing hormone receptor |
| GRM1 | glutamate receptor, metabotropic 1 |
| GRM5 | glutamate receptor, metabotropic 5 |
| GRM7 | glutamate receptor, metabotropic 7 |
| GRP | gastrin-releasing peptide |
| HCRTR1 | hypocretin (orexin) receptor 1 |
| HDAC5 | histone deacetylase 5 |
| HRH1 | histamine receptor H1 |
| HRH2 | histamine receptor H2 |
| HTR2A | 5-hydroxytryptamine (serotonin) receptor 2A |
| HTR2B | 5-hydroxytryptamine (serotonin) receptor 2B |
| HTR2C | 5-hydroxytryptamine (serotonin) receptor 2C |
| HTT | huntingtin |
| HTT | huntingtin |
| IGF1R | insulin-like growth factor 1 receptor |
| IHPK1 | inositol hexaphosphate kinase 1 |
| IHPK2 | inositol hexaphosphate kinase 2 |
| IHPK3 | inositol hexaphosphate kinase 3 |
| IL2 | interleukin 2 |
| IL6 | interleukin 6 (interferon, beta 2) |
| IMPA2 | inositol(myo)-1(or 4)-monophosphatase 2 |
| IMPAD1 | inositol monophosphatase domain containing 1 |
| INPP1 | inositol polyphosphate-1-phosphatase |
| INPP3 | inositol polyphosphate-3-phosphatase |
| INPP4A | inositol polyphosphate-4-phosphatase, type I, 107 kDa |
| INPP4B | inositol polyphosphate-4-phosphatase, type II, 105 kDa |
| INPP5A | inositol polyphosphate-5-phosphatase, 40 kDa |
| INPP5B | inositol polyphosphate-5-phosphatase, 75 kDa |
| INPP5C | inositol polyphosphate-5-phosphatase, 120 kDa |
| INPP5D | inositol polyphosphate-5-phosphatase, 145 kDa |
| INPP5E | inositol polyphosphate-5-phosphatase, 72 kDa |
| INPP5F | inositol polyphosphate-5-phosphatase F |
| INPPL1 | inositol polyphosphate phosphatase-like 1 |
| INSR | insulin receptor |
| ISYNA1 | myo-inositol 1-phosphate synthase A1 |
| ITPK1 | inositol 1,3,4-triphosphate 5/6 kinase |
| ITPKA | inositol 1,4,5-trisphosphate 3-kinase A |

-continued

| Gene symbol | Description |
|---|---|
| ITPKB | inositol 1,4,5-trisphosphate 3-kinase B |
| ITPKC | inositol 1,4,5-trisphosphate 3-kinase C |
| ITPR1 | inositol 1,4,5-triphosphate receptor, type 1 |
| ITPR2 | inositol 1,4,5-triphosphate receptor, type 2 |
| ITPR3 | inositol 1,4,5-triphosphate receptor, type 3 |
| JAK1 | Janus kinase 1 (a protein tyrosine kinase) |
| JAK2 | Janus kinase 2 (a protein tyrosine kinase) |
| KCNA2 | potassium voltage-gated channel, shaker-related subfamily, member 2 |
| KCNB1 | potassium voltage-gated channel, Shab-related subfamily, member 1 |
| KCND3 | potassium voltage-gated channel, Shal-related subfamily, member 3 |
| KCNJ6 | potassium inwardly-rectifying channel, subfamily J, member 6 |
| KCNMA1 | potassium large conductance calcium-activated channel, subfamily M, alpha member 1 |
| KIF5B | kinesin family member 5B |
| LHB | luteinizing hormone beta polypeptide |
| LHCGR | luteinizing hormone/choriogonadotropin receptor |
| MARCH2 | membrane-associated ring finger (C3HC4) 2 |
| MINPP1 | multiple inositol polyphosphate histidine phosphatase, 1 |
| MIOX | myo-inositol oxygenase |
| MMP14 | matrix metallopeptidase 14 (membrane-inserted) |
| MMP17 | matrix metallopeptidase 17 (membrane-inserted) |
| MMP25 | matrix metallopeptidase 25 |
| MPP2 | membrane protein, palmitoylated 2 (MAGUK p55 subfamily member 2) |
| MPP7 | membrane protein, palmitoylated 7 (MAGUK p55 subfamily member 7) |
| MRC1 | mannose receptor, C type 1 |
| MRPS6 | mitochondrial ribosomal protein S6 |
| MRVI1 | murine retrovirus integration site 1 homolog |
| MS4A14 | membrane-spanning 4-domains, subfamily A, member 14 |
| MTHFD2L | methylenetetrahydrofolate dehydrogenase (NADP+ dependent) 2-like |
| NAGA | N-acetylgalactosaminidase, alpha- |
| NAPA | N-ethylmaleimide-sensitive factor attachment protein, alpha |
| NAPB | N-ethylmaleimide-sensitive factor attachment protein, beta |
| NAPG | N-ethylmaleimide-sensitive factor attachment protein, gamma |
| NFAT5 | nuclear factor of activated T-cells 5, tonicity-responsive |
| NFATC1 | nuclear factor of activated T-cells, cytoplasmic, calcineurin-dependent 1 |
| NFKB1 | nuclear factor of kappa light polypeptide gene enhancer in B-cells 1 |
| NMBR | neuromedin B receptor |
| NMUR1 | neuromedin U receptor 1 |
| NMUR2 | neuromedin U receptor 2 |
| NOLC1 | nucleolar and coiled-body phosphoprotein 1 |
| NPY | neuropeptide Y |
| NTS | neurotensin |
| NTSR1 | neurotensin receptor 1 (high affinity) |
| OR4D2 | olfactory receptor, family 4, subfamily D, member 2 |
| OXT | oxytocin, prepropeptide |
| OXTR | oxytocin receptor |
| PDE2A | phosphodiesterase 2A, cGMP-stimulated |
| PDE3B | phosphodiesterase 3B, cGMP-inhibited |
| PDE4D | phosphodiesterase 4D, cAMP-specific (phosphodiesterase E3 dunce homolog, Drosophila) |
| PDPK1 | 3-phosphoinositide dependent protein kinase-1 |
| PI4K2A | phosphatidylinositol 4-kinase type 2 alpha |
| PI4K2B | phosphatidylinositol 4-kinase type 2 beta |
| PI4KA | phosphatidylinositol 4-kinase, catalytic, alpha |
| PI4KAP2 | phosphatidylinositol 4-kinase, catalytic, alpha pseudogene 2 |
| PI4KB | phosphatidylinositol 4-kinase, catalytic, beta |
| PIB5PA | phosphatidylinositol (4,5) bisphosphate 5-phosphatase, A |
| PIGA | phosphatidylinositol glycan anchor biosynthesis, class A |
| PIGC | phosphatidylinositol glycan anchor biosynthesis, class C |
| PIGH | phosphatidylinositol glycan anchor biosynthesis, class H |
| PIGL | phosphatidylinositol glycan anchor biosynthesis, class L |
| PIGP | phosphatidylinositol glycan anchor biosynthesis, class P |
| PIGQ | phosphatidylinositol glycan anchor biosynthesis, class Q |
| PIGT | phosphatidylinositol glycan anchor biosynthesis, class T |
| PIGW | phosphatidylinositol glycan anchor biosynthesis, class W |
| PIGZ | phosphatidylinositol glycan anchor biosynthesis, class Z |
| PIK3C2A | phosphoinositide-3-kinase, class 2, alpha polypeptide |
| PIK3C2B | phosphoinositide-3-kinase, class 2, beta polypeptide |
| PIK3C2G | phosphoinositide-3-kinase, class 2, gamma polypeptide |
| PIK3C3 | phosphoinositide-3-kinase, class 3 |
| PIK3CA | phosphoinositide-3-kinase, catalytic, alpha polypeptide |
| PIK3CB | phosphoinositide-3-kinase, catalytic, beta polypeptide |
| PIK3CD | phosphoinositide-3-kinase, catalytic, delta polypeptide |
| PIK3CG | phosphoinositide-3-kinase, catalytic, gamma polypeptide |
| PIK3R1 | phosphoinositide-3-kinase, regulatory subunit 1 (alpha) |
| PIK3R2 | phosphoinositide-3-kinase, regulatory subunit 2 (beta) |
| PIK3R3 | phosphoinositide-3-kinase, regulatory subunit 3 (gamma) |
| PIP4K2A | phosphatidylinositol-5-phosphate 4-kinase, type II, alpha |

-continued

| Gene symbol | Description |
|---|---|
| PIP4K2B | phosphatidylinositol-5-phosphate 4-kinase, type II, beta |
| PIP4K2C | phosphatidylinositol-5-phosphate 4-kinase, type II, gamma |
| PIP5K1A | phosphatidylinositol-4-phosphate 5-kinase, type I, alpha |
| PIP5K1B | phosphatidylinositol-4-phosphate 5-kinase, type I, beta |
| PIP5K1C | phosphatidylinositol-4-phosphate 5-kinase, type I, gamma |
| PIP5K3 | phosphatidylinositol-3-phosphate/phosphatidylinositol 5-kinase, type III |
| PIP5KL1 | phosphatidylinositol-4-phosphate 5-kinase-like 1 |
| PITPNA | phosphatidylinositol transfer protein, alpha |
| PITPNM1 | phosphatidylinositol transfer protein, membrane-associated 1 |
| PLCB1 | phospholipase C, beta 1 (phosphoinositide-specific) |
| PLCB2 | phospholipase C, beta 2 |
| PLCB3 | phospholipase C, beta 3 (phosphatidylinositol-specific) |
| PLCB4 | phospholipase C, beta 4 |
| PLCD1 | phospholipase C, delta 1 |
| PLCD3 | phospholipase C, delta 3 |
| PLCD4 | phospholipase C, delta 4 |
| PLCE1 | phospholipase C, epsilon 1 |
| PLCG1 | phospholipase C, gamma 1 |
| PLCG2 | phospholipase C, gamma 2 (phosphatidylinositol-specific) |
| PLCH1 | phospholipase C, eta 1 |
| PLCH2 | phospholipase C, eta 2 |
| PLCL1 | phospholipase C-like 1 |
| PLCZ1 | phospholipase C, zeta 1 |
| PLD1 | phospholipase D1, phosphatidylcholine-specific |
| PLSCR1 | phospholipid scramblase 1 |
| PMM1 | phosphomannomutase 1 |
| PSEN1 | presenilin 1 |
| PSEN1 | presenilin 1 |
| PSEN2 | presenilin 2 (Alzheimer disease 4) |
| PTGDR | prostaglandin D2 receptor (DP) |
| PTGFR | prostaglandin F receptor (FP) |
| PTH | parathyroid hormone |
| PTHLH | parathyroid hormone-like hormone |
| PTHR1 | parathyroid hormone receptor 1 |
| PTK2B | PTK2B protein tyrosine kinase 2 beta |
| SCNN1A | sodium channel, nonvoltage-gated 1 alpha |
| SCNN1B | sodium channel, nonvoltage-gated 1, beta |
| SCNN1G | sodium channel, nonvoltage-gated 1, gamma |
| SDC1 | syndecan 1 |
| SDC2 | syndecan 2 |
| SDC4 | syndecan 4 |
| SEC1 | alpha(1,2) fucosyltransferase pseudogene |
| SEPT2 | septin 2 |
| SEPT5 | septin 5 |
| SFT2D3 | SFT2 domain containing 3 |
| SGK3 | serum/glucocorticoid regulated kinase family, member 3 |
| SHPK | sedoheptulokinase |
| SI | sucrase-isomaltase (alpha-glucosidase) |
| SLC1A1 | solute carrier family 1 (neuronal/epithelial high affinity glutamate transporter, system Xag), member 1 |
| SLC2A13 | solute carrier family 2 (facilitated glucose transporter), member 13 |
| SLC2A4 | solute carrier family 2 (facilitated glucose transporter), member 4 |
| SLC2A6 | solute carrier family 2 (facilitated glucose transporter), member 6 |
| SLC4A4 | solute carrier family 4, sodium bicarbonate cotransporter, member 4 |
| SLC5A11 | solute carrier family 5 (sodium/glucose cotransporter), member 11 |
| SLC5A3 | solute carrier family 5 (inositol transporters), member 3 |
| SLC5A6 | solute carrier family 5 (sodium-dependent vitamin transporter), member 6 |
| SLC6A1 | solute carrier family 6 (neurotransmitter transporter, GABA), member 1 |
| SLC6A2 | solute carrier family 6 (neurotransmitter transporter, noradrenalin), member 2 |
| SLC6A3 | solute carrier family 6 (neurotransmitter transporter, dopamine), member 3 |
| SLC6A4 | solute carrier family 6 (neurotransmitter transporter, serotonin), member 4 |
| SLC6A5 | solute carrier family 6 (neurotransmitter transporter, glycine), member 5 |
| SLC6A9 | solute carrier family 6 (neurotransmitter transporter, glycine), member 9 |
| SLC8A1 | solute carrier family 8 (sodium/calcium exchanger), member 1 |
| SMG1 | PI-3-kinase-related kinase SMG-1 |
| SMPD1 | sphingomyelin phosphodiesterase 1, acid lysosomal |
| SMPD2 | sphingomyelin phosphodiesterase 2, neutral membrane (neutral sphingomyelinase) |
| SORD | sorbitol dehydrogenase |
| STX10 | syntaxin 10 |
| STX11 | syntaxin 11 |
| STX12 | syntaxin 12 |
| STX16 | syntaxin 16 |
| STX17 | syntaxin 17 |
| STX18 | syntaxin 18 |
| STX19 | syntaxin 19 |
| STX1A | syntaxin 1A (brain) |

-continued

| Gene symbol | Description |
|---|---|
| STX1B | syntaxin 1B |
| STX2 | syntaxin 2 |
| STX3 | syntaxin 3 |
| STX4 | syntaxin 4 |
| STX5 | syntaxin 5 |
| STX6 | syntaxin 6 |
| STX7 | syntaxin 7 |
| STX8 | syntaxin 8 |
| STXBP1 | syntaxin binding protein 1 |
| STXBP2 | syntaxin binding protein 2 |
| STXBP3 | syntaxin binding protein 3 |
| STXBP4 | syntaxin binding protein 4 |
| STXBP5 | syntaxin binding protein 5 (tomosyn) |
| STXBP5L | syntaxin binding protein 5-like |
| STXBP6 | syntaxin binding protein 6 (amisyn) |
| SV2B | synaptic vesicle glycoprotein 2B |
| SYCN | syncollin |
| SYN1 | synapsin I |
| SYP | synaptophysin |
| SYT1 | synaptotagmin I |
| SYT1 | synaptotagmin I |
| SYT2 | synaptotagmin II |
| SYT3 | synaptotagmin III |
| SYTL4 | synaptotagmin-like 4 |
| TAC1 | tachykinin, precursor 1 |
| TACR1 | tachykinin receptor 1 |
| TACR2 | tachykinin receptor 2 |
| TACR3 | tachykinin receptor 3 |
| TPTE | transmembrane phosphatase with tensin homology |
| TPTE2 | transmembrane phosphoinositide 3-phosphatase and tensin homolog 2 |
| TRAF2 | TNF receptor-associated factor 2 |
| TRAF6 | TNF receptor-associated factor 6 |
| TRH | thyrotropin-releasing hormone |
| TRHR | thyrotropin-releasing hormone receptor |
| TSHR | thyroid stimulating hormone receptor |
| TSPAN4 | tetraspanin 4 |
| TXK | TXK tyrosine kinase |
| TXLNA | taxilin alpha |
| TXLNB | taxilin beta |
| TXNDC4 | thioredoxin domain containing 4 (endoplasmic reticulum) |
| TYK2 | tyrosine kinase 2 |
| TYRP1 | tyrosinase-related protein 1 |
| VAMP1 | vesicle-associated membrane protein 1 (synaptobrevin 1) |
| VAMP2 | vesicle-associated membrane protein 2 (synaptobrevin 2) |
| VAMP3 | vesicle-associated membrane protein 3 (cellubrevin) |
| VAMP7 | vesicle-associated membrane protein 7 |
| VAMP8 | vesicle-associated membrane protein 8 (endobrevin) |
| VAPA | VAMP (vesicle-associated membrane protein)-associated protein A, 33 kDa |
| VAPB | VAMP (vesicle-associated membrane protein)-associated protein B and C |
| VCL | vinculin |
| VCP | valosin-containing protein |
| VDAC1 | voltage-dependent anion channel 1 |
| VEGFA | vascular endothelial growth factor A |
| VIM | vimentin |
| VNN1 | vanin 1 |
| VNN2 | vanin 2 |
| WNT2 | wingless-type MMTV integration site family member 2 |

Example 8

Using the technique of Example 1, the biologically active nutrient for obesity is identified. The relevant genes for this identification would include:

| Gene symbol | Description |
|---|---|
| ACACA | acetyl-Coenzyme A carboxylase alpha |
| ACACB | acetyl-Coenzyme A carboxylase beta |
| ACTG1 | actin, gamma 1 |

-continued

| Gene symbol | Description |
|---|---|
| ADIPOQ | adiponectin, C1Q and collagen domain containing |
| ADIPOR1 | adiponectin receptor 1 |
| ADIPOR2 | adiponectin receptor 2 |
| ADRB2 | adrenergic, beta-2-, receptor, surface |
| ADRB3 | adrenergic, beta-3-, receptor |
| AGRP | agouti related protein homolog (mouse) |
| AKT1 | v-akt murine thymoma viral oncogene homolog 1 |
| ANGPTL4 | angiopoietin-like 4 |
| APLN | apelin |

-continued

| Gene symbol | Description |
|---|---|
| APOA4 | apolipoprotein A-IV |
| APOD | apolipoprotein D |
| APOM | apolipoprotein M |
| AR | androgen receptor (dihydrotestosterone receptor; testicular feminization; spinal and bulbar muscular atrophy; Kennedy disease) |
| BDNF | brain-derived neurotrophic factor |
| BIRC5 | baculoviral IAP repeat-containing 5 (survivin) |
| C1QTNF3 | C1q and tumor necrosis factor related protein 3 |
| CAQ5 | Circulating adiponectin QTL on chromosome 5 |
| CARTPT | CART prepropeptide |
| CCK | cholecystokinin |
| CCND1 | cyclin D1 |
| CEBPA | CCAAT/enhancer binding protein (C/EBP), alpha |
| CGB5 | chorionic gonadotropin, beta polypeptide 5 |
| CLU | clusterin |
| CNTF | ciliary neurotrophic factor |
| CNTFR | ciliary neurotrophic factor receptor |
| COL1A1 | collagen, type I, alpha 1 |
| CPT1B | carnitine palmitoyltransferase 1B (muscle) |
| CPT2 | carnitine palmitoyltransferase II |
| CREB1 | cAMP responsive element binding protein 1 |
| CRHR2 | corticotropin releasing hormone receptor 2 |
| CRP | C-reactive protein, pentraxin-related |
| CTGF | connective tissue growth factor |
| CYP19A1 | cytochrome P450, family 19, subfamily A, polypeptide 1 |
| DGAT1 | diacylglycerol O-acyltransferase homolog 1 (mouse) |
| DGKZ | diacylglycerol kinase, zeta 104 kDa |
| DRD2 | dopamine receptor D2 |
| EDN1 | endothelin 1 |
| EPHA3 | EPH receptor A3 |
| ESR1 | estrogen receptor 1 |
| FAAH | fatty acid amide hydrolase |
| FABP7 | fatty acid binding protein 7, brain |
| FASN | fatty acid synthase |
| FFAR3 | free fatty acid receptor 3 |
| FTO | fat mass and obesity associated |
| GALP | galanin-like peptide |
| GCG | glucagon |
| GCKR | glucokinase (hexokinase 4) regulator |
| GH1 | growth hormone 1 |
| GHR | growth hormone receptor |
| GHRL | ghrelin/obestatin prepropeptide |
| GHSR | growth hormone secretagogue receptor |
| GNRH1 | gonadotropin-releasing hormone 1 (luteinizing-releasing hormone) |
| GNRH2 | gonadotropin-releasing hormone 2 |
| GPLD1 | glycosylphosphatidylinositol specific phospholipase D1 |
| GRB2 | growth factor receptor-bound protein 2 |
| GRIP1 | glutamate receptor interacting protein 1 |
| GRLF1 | glucocorticoid receptor DNA binding factor 1 |
| GRP | gastrin-releasing peptide |
| H6PD | hexose-6-phosphate dehydrogenase (glucose 1-dehydrogenase) |
| HAMP | hepcidin antimicrobial peptide |
| HCRT | hypocretin (orexin) neuropeptide precursor |
| HCRTR1 | hypocretin (orexin) receptor 1 |
| HCRTR2 | hypocretin (orexin) receptor 2 |
| HK2 | hexokinase 2 |
| HSD11B1 | hydroxysteroid (11-beta) dehydrogenase 1 |
| HTR2C | 5-hydroxytryptamine (serotonin) receptor 2C |
| IAPP | islet amyloid polypeptide |
| IGF1 | insulin-like growth factor 1 (somatomedin C) |
| IGF1R | insulin-like growth factor 1 receptor |
| IGFBP1 | insulin-like growth factor binding protein 1 |
| IGFBP2 | insulin-like growth factor binding protein 2, 36 kDa |
| IGFBP3 | insulin-like growth factor binding protein 3 |
| IGFBP4 | insulin-like growth factor binding protein 4 |
| IGHJ1 | immunoglobulin heavy joining 1 |
| INS | insulin |
| INSR | insulin receptor |
| IRS1 | insulin receptor substrate 1 |
| IRS2 | insulin receptor substrate 2 |
| IRS4 | insulin receptor substrate 4 |
| ITLN1 | intelectin 1 (galactofuranose binding) |
| JAK1 | Janus kinase 1 (a protein tyrosine kinase) |
| JAK2 | Janus kinase 2 (a protein tyrosine kinase) |
| KAT5 | K(lysine) acetyltransferase 5 |
| KISS1 | KiSS-1 metastasis-suppressor |
| KISS1R | KISS1 receptor |
| LEP | leptin |
| LEPR | leptin receptor |
| LEPROT | leptin receptor overlapping transcript |
| LEPROTL1 | leptin receptor overlapping transcript-like 1 |
| LMNA | lamin A/C |
| LPA | lipoprotein, Lp(a) |
| LPIN3 | lipin 3 |
| LRP2 | low density lipoprotein-related protein 2 |
| LRP8 | low density lipoprotein receptor-related protein 8, apolipoprotein e receptor |
| LSL | Leptin, serum levels of |
| MC2R | melanocortin 2 receptor (adrenocorticotropic hormone) |
| MC4R | melanocortin 4 receptor |
| MC5R | melanocortin 5 receptor |
| MCHR1 | melanin-concentrating hormone receptor 1 |
| MDK | midkine (neurite growth-promoting factor 2) |
| MICE | MHC class I polypeptide-related sequence E |
| MUC3A | mucin 3A, cell surface associated |
| MUC4 | mucin 4, cell surface associated |
| NAMPT | nicotinamide phosphoribosyltransferase |
| NGF | nerve growth factor (beta polypeptide) |
| NMB | neuromedin B |
| NOS3 | nitric oxide synthase 3 (endothelial cell) |
| NOX4 | NADPH oxidase 4 |
| NPY | neuropeptide Y |
| NPY1R | neuropeptide Y receptor Y1 |
| NPY5R | neuropeptide Y receptor Y5 |
| NR3C1 | nuclear receptor subfamily 3, group C, member 1 |
| NTS | neurotensin |
| PDE3A | phosphodiesterase 3A, cGMP-inhibited |
| PDE3B | phosphodiesterase 3B, cGMP-inhibited |
| PELP1 | proline, glutamate and leucine rich protein 1 |
| PMCH | pro-melanin-concentrating hormone |
| POMC | proopiomelanocortin |
| PPARG | peroxisome proliferator-activated receptor gamma |
| PPYR1 | pancreatic polypeptide receptor 1 |
| PRL | prolactin |
| PRLR | prolactin receptor |
| PSMB8 | proteasome (prosome, macropain) subunit, beta type, 8 (large multifunctional peptidase 7) |
| PSMC6 | proteasome (prosome, macropain) 26S subunit, ATPase, 6 |
| PTGDS | prostaglandin D2 synthase 21 kDa (brain) |
| PYY | peptide YY |
| RETN | resistin |
| RNY5 | RNA, Ro-associated Y5 |
| SCD | stearoyl-CoA desaturase (delta-9-desaturase) |
| SCD5 | stearoyl-CoA desaturase 5 |
| SELE | selectin E |
| SLEP1 | Serum leptin concentration QTL 1 |
| SLEP2 | Serum leptin concentration QTL 2 |
| SLEP3 | Serum leptin concentration QTL 3 |
| SMAD2 | SMAD family member 2 |
| SMAD3 | SMAD family member 3 |
| SNCG | synuclein, gamma (breast cancer-specific protein 1) |
| SNX4 | sorting nexin 4 |
| SNX6 | sorting nexin 6 |
| SOAT1 | sterol O-acyltransferase (acyl-Coenzyme A: cholesterol acyltransferase) 1 |
| SRA1 | steroid receptor RNA activator 1 |
| SREBF1 | sterol regulatory element binding transcription factor 1 |
| STAT3 | signal transducer and activator of transcription 3 |
| STAT5A | signal transducer and activator of transcription 5A |
| STAT5B | signal transducer and activator of transcription 5B |
| TRH | thyrotropin-releasing hormone |
| TTF2 | transcription termination factor, RNA polymerase II |
| UBC | ubiquitin C |
| UCN | urocortin |
| UCP1 | uncoupling protein 1 (mitochondrial, proton carrier) |
| UCP2 | uncoupling protein 2 (mitochondrial, proton carrier) |
| UCP3 | uncoupling protein 3 (mitochondrial, proton carrier) |
| VDR | vitamin D (1,25- dihydroxyvitamin D3) receptor |
| VEGFA | vascular endothelial growth factor A |

-continued

| Gene symbol | Description |
|---|---|
| VLDLR | very low density lipoprotein receptor |
| ZBTB17 | zinc finger and BTB domain containing 17 |
| ZNF318 | zinc finger protein 318 |

Example 9

The method to assess the biologically active nutrient to include in the diet based on the differential gene expressions of samples from healthy and unhealthy animals of different genotypes is reported.

In the example, the effect of curcumin or andrographolide administrations on arthrosis of German Shepherd dogs is described. In the example, the differential gene expressions profiles between healthy and affected dogs is evaluated by means of microarray. The exposure of cells of affected dogs to biologically active nutrients with known ant inflammatory activity allows the identification of the more appropriate biologically active nutrients to include in the diet.

Synovial fluid from the knee of 10 dogs affected by arthrosis (age 4-6 years) and 10 healthy dogs (age 5-7 years) were sampled. Synovial fluid was centrifuged at 10000 rpm for 30 minutes and cell pellets recovered and store at −80 degrees C. until analysis.

Total RNA of cells was extracted using phenol/guanidine HCl reagents (Trizol, Invitrogen). RNA quality integrity was analysed using the Agilent 2100 Bioanalyser (Agilent Technologies) of the sample. The samples determined to have no, or minimal, loss of integrity and thus were considered suitable for use in experiments. mRNA was amplified for each sample, starting with 500 ng total RNA using a commercially available kit (Ambion T7 MEGAscript high yield transcription kit, Ambion). The mRNA was quantified using a spectrophotometer. mRNA was directly reverse transcribed to cDNA from 25 μg of total RNA using the Superscript indirect cDNA labeling Core kit (Invitrogen, Milan, Italy).

Two micrograms of cDNA were labelled with Cyanine-3dCTP (Cy3) or Cyanine-5dCTP (Cy5) fluorochromes using the cDNA labeling purification module kit (Invitrogen, Milan, Italy). Samples were hybridised to a canine specific, whole genome 44k spot 60mer oligonucleotide (Agilent Technologies). The labelled cDNA was appropriately coupled and used for competitive hybridization on the same microarray at 42° C. for 16 h. Fluorescence incorporation was determined using a spectrophotometer. The relative intensity of labelled cDNA in was acquired with ScanArray LITE scanner (PerkinElmer Life Sciences, Inc).

Expression data were then exported into Excel 2007 and processed with SAM software; comparison between groups was achieved using paired student's t tests. Comparisons of the number of genes up-or down-regulated in both the normal and affected cells were made using Chi squared analysis. Correction for multiple hypothesis testing was performed using the false discovery rate (FDR).

For each of the 10 individual healthy and 10 individual unhealthy dogs affected with arthrosis, the same set of 21 genes was determined to be differently expressed between the cartilage cells of both the healthy and unhealthy dogs. Two were down-regulated and 19 were up-regulated (Table 1).

| Gene symbol | Gene name | Fold change Individual Unhealthy Dogs | |
|---|---|---|---|
| | | Mean | s.e. |
| ACTB | Beta actin | 3.8 | 0.1 |
| ACTR3 | Actin-related protein 3 | 0.3 | 0.1 |
| ADK | Adenosine kinase, transcript variant 3 | 3.6 | 0.2 |
| ANKRD10 | Ankyrin repeat domain 10 | 5.2 | 0.9 |
| CAV1 | Caveolin 1 | 4.8 | 0.6 |
| CDH11 | Cadherin 11, type 2, OB-cadherin | 6.9 | 0.9 |
| COL3A1 | Collagen 3, alpha 1 | 9.5 | 1.7 |
| COX1 | Cycloxygenase-21 | 0.8 | 0.2 |
| COX2 | Cycloxygenase-2 | 23.0 | 2.8 |
| IGFBP7 | IGFBP7 Insulin-like growth factor binding protein 7 | 3.7 | 0.8 |
| IL2 | Interlukin 2 | 3.0 | 0.7 |
| MMP2 | matrix metallopeptidase 2 | 10.0 | 2.1 |
| NOS2 | nitric oxide synthase 2A | 0.2 | 0.1 |
| PTGS-2 | prostaglandin-endoperoxide synthase | 1.2 | 0.3 |
| SPARC | Osteonectin | 6.3 | 1.1 |
| STMN1 | Stathmin 1 | 6.2 | 0.6 |
| TIMP1 | TIMP metallopeptidase inhibitor 1 | 6.2 | 0.4 |
| TIMP2 | TIMP metallopeptidase inhibitor 2 | 2.0 | 0.1 |
| TNF-a | tumor necrosis factor alpha | 10.0 | 1.1 |
| TUBA | Alpha-tubulin | 4.7 | 0.7 |
| TUBB | Beta-tublin | 4.8 | 0.5 |

The comparison between the healthy and affected dogs indicated that each of the affected unhealthy dogs underwent degenerative and inflammatory processes.

Searching within the nutrient data set for biologically active nutrients with anti-arthritic and anti-inflammatory properties identified curcumin and androgropholide as the appropriated compositions. The cartilage cells of individual affected unhealthy dogs were cultured in vitro with 0, or 60 mg/l of curcumin or androgropholide for 6 hours. At the end of the incubation, these cartilage cells from individual affected dogs were washed and used for RNA extraction. For the microarray analysis, co-hybridisation of the RNA from 0 and 60 mg/l was conducted, using the material and the methods described previously.

Table 2

The table below reports the mean fold change in gene expression of two biologically active nutrients, namely curcumin and andrographolide. As can be seen, the andrographolide possesses an anti-inflammatory activity, but does not exactly match the regulation of all the genes up- or down-regulated in the individual affected unhealthy cartilage cells. Instead, curcumin completely satisfies these requirements, so that the food composition is designed to include curcumin. The dose to be added to the food or the nutrient composition is computed using literature data, which indicates a dose of 4 mg/kg body weight for either curcumin or andrographolide.

| | FOLD CHANGE OF GENE EXPRESSION | | | | NET EFFECT OF THE NBC ON FOLD CHANGE | | | |
|---|---|---|---|---|---|---|---|---|
| Gene | Curcumin | | Androgrpholide | | Curcumin | | Androgrpholide | |
| Name | mean | s.d. | mean | s.d. | mean | s.d. | mean | s.d. |
| ACTB | −5.0 | 0.1 | −1.0 | 0.1 | −1.2 | 0.1 | 2.8 | 0.1 |
| ACTR3 | −1.0 | 0.2 | 1.0 | 1 | −4.0 | 0.2 | 1.3 | 0.7 |
| ADK | −4.3 | 0.1 | 0.0 | 0.1 | −1.4 | 0.2 | 3.6 | 0.2 |
| ANKRD-10 | −7.0 | 1.1 | 0.0 | 0.8 | −1.8 | 1.0 | 5.2 | 0.9 |

-continued

| Gene Name | FOLD CHANGE OF GENE EXPRESSION | | | | NET EFFECT OF THE NBC ON FOLD CHANGE | | | |
|---|---|---|---|---|---|---|---|---|
| | Curcumin | | Androgrpholide | | Curcumin | | Androgrpholide | |
| | mean | s.d. | mean | s.d. | mean | s.d. | mean | s.d. |
| CAV1 | −3.0 | 0.3 | 0.0 | 0.3 | 1.8 | 0.5 | 4.8 | 0.5 |
| CDH11 | −6.0 | 1.1 | −1.0 | 0.1 | 0.9 | 1.0 | 5.9 | 0.6 |
| COL3A1 | −6.0 | 0.6 | −2.0 | 0.2 | 3.5 | 1.3 | 7.5 | 1.2 |
| COX1 | −1.0 | 0.3 | 0.0 | 0.1 | −0.2 | 0.3 | 0.8 | 0.2 |
| COX2 | −15.0 | 2 | 0.0 | 0.2 | 8.0 | 2.4 | 23.0 | 2.0 |
| IGFBP7 | −1.5 | 0.4 | −2.0 | 0.2 | 2.2 | 0.6 | 1.7 | 0.6 |
| IL2 | −4.0 | 0.9 | −6.0 | 0.9 | −1.0 | 0.8 | −3.0 | 0.8 |
| MMP2 | −6.5 | 1.1 | −5.0 | 0.9 | 3.5 | 1.7 | 5.0 | 1.6 |
| NOS2 | −0.5 | 0.1 | −6.0 | 1.1 | −0.3 | 0.1 | −5.8 | 0.8 |
| PTGS-2 | −3.0 | 0.2 | −5.0 | 0.6 | −1.8 | 0.3 | −3.8 | 0.5 |
| SPARC | −4.0 | 0.9 | 0.0 | 0.2 | 2.3 | 1.0 | 6.3 | 0.8 |
| STMN1 | −5.0 | 0.6 | 0.0 | 0.3 | 1.2 | 0.6 | 6.2 | 0.5 |
| TIMP1 | −5.0 | 0.6 | 0.0 | 0.1 | 1.2 | 0.5 | 6.2 | 0.3 |
| TIMP2 | −2.0 | 0.2 | 0.0 | 0.2 | 0.0 | 0.2 | 2.0 | 0.2 |
| TNF-a | −14.5 | 1.3 | −8.0 | 1.8 | −4.5 | 1.2 | 2.0 | 1.5 |
| TUBA | −2.0 | 0.4 | 0.0 | 0.2 | 2.7 | 0.6 | 4.7 | 0.5 |
| TUBB | −5.0 | 0.2 | 0.0 | 0.1 | −0.2 | 0.4 | 4.8 | 0.4 |

For complete provision of anti-arthritic and anti-inflammatory properties, the food or nutrient composition is thus designed to include curcumin and not andrographolide at the dose indicated above.

The disclosure also concerns a method of analyzing the diagnostic genetic profile of a non-human animal comprising:
(a) providing a genotypic database for the species of the non-human animal subject or a selected group of the non-human species;
(b) obtaining animal phenotypic data;
(c) correlating the database of (a) with the data of (b) to determine a relationship between the database of (a) and the data of (b).

The diagnostic genetic profile of the animal or selected group of animals is determined based on the correlating step (c), and selecting the biologically active nutrient from an obtained molecular dietary signature, the molecular dietary signature being a variation of expression of a set of genes which may differ for the genotype of each animal or selected group of animals.

The data of the animal is one or more data items related to genotype, selected from the group consisting of breed, breed(s) of parents, pedigree, sex, coat type, and evident hereditary conditions and disorders and the phenotypic data are selected from the group consisting of age, weight, veterinary medical history, reproductive history, present wellness or disease state, appetite, physical activity level, mental acuity, behavioral abnormalities and disposition.

Another aspect of the disclosure is a method of identifying a pharmacological product for an individual animal having a genotype, comprising:
(a) using a "reference" dataset containing functional genomic profiles of biological samples of the genotypes of different animals of the species, the different animals being healthy animals;
(b) selecting a "target" dataset containing the functional genomic profile of biological samples of the genotypes of different animals, the different animals being unhealthy animals;
(c) using a "pharmacological product" dataset comprising different effects of pharmacological product on functional genomic profiles of the different animals of different genotypes from those of the target group (b), the different genotypes being differently responsive to the same pharmacological product; and
(d) having the reference dataset or target dataset include an individual animal for which the biologocalily active nutrient is to be identified.

At least one of the "reference" or "target group" datasets are related with the pharmacological product dataset to identify pharmacological product is for the selected animal genotype to prevent, treat, control, or modulate a state of physiological homeostasis or pathophysiological condition of the individual animal in the reference dataset or target group.

As used in this disclosure a "pharmaceutical product" refers to one or more therapeutic drugs, compounds or compositions including one or more nutrients or other supplements or constituents having properties which prevent, treat, control or modulate a state of physiological homeostasis or pathophysiological condition.

The Examples above, and Examples 1-9 above identify particular genes related to specific healthy or unhealthy conditions in an animal. These genes are identified as relating to biologically active nutrients. Similarly, these genes are related to pharmaceutical products and compositions and the disclosure is also applicable to the relevant pharmacokinetic conditions.

Genetic variations in response to a pharmaceutical product have involved the muscle relaxant suxamethonium chloride, and pharmaceutical products metabolized by N-acetyltransferase. About one in 3500 Caucasian people has a less efficient variant of the enzyme (butyrylcholinesterase) that metabolizes suxamethonium chloride. Consequently, the pharmaceutical product's effect is prolonged, with slower recovery from surgical paralysis. An enzyme system known as the cytochrome P450 oxidases provides the body with an inborn system for clearing xenobiotics (chemicals not normally produced by or expected to be present in the body). The cytochrome P450 oxidases are involved in pharmaceutical product metabolism, and genetic variations in their pathways should affect large populations of animals.

The thiopurines and thiopurine methyl transferase enzyme system has been involved in one test for a genetic variation in drug metabolism that had a clinically important consequence. This system metabolizes 6-mercaptopurine and azathioprine, two thiopurine drugs used in a range of clinical indications, from leukemia to autoimmune diseases. In humans with thiopurine methyl transferase deficiency, thiopurine metabolism proceeds by other pathways, one of which leads to production of an active thiopurine metabolite that is toxic to the bone marrow. The frequency of this mutation is one in 300 people. These individuals need about 6-10% of the standard dose of the drug. If treated inadvertently with the full dose of the pharmaceutical product, these individuals are at risk for severe bone marrow suppression. For these humans, genotype predicts clinical outcome, which is now considered a prerequisite for an effective pharmacogenetic test. When applied to animals the genetic variations in such pathways should affect large populations of animals.

The disclosure is directed to a method, apparatus and system of obtaining, analyzing and reporting laboratory test data in relation to the nutrition assessment data of an animal together with the genetic data related to that same animal.

These data include tests related to at least one of the function of and nutritional analysis, paternity, DNA fingerprinting, and the functional genomic profile. These data are relevant to the likely morbidity, likely longevity, and/or the potential risk for disease or disorder for the animal.

According to one aspect of the disclosure, nutrition profiling of an animal is affected to determine characteristics related to the temperament of the animal which impacts on its longevity. Biological and genetic laboratory test data from a bodily fluid or tissue of an animal are analyzed.

More particularly the disclosure comprises analyzing genetic data of animals, analyzing nutrition assessment data of animals, combining this as necessary, and permitting an analysis predicting nutrition, disease and disorder probabilities and longevity of selected animals. The analysis and diagnosis is made, and a report is provided to a remote user based on the analysis the nutrition assessment data of the animal and/or the genetic data.

In light of the above, there is provided by this disclosure a system for managing animal comprehensive nutrition assessments of animals and genetic diagnosis, including the performance of specific tests.

The disclosure also provides a bioinformatics system for inputting, controlling, analyzing and outputting of a broad range of criteria related to the nutrition, genetic background and longevity of animals. This includes a system concerning phenotype data and genetic data relating to animals. Further, there is provided a system for screening of genetic data and genomic mapping, and integrating the phenotype nutrition assessment data and genetic identifier and assessment data in a central database processing resource ("CDPR"). Moreover, there is provided a system for analyzing the nutrition assessment or phenotypic data with the interrelated genetic or genotypic data. Thereafter, those data and analyses are communicated from the CDPR in a broad range and in a manner that has not previously been possible.

The present disclosure offers a unique solution to above-described problems by providing an apparatus, method and system, in relation to animals, for performing data analyses of genetic and biological specimens from specific subject animals or animal groups in relation to specific subject animal or animal groups of genetic data. The apparatus, method and system comprises a controller for obtaining, inputting, and analyzing genetic, biological, physiological, and pathological test data together with genomic mapping and genetic screening data into the CDPR.

The biological, physiological, and pathological data of the subject animal or animal group and the genetic data of the subject animal or animal group are communicated to a remote user as raw data or as related, analyzed biological, physiological, and pathological data and genetic data. The remote user can also appropriately access the CDPR to input data to, or obtain data from, the CDPR.

The CDPR includes at least two databases, one of the databases contains genetic information in relation to animals and the other is a phenotypic database.

The genetic database is either a specific file of a selected animal or a generalized animal database relating to group characteristics, and is cross-relatable with the phenotypic database of particular selected subject animals.

Additionally other databases can be used and cross-related to these databases. The genetic database includes data from selected animals, animal families, animal breeds and/or data related to selected animal diseases and/or disorders. Other databases include those related to genetic markers or maps of animals, databases related to epidemiology, purebred animal ownership, identification registries, and studbook registries.

The phenotype, nutrition profile, or nutrition assessment database contains data which is mostly phenotypic. The genotype database includes data which is in the category of mostly genotype or genetic and which may include a second category of some phenotype data which predicts or manifests the genotype and genetic data. The disclosure includes relating the phenotypic data to either one or both types of the genotypic data.

According to the disclosure there is an analysis of the profile of a non-human animal. The analysis comprises: a) providing a genotypic database to the species of the non-human animal subject or a selected group of the species; b) obtaining animal data; c) correlating the database of a) with the data of b) to determine a relationship between the database of a) and the data of b); c) determining the profile of the animal based on the correlating step; and d) determining a genetic profile based on the molecular signature, the molecular signature being a variation of expression of a set of genes which may differ for the genotype of each animal or a group of animals.

The nutritional aspects and regimen is at least related to the nutrient or caloric composition, or the food allergies and food intolerances. The therapeutic intervention or maintenance is at least one of drugs, nutraceuticals, or holistic treatments, exercise or liquid intake. The diagnostic genetic and laboratory test data is a comprehensive general nutrition profile and selectively at least one selected diagnostic profile for a selected subject. Preferably the genetic and laboratory data for the subject is obtained over time from the same laboratory. This is likely to enhance the uniformity of the data, and render the determinations more accurate, and predictive of nutrition, nutritional requirements, temperament, and longevity.

The interrelationship is affected by a computer which is at least one of an expert system or interrelationship program or network for determining data base and data relationships. This can be a system such as a neural network, or other statistical sampling systems and networks.

The database of at least one of the species or the group is periodically updated thereby to obtain cumulative data of the species or group. Preferably both these data bases are used, and preferably both are updated to obtain the cumulative data. The data of the subject is periodically updated thereby to obtain cumulative data. Preferably, both the databases are periodically updated. The updating picks up data drift in different populations of the subjects, groups and species over time, and thereby allows for the regulation of the database so as to be substantially or essentially current.

By having this feature there is obtained a method and system which provides for enhances nutrition care and well-being management of the subject. Thus the data of the subject is compared to substantially or essentially current data. Similarly by retaining a history of the subject data and relating this to the updated databases, the accuracy with which the nutrition care and well-being is managed is significantly enhanced.

The disclosure also includes the step of reporting the determination of the care, well-being, nutrition or other therapeutic requirements and suggestions for nutrition on a communications network including the Internet. Preferably, there is a payment procedure for the report which is achieved through the Internet. This communication network and structure is described here in further detail.

There is provided means for inputting data into the genetic database and phenotypic database, and other databases, storing the data in these databases, analyzing the data in a relational sense from the different databases, and retrieving the data from these databases, namely the databases which are part of the CDPR.

A further aspect of the disclosure is the accessibility of the nutrition assessment database and/or genetic database or other databases of the CDPR by the remote user selected on the basis of password, security control, and financial payment such that the data can be transmitted into and from the CDPR by a computer network. Use of selected passwords, encryption systems, and payment systems are employed to facilitate and restrict the flow of data in and/or out of the databases. Alerts can be set up to advise of attempts at unauthorized access to the CDPR. The computer network may conveniently include the Internet.

As required, the data in the CDPR can also be distributed to multiple authorized remote parties, namely third parties for research or other analysis. The disclosure also includes a method and system for achieving this.

Further aspects of the present disclosure will become apparent in the course of the following description and by reference to the attached drawings.

The present disclosure will now be described in detail with reference to a few preferred embodiments thereof, as illustrated in the accompanying drawings. In the following description, numerous specific details are set forth in order to provide a thorough understanding of the present disclosure. It will be apparent, however, to one skilled in the art, that the present disclosure may be practiced without some or all of these specific details. In other instances, well known process steps have not been described in detail in order to not unnecessarily obscure the present disclosure.

C. Genotypic Markers of Disease

Recent advances in molecular genetics have focused on mapping the human genome, and this has stimulated interest in developing parallel genetic maps for animals. For example, it is estimated that a minimum of ten years and several million dollars will be needed to map the canine genome. Once developed, a genetic map provides information about the relative order and placement of genes or specific DNA markers on specific chromosomes. This allows one to locate specific regions on chromosomes where genes of interest are likely to be found. Once a molecular marker is identified close to a specific gene of interest, screening tests for this particular marker can be used to identify individuals carrying or expressing the trait.

One or more of a panel of tests relate to at least one the function of and nutritional analysis, DNA fingerprinting, and the functional genomic profile. These data are relevant to the likely morbidity, likely longevity, and/or the potential risk for disease or disorder for the animal.

There is a dynamic method and system of managing the nutrition care, well-being and nutritional requirements of dogs or cats. An example is set out for a dog. It can be equally applicable to a cat.

A data base relating to the dog species generally, and a data base relating to a selected group, for instance, the breed, of the dog is used. Data is obtained relating to the particular dog subject, and this data includes laboratory test data, and ideally diagnostic laboratory data relating to that dog. The database of the dog and the breed, for example, is related to the data of the subject data of the dog by a computer. There is then determined, based on this relationship, a regimen for the management and are of the dog subject.

The nutrition care and well-being could include the nutritional management or the lifestyle management. The data base of the selected group of the species is at least one of breed, age, sex, size, weight, performance use, or geographical location.

The nutritional regimen is at least related to the nutrient or caloric composition needed for the dog subject, or the food allergies and food intolerances of the dog subject. The therapeutic intervention or maintenance needs of the dog are at least one of drugs, nutraceuticals, liquid intake, holistic treatments or exercise.

The diagnostic laboratory test data is a comprehensive general nutrition profile and selectively at least one selected diagnostic profiles for a selected subject. The laboratory data for the subject is ideally obtained over time from the same laboratory. This is likely to enhance the uniformity of the data, and render the determinations more accurate, and predictive of nutrition, nutritional requirements, temperament, and longevity.

The database of at least one of the species or the group is periodically updated thereby to obtain cumulative data of the dog species or group within the dog species. Both of these data bases generally should be used, and both should be updated to obtain the cumulative data. In some cases, only one of the data bases is used and/or one of them is periodically updated.

The data of the dog subject is also periodically updated. Overall there is obtained cumulative data of the dog subject, species or group. The updating picks up data drift or data trends within different populations of the particular dog subject, the groups (for instance, breed) and the species (for instance, the dog generally as a species) over time. This allows for the review and oversight of the database so as to be substantially or essentially current.

Enhanced nutrition care and well-being management of the dog subject is obtained. Thus the data of the dog subject is compared to substantially or essentially current data. Similarly, by retaining a historical record of the dog subject data and relating this to the updated databases, the accuracy with which the management of the nutrition care and well-being, and the nutrition design of nutritional requirements or therapeutic and maintenance interventions is significantly enhanced. In this manner, for instance the food, supplements, nutraceuticals and the like, can be modified by additions and/or subtractions of components based on the determined relationship, since these cumulative and dynamic data bases and data analyte changes over time, whereby the determined relationship is significantly enhanced. Management of the dog subject in one or all of these respects is dealt with a high level of precision and predictability.

The computer is at least one of an expert system or inter-relationship program or network for determining data base and data relationships. This can be a system such as a neural network, or other statistical sampling systems and networks, and is discussed in more detail.

The determination of the nutrition care, well-being, nutritional or other therapeutic requirements and suggestions for promoting and maintaining nutrition of the dog is reported on a communications network including the Internet. There is a payment procedure for the report which is achieved through the Internet. This is discussed in more detail.

A more detailed explanation of the features is now described.

An initial database, from a recent temporal period made on a group of nutrition dogs. will use physical characteristics, nutrition history, and comprehensive laboratory data of these dogs for a specific geographic area such as the U.S.A. and Canada, but also other geographic areas could be used. Additional databases could be developed for other countries. Generally the same laboratory is used to generate the database. The temporal retrospective database will be augmented in an on-going fashion with prospective data that continues to accumulate over the future testing years. Results will be analyzed from the temporal retrospective database and then will be periodically reanalyzed every 6-12 months depending on the size of the database to search for any trends or drift in the values of specific analytes over time.

This is an important database to accumulate because the presence of drift over time means that subsequent studies of the same or other animals, whether they be nutrition or have diseases, disorders or changes in lifestyle, diet or other parameters including reproduction, or performance use need to take such drift in the database into account in order to accurately interpret the values obtained. Animals of specific breed or type characteristics, size, age, weight, performance level, lifestyle, geographic location will then have their laboratory profiles and-physical characteristics and nutrition history entered into a database that will start from entry into the system and continue on a regular basis over time, preferably at least annually. Also entered into this database will be puppies that will be tested for the first time at about six months of age, pre-puberty, and then before puberty, preferably in anestrus females, and then annually thereafter in a comprehensive manner to establish a cumulative laboratory database for the individual animal.

These data will also be put into a group-specific database for the breed characteristics or the activity characteristics or any other parameter that is useful to group together for analytical purposes. This method of gathering comprehensive and cumulative data will permit not only analysis of individual animals, whether they be nutrition or expressing some stage of disease or disorder, but also will allow analysis of their membership in a group. When the group is analyzed it will provide a database for predictive laboratory value expectation for similar members of the group. By developing these databases in a cumulative manner the trends for particular analytes or groups of analytes predictive of organ function, for example, can then be compared within individual animals, nutrition or diseased, with that of the retrospective and prospective nutrition animal database to look for differences in trends. Those differences in trends, as well as differences in individuals or groups of animals, can then be used as a predictor of nutrition, disease and longevity.

Once trends or changes are identified within individual animals or within the related groups of animals or within specific analytes or groups of analytes from a database, this will permit intervention in a management and treatment perspective. The intervention can be nutritional, can include the use of dietary supplements, use of specific nutraceuticals, and can include, of course, other conventional and alternative treatments and management of nutrition care. The database so gathered, while primarily phenotypic in its laboratory analytical sense and its patient descriptive sense, will also be predictive for the most part of the genotype of the individual animals or groups of animals in the population, because the canine genome has changed very little over the last hundred years, and so the majority of the canine genome is identical between dogs, breeds and individuals. Differences in phenotype (physical appearance and size and weight, for example) within dog breeds constitutes a very small genetic variation, less than 1%, within the overall genome. Predicting genotype and phenotype with these comprehensive and cumulative laboratory test panels permits a novel approach to intervening in the management and treatment of canine disease and disorders and also in the maintenance of canine nutrition and longevity.

The comprehensive cumulative database developed with this disclosure allows one to look at very early subtle changes that are consistent within individuals or groups of related individuals, animals within a related group so that one can predict disease sooner, make interventions that are less expensive, less invasive, and more effective, and thereby reverse the process before it becomes more serious clinically.

One of the most effective and least invasive or harmful ways to intervene in promoting animal nutrition and longevity would be to utilize dietary management. Specifically, wholesome foods are the key to a balanced functioning immune system and the resistance to disease. Given the tight database that is developed by this approach, extraneous noise in the results of comprehensive laboratory analyses is minimized. One can take the findings then for individual animals or groups of animals having cumulative laboratory evidence of trends or drift from the normal ranges and design specific dietary interventions that will rebalance the system and promote immunological function and resistance to disease. This method of identifying what changes could be made in dietary components or supplements does not depend on single point in time individual pet or other animal data, but in fact the key is developing a cumulative comprehensive database over time for normal animals in a like-group location or activity level, as well as specific animals within the group in order to determine what trends are evidenced over time and thereby use the trend to give a more solid determination of what these changes in nutritional requirements or nutritional supplements or other intervention should be.

An example of the comprehensive diagnostic testing used in this disclosure are selected examples for diagnostic genetic panels, screens and microarray analysis or other High Through Put systems ("HTS").

In a practical application on a large scale, the comprehensive individual and group databases that relate to thyroid function and animal behavior are important. As the key to having an individual animal become a successful companion animal or member of a household, the social interaction of the animal with the caregivers is crucial. If the animal has an undesirable behavior or social bad habits, very likely the animal will be isolated, stressed, and may be treated unkindly and even ostracized by some family members, so that the animal may eventually be given up or even sent to a pound and sheltered and be euthanized. If kept by the family, the animal will likely undergo significant stress which would contribute to immune suppression and lack of well-being and thus further promote the abnormal behavior. By using this database and identifying animals that have very early subtle changes in laboratory analytes shown by their individual or cumulative data drift from the expected normal parameters, one can intervene before the abnormal behavior becomes unbearable for the family caregivers.

The databases of the functional genomic profile and the nutritional data base can be used to assist in resolution of the disease state or condition.

As a relationship for has been recognized between thyroid function and behavior, early detection of thyroid imbalance allows one to intervene, specifically with nutritional support, and managing individual foodstuffs and supplements that would optimize thyroid function before the disease progresses to the stage where thyroid hormone supplement becomes an essential component of the management and treatment. For instance, food supplements containing kelp, iodine and the minerals from green leafy vegetables could be very helpful in enhancing thyroid glandular output and function. Soybean-derived products by contrast tend to inhibit thyroid function, as can the quality and content of protein in the diet. Because the thyroid is a major master gland that controls the metabolism of so many functions in the body, being able to balance it with optimum nutrition would be extremely important because thyroid disorder is the most common endocrine dysfunction amongst companion animals today.

As it is well known that specific breeds that are used for performance events can have quite different basal thyroid metabolism, for example sighthounds and other coursing breeds vs. toy breeds or working breeds, it is important in the cumulative database to determine these characteristics by comprehensive profiling expected of this group as a whole, so that the data for individual animals could be compared to the group. Values for this specific functional group by breed would then be compared to the entire database for the canine as a species and specific trends over time would be developed relating to age and to environmental influences. Once the specific determinants of the individuals and the group that they belong to have been made, the trends that have been identified would be used to modify and intervene to promote nutrition and longevity, specifically again with modifications to dietary components or supplements as well as other changes in lifestyle, including exercise, group housing, individual housing and parameters that would promote wellness and longevity.

The term "group" here has many different characteristics. It could include, for example, a specific breed of canine, a specific purpose for which these canines are used, such as those who are purely companion pets in a home situation, performance animals for show conformation, for obedience, working trials, coursing trials, and for sheep herding and other herding purposes. It could also involve groups of animals depending on where they live—in a temperate climate, a warm or tropical climate, an arid desert climate, or a cold northern climate. It will include, of course, animals that live in urban and rural areas, animals that live near water, animals of various ages, intact or neutered, and for reproduction. In other words, the term "group" is used in a very broad sense here and can apply to any group that the user wishes to inquire of the database. Thus, the group is any selected subset of the nutrition or diseased or disordered animals within the entire database.

The determination of the interrelationships between individuals or groups of individuals in the database can use any one of a number of computerized or other methods of analysis, simple or complex, including such things as neural networking or other kinds of relational technology evaluative databases.

The system and procedure for carrying out the genetic test is, for instance a microarray analysis of DNA or RNA. Thereafter there will be an analysis with a nutritional data base. This is be done by a comparison of the functional genomic profiles as necessary with one or more of the nutritional databases.

This disclosure utilizes comprehensive and cumulative data profiling in a novel way over time to allow one to predict the specific nutritional management interventions that will assist in the care and management of the very earliest stages of specific abnormalities or trends that have been identified in the nutrition profile of animals, thereby extending and improving their nutrition and longevity. This is a unique approach to scientifically and medically determining by comprehensive and cumulative laboratory profiling of individual animals and animals within specified defined groups to permit intervention in preventive and management and treatment of general and veterinary medical nutrition care. Specifically, this disclosure directs the outcome of the laboratory profiling to nutritional and nutritional supplement management of the specific identified abnormalities and trends over time to accomplish this goal. This is not only important but also practical because nutritional intervention and management is relatively inexpensive, non-invasive and easily accepted by the pet owner and the veterinary professional making these recommendations.

Overall System

Figure 14:
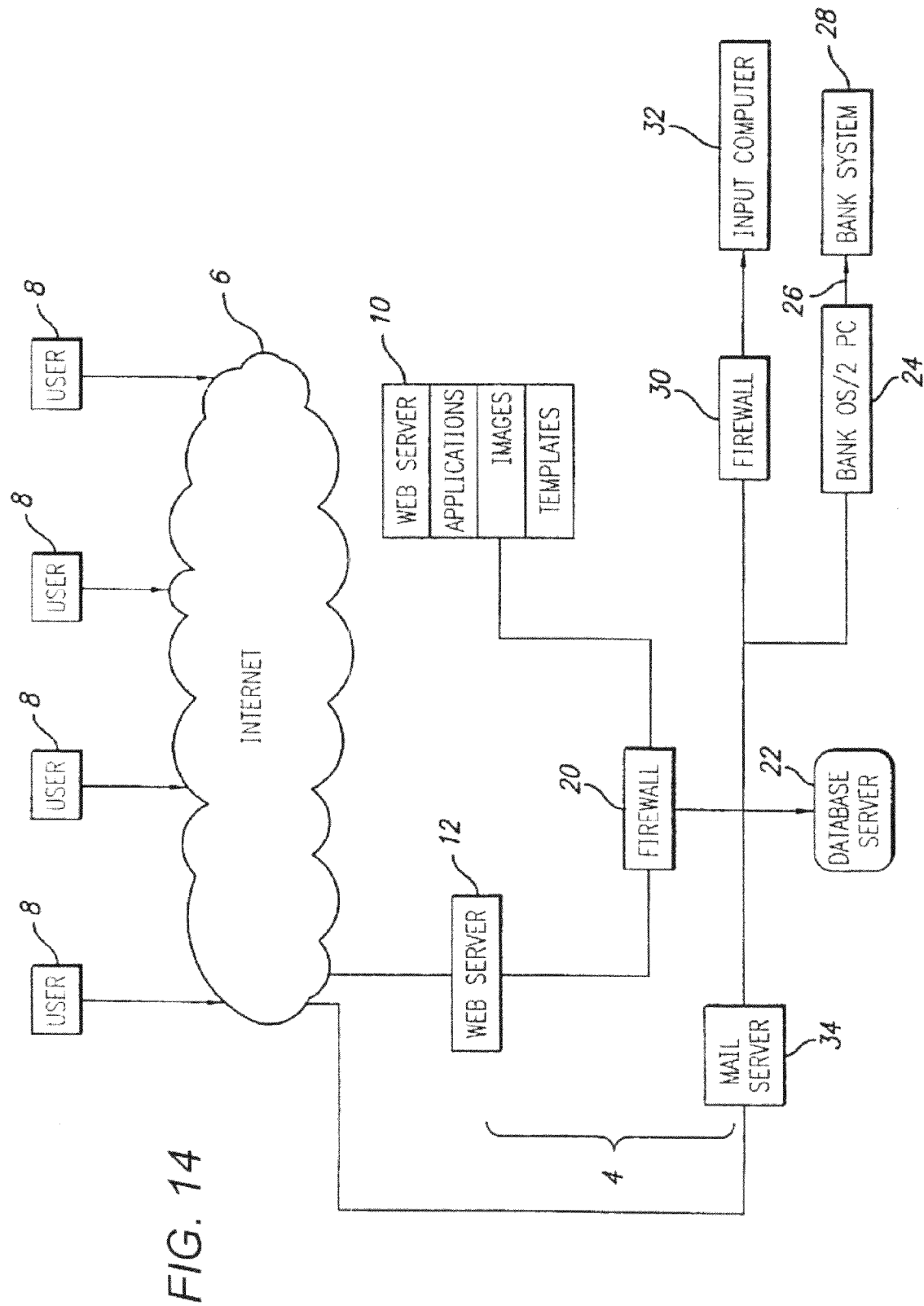
FIG. 14 is an overall view of a web-based system to provide access to a database management system of an animal genetic database and a nutrition assessment database of the disclosure, in relation to the Internet.

FIG. 14 is an overview of the web-based system to provide access to the invented database management system. With this system multiple users, for instance, remote users 8, access the web site 4 using the Internet 6. Each of the users 8 has a computer terminal with the appropriate software for accessing Internet. The users 8 may be unknown to the web server computers 10 and 12. Each user 8 is allowed to browse the web site and explore how the system functions.

There are several aspects to maintain security of information maintained in the database server 22 and a banking system 28. A firewall 20 prevents any user 8 from accessing any of the components behind the firewall 20. In this way the users 8 have access to the web server computers 10 and 12, but only have access to the database server 22 through the firewall 20. The database server 22 maintains, among other things, various database fields with respect to each of the nutrition profiles of subjects and the genetic information of a subject and groups. The database 22 maintains the services with a designation associated to determine what nutrition assessment data and genetic data can be browsed by the users 8. Each of the web server computers 10 and 12 allow users 8 to view subject and group categories and actual services and data products which are available from the database.

The web server computers 10 and 12 can be identical and can be duplicated as additional load or growth on the system occurs. The web server computers 10 and 12 share the responsibility for servicing the users of the site. This arrangement provides for expandability of the system by merely adding additional web server computers as necessary.

Preferably, the system includes an appropriate computer terminal 24 for interfacing with independent financial institutions which are connected on-line via the serial connection 26 to the financial institution computers 28. This allows automatic real time confirmation of the access of nutrition profile and genetic data services and products. Once a user requires access to a product or service, the user goes through identification or registration process and the exchange of financial information to allow for credit or debit card payment of the purchase. This is verified, confirmed and authorized by the appropriate bank system institution 28. Confirmation of the purchase or deposit of data, or a service is made by a mail server 34 which sends an E-mail to the user 8 confirming the purchase or deposit. The mail server 34 allows for mail to be received and sent out. Security of the various databases is maintained. Alert messages are generated when an unauthorized access is attempted. Verification messages, authorization messages and confirmation messages are generated as appropriate.

The database server 22 is also designed to interact with an input computer 32 operated by a CDPR. A firewall 30 serves to prevent unauthorized access to the database server 22 or to the input computer 32. The input computer 32 can input nutrition profile data and genetic data to the database, after appropriate access and/or passwords are entered into the system. Similarly, users 8 through their own computers can use appropriate access codes and passwords to access input data to the database server 22. This is tightly controlled for security reasons. The data may only be added to an independent sub-database of the data server 22, and only after scrutiny by the CDPR operator of the database through input computer 32, will this data from users 8 be subsequently added to the main database server 22.

Figure 15:
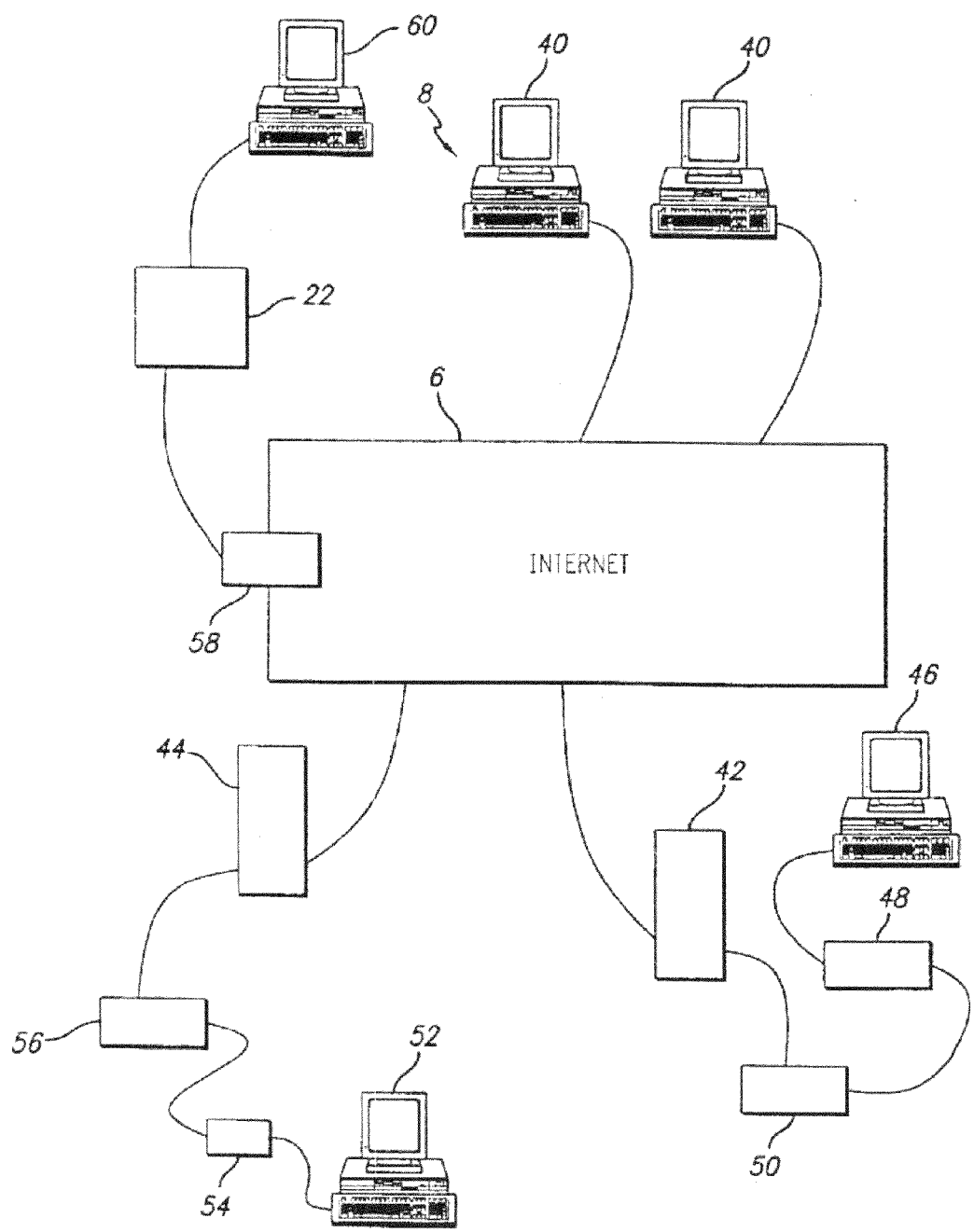
FIG. 15 is a graphical illustration of a computer network, namely the Internet.

FIG. 15 is an illustration of the Internet and its use in the system of the disclosure. The Internet 6 is a network of millions of interconnected computers 40 including systems owned by Internet providers 42 and information systems 44.

Individual or corporate users may establish connections to the Internet in several ways. A user on a home PC 46 may purchase an account through the Internet provider 42. Using a modem 48, the PC user can dial up the Internet provider to connect to a high speed modem 50 which, in turn, provides a full service connection to the Internet. A user 52 may also make a somewhat limited connection to the Internet through a system 20 that provides an Internet gateway connection 54 and 56 to its customers. The database 22 is also connected into the Internet 6 through an appropriate modem or high speed or direct interface 58. The database 22 is operable and maintained by the CDPR operator computer 60. Users of the databases of the disclosure would access the Internet in an appropriately selected manner.

Figure 16:
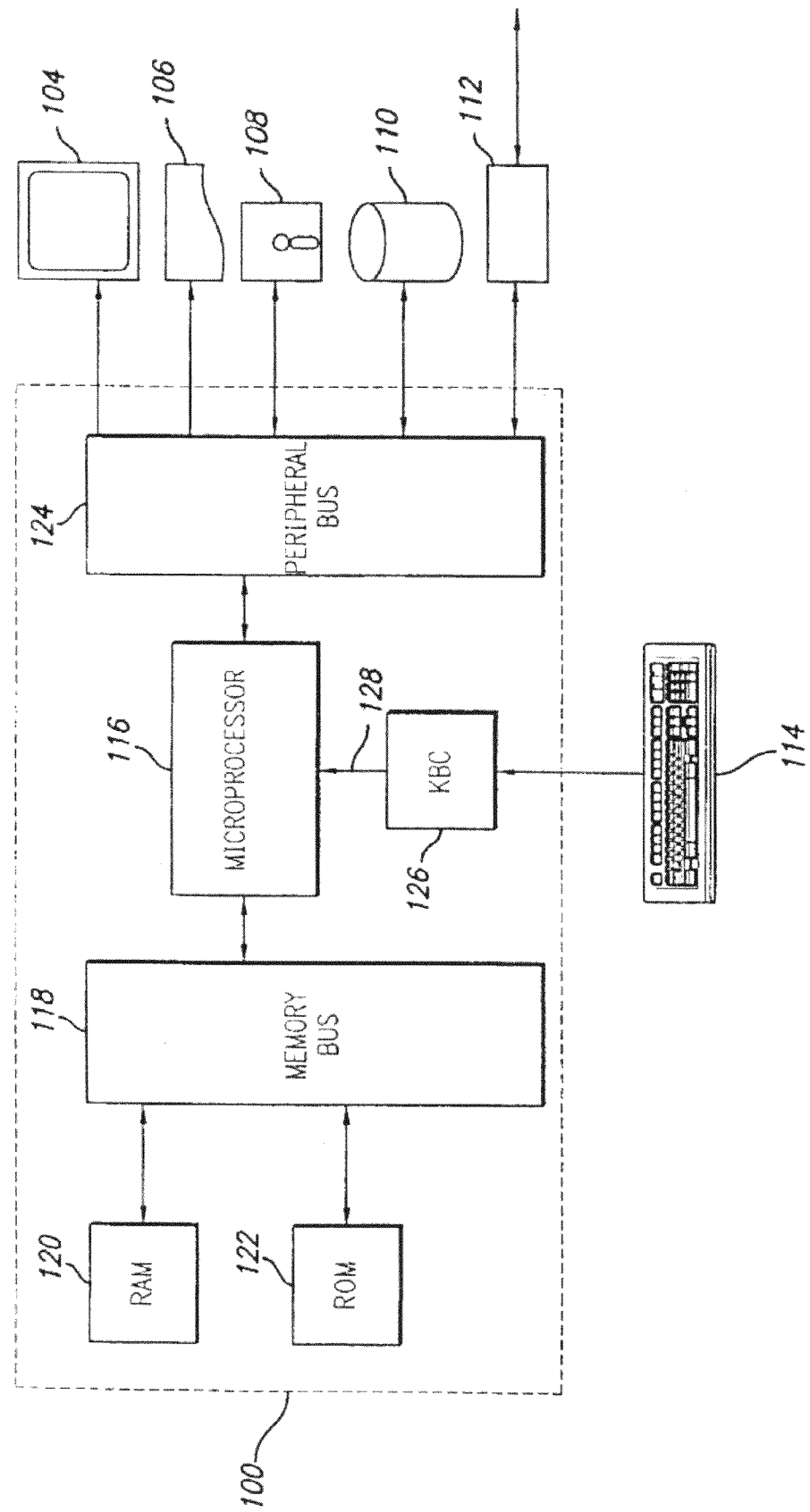
FIG. 16 is a block diagram of an exemplary computer system for practicing various aspects of the disclosure.

FIG. 16 is a block diagram of an exemplary computer system 100 for practicing various aspects of the disclosure. The computer system 100 includes a display screen or monitor 104, a printer 106, a disk drive 108, a hard disk drive 100, a network interface 112, and a keyboard 114. The computer system 100 includes a microprocessor 116, a memory bus 118, random access memory (RAM) 129, read only memory (ROM) 122, a peripheral bus 124, and a keyboard controller 126. The computer system 100 can be a personal computer.

Microprocessor 116 is a general purpose digital processor which controls the operation of computer system 100. Microprocessor 116 can be a single-chip processor or can be implemented with multiple components. Using instructions retrieve from memory, the microprocessor 116 controls the reception and manipulation of input data and the output and display of data on output devices.

Memory bus 188 is used by the microprocessor 116 to access RAM 120 and ROM 122. RAM 129 is used by microprocessor 116 as a general storage area and as scratch-pad memory, and can also be used to store input data and processed data. ROM 122 can be used to store instructions or program code followed by microprocessor 116 as well as other data.

Peripheral bus 124 is used to access the input, output, and storage devices used by computer system 10. These devices include the display screen 104, printer device 106, disk drive 108, hard disk drive 110, and network interface 112. The keyboard controller 126 is used to receive input from the keyboard 114 and send decoded symbols for each pressed key to microprocessor 116 over bus 128.

The display screen or monitor 104 is an output device that displays images of data provided by microprocessor 116 via peripheral bus 124 or provided by other components in computer system 100. The printer device 106 when operating as a printer provides an image on a sheet of paper or a similar surface. Other output devices such as a plotter, typesetter, etc. can be used in place of, or in addition to the printer device 106.

The disk drive 108 and hard disk drive 110 can be used to store various types of data. The disk drive 108 facilitates transporting such data to other computer systems, and hard disk drive 110 permits fast access to large amounts of stored data.

Microprocessor 116 together with an operating system operate to execute computer code and produce and use data. The computer code and data may reside on RAM 120, ROM 122, or hard disk drive 120. The computer code and data could also reside on a removable program medium and loaded or installed onto computer system 100 when needed. Removable program mediums include, for example, CD-ROM, PC-CARD, floppy disk and magnetic tape.

The network interface circuit 112 is used to send and receive data over a network connected to other computer systems. An interface card or similar device and appropriate software implemented by microprocessor 116 can be used to connect computer system 100 to an existing network and transfer data according to standard protocols. As such he computer system is connectable through an interface device with the Internet 6.

Keyboard 114 is used by a user to input commands and other instructions to computer system 100. Other types of user input devices can also be used in conjunction with the present disclosure. For example, pointing devices such as a computer mouse, a track ball, a stylus, or a tablet can be used to manipulate a pointer on a screen of a general-purpose computer.

The present disclosure in relation to the animal database management of data can also be embodied as computer readable code on a computer readable medium. The computer readable medium is any data storage device that can store data which can be thereafter read by a computer system. Examples of the computer readable medium include read-only memory, random-access memory, magnetic data storage devices such as diskettes, and optical data storage devices such as CD-ROMs. The computer readable medium can also be distributed over network coupled computer systems so that the computer readable code is stored and executed in a distributed fashion.

Specific System

Figure 17:
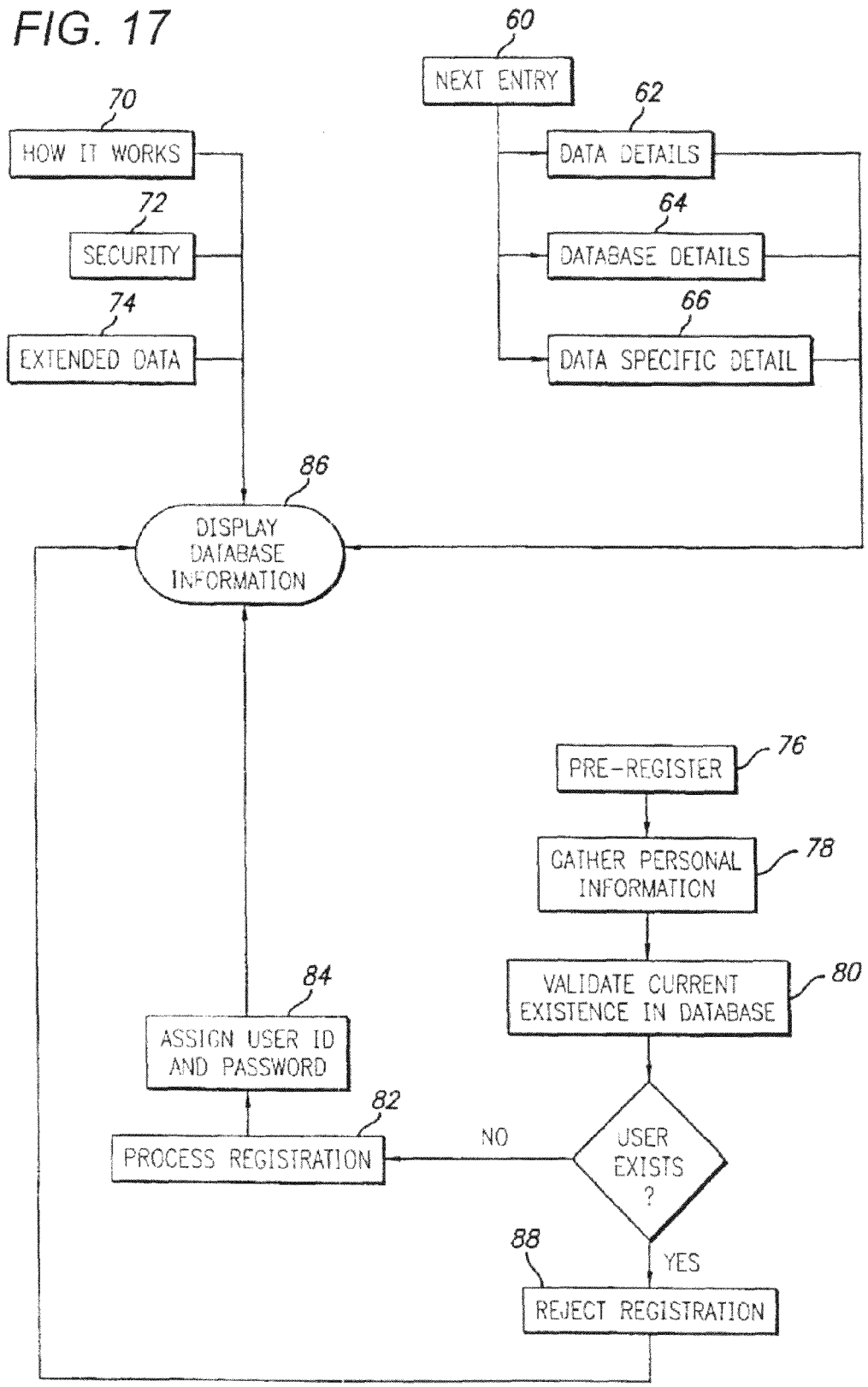
FIG. 17 is a view of a browser for the database management system for accessing an animal genetic database and a nutrition assessment database of the disclosure.

FIG. 17 illustrates a browser system for use with the database system of the disclosure. A browser goes through a number of preliminary screens and logic steps, and reaches a screen 60 entitled "Next Entry". This screen provides data details or information generally indicated as 62. Clicking on any of these categories allows the user to review database details 64, data specific details as generally indicated by 66. In this way, the user can index through a number of screens to get information regarding the different databases of the system. In addition, clicking on any of the triggers 70, 72, 74 and 76 is possible. These correspond to HOW IT WORKS, SECURITY, EXTENDED DATA and PRE-REGISTRATION. Clicking on trigger 70 provides the user with information on how the process works, explains the system, and provides details on how the user can participate in the database and obtain data or input data. Clicking on trigger 72 provides details regarding security of the system and automatic payment. In some cases, products and services are offered with extended data and clicking on trigger 74 which can provide details of the extended data and explains that this may only be available on certain services or products.

Trigger 76 allows a user to pre-register and obtain user ID number. This ID number is combined with financial information retained in the database in an encrypted form. The pre-registration trigger 76 follows with step 78 which is to gather personal information such as credit card number and expiry date to allow for automatic payment. Step 80 is to validate a current existence in the database, if this occurs. With a negative answer, the user is directed into a registration process indicate as 82. A user ID is assigned and a password is entered. This information is maintained in a portion of the database 22. At 84 the user is provided a screen identifying the user ID at screen 86. If the user already exists, the registration process is rejected at 88 and the user is advised of the information at the display 86. The screen at 86 would also represent the information which is available in the database 22.

Figure 18:
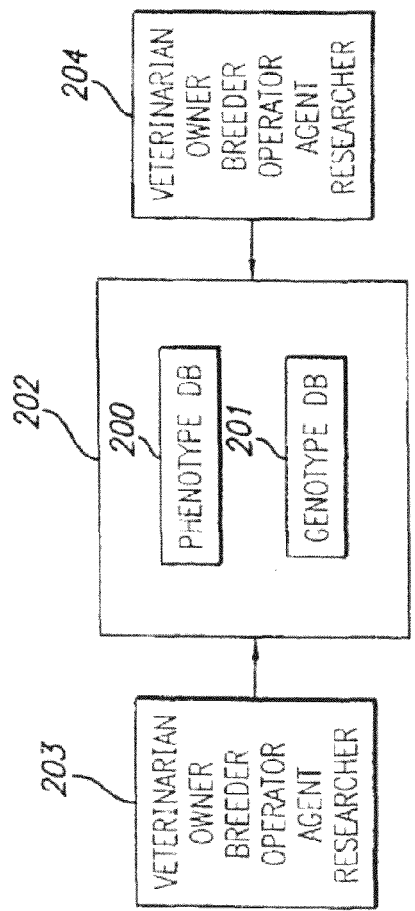
FIG. 18 is a basic flow diagram illustrating an exemplary process by which an operator of a central data processing resource (CDPR) receives and transmits data relating to nutrition assessment and genetic information.

In FIG. 18 there is shown a basic block diagram of the components making up the CDPR. There is the phenotype database or physical nutrition database 200 and a genotype database or genetic information database 201. These are contained in part of the overall CDPR database 202. User input 203 can be obtained from a remote user such as a veterinarian, owner, breeder, or the operator of the database, an agent or researcher. The output from the database 204 could be to the veterinarian, owner, breeder, operator, agent or researcher.

Figure 19:
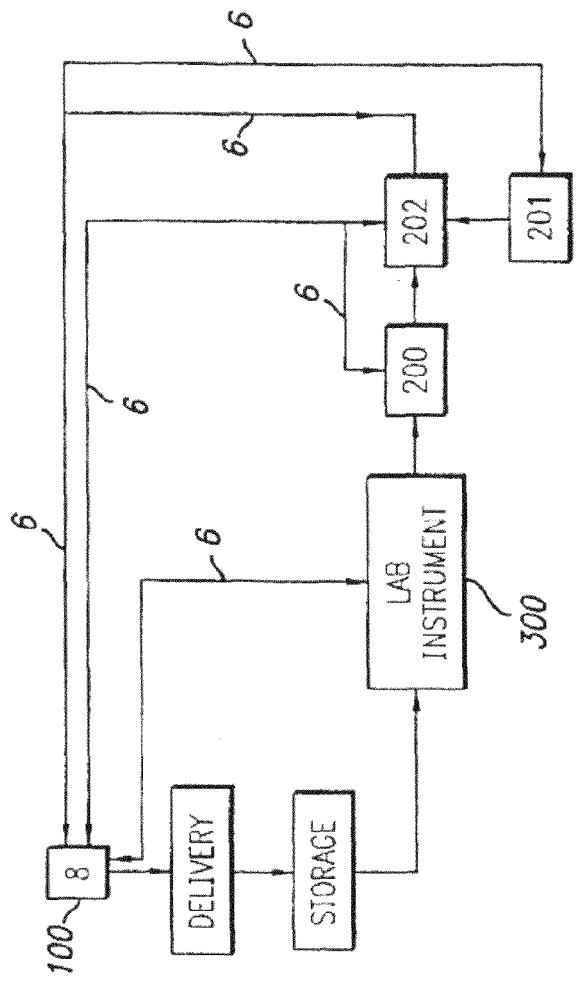
FIG. 19 is a detailed flow diagram of the system steps employed in one embodiment of the present disclosure, wherein a remote user accesses and outputs data.

FIG. 19 shows a relationship for retrieving data from the database 202. The user 8 is represented here as a veterinarian, owner, breeder, operator, or researcher 203 who accesses the CDPR 202 accesses a first screen through a computer network 6 which inquires about information about the user. An access request message is sent, and an appropriate access enabling message is transmitted. The user 203 can obtain partial or full access to the CDPR 202 according to the scale of authority given to the user 203 to access data. There is a computer program system 205 to ensure that payment is made as appropriate before access to the CDPR 202 is granted. In some situations, the appropriate access code 204 can permit bypassing the payment requirement 205 as indicated by line 206. Payments 205 through the computer program can be effected by a credit card entry and automatic transfer to a financial institution on behalf of the operator of the CDPR 202. Such payment for access to the database is effected by a system which is well known in the art. The financial institution will appropriately credit the operator of the CDPR 202 in a financial manner as established between the operator and the financial institution.

Within the CDPR 202 there is the ability to access the physical nutrition phenotype database 200, the genotype database 201, and other databases 207, 208 and 209, respectively. The phenotypic and genotypic information together with other database information can be presented on a single screen or monitor or other viewing means, for instance, hard copy format. The access therefore can be to multiple databases contained within the CDPR 202. After accessing the physical nutrition database 200, the user obtains an analysis report from module 210. The user is then able to read the analysis as indicated by 211 and output the analysis from the read-out 211 as indicated by output 212. The output 212 can be a computer screen read-out, fax or voice information.

The other databases 207 are respectively a pharmacokinetics database to determine the fate of substances administered externally to a living organism. This is applied to drug substances, compounds ingested or otherwise delivered externally to an organism, such as nutrients, metabolites, hormones, toxins. The pharmacokinetics database permits exploration of what a drug does to the body, whereas pharmacokinetics explores what the body does to the drug. The other database 208 includes the biologically active nutrient database. The database 210 is for the target group.

The physical nutrition or phenotype database 200 is subject or group specific. In other words, the data obtained in that database is specific to a particular animal or animal group (breed, family, species, etc.) which has been the subject of a laboratory or research biological examination such that fluid or tissue samples have been subject to analysis in one or more laboratory or research environments. These biological reports can include those from specimens of blood, urine, other body fluids, skin, eyes, skeletal and other tissues. The PT database 200 has the ability to store the subject specific information as required within the CDPR 202.

The genotype specific or genetic disorder or disease data is retained in the database 201 within the CDPR database 202. This data is either subject specific, family specific, breed specific, species specific, disorder specific, or disease specific, and is group or subject specific. The user can access the genotype database 201 and obtain a read-out 213 which can then be transmitted along line 214 to an output 212 in the same manner that the physical nutrition assessment is obtained as an output.

In an alternative approach, the reader can request an analysis 215 from the genotype database as indicated by line 216. This analysis can receive data along line 217 from the analysis information of the physical nutrition assessment. Interpretation of the PT and GT can be obtained as indicated by 218, and this can then be outputted as indicated along line 219. The interpretation of PT and GT 218 can be performed by an algorithm relating to the coefficients and predictability of information relating to disorders, disease and longevity when considering the data from the two databases PT 200 and GT 201. This can be done automatically and outputted along line 219, or there can be an expert interface 220 using skilled personnel to interpret the data of block 218, and this can, in turn, be outputted along line 221 to the output 212.

Database 207 can be a genetic marker database, and the information from that database can be directly input into the output through a read-out 222 and 223 to the output 212. Alternatively, the data from database 207 can be added to the interpretation section 218 of the physical nutrition and genetic information by directing the data along line 224. This data can then be made the subject of the output along the line 219 and 221 as required.

Similarly other databases 207 208, 209, respectively, have read-outs 225 and 226 which can be directly coupled along lines 227 and 228 to the output, or can be directed optionally along lines 229 and 230 to the interpretation module 218. It can then be the subject of interpretation for an expert interface 220 reviews which is, in turn, made the subject of the output 219 and 221.

In each of the output lines 219, 221, 222, 223, 227, 228, and 214 there is also provided an encryption program 231 which can be optionally used in the system. The output 212 can include paper, electronic, or voice read-out as is required.

In this manner, the output 212 provides a compilation which combines the physical nutrition and genetic information relating to a subject, the breed, disease, disorder and lifespan, thereby enabling the receiver of the output 212 to use the compiled information in a manner to facilitate breeding criteria which can be important in relation to animals which are usually inbred or line bred. The information can also be used to facilitate on-going monitoring of particular subject animals. The data from this system can be used to manipulate and regulate breeding, nutrition, and longevity effectively among animals.

Figure 20:
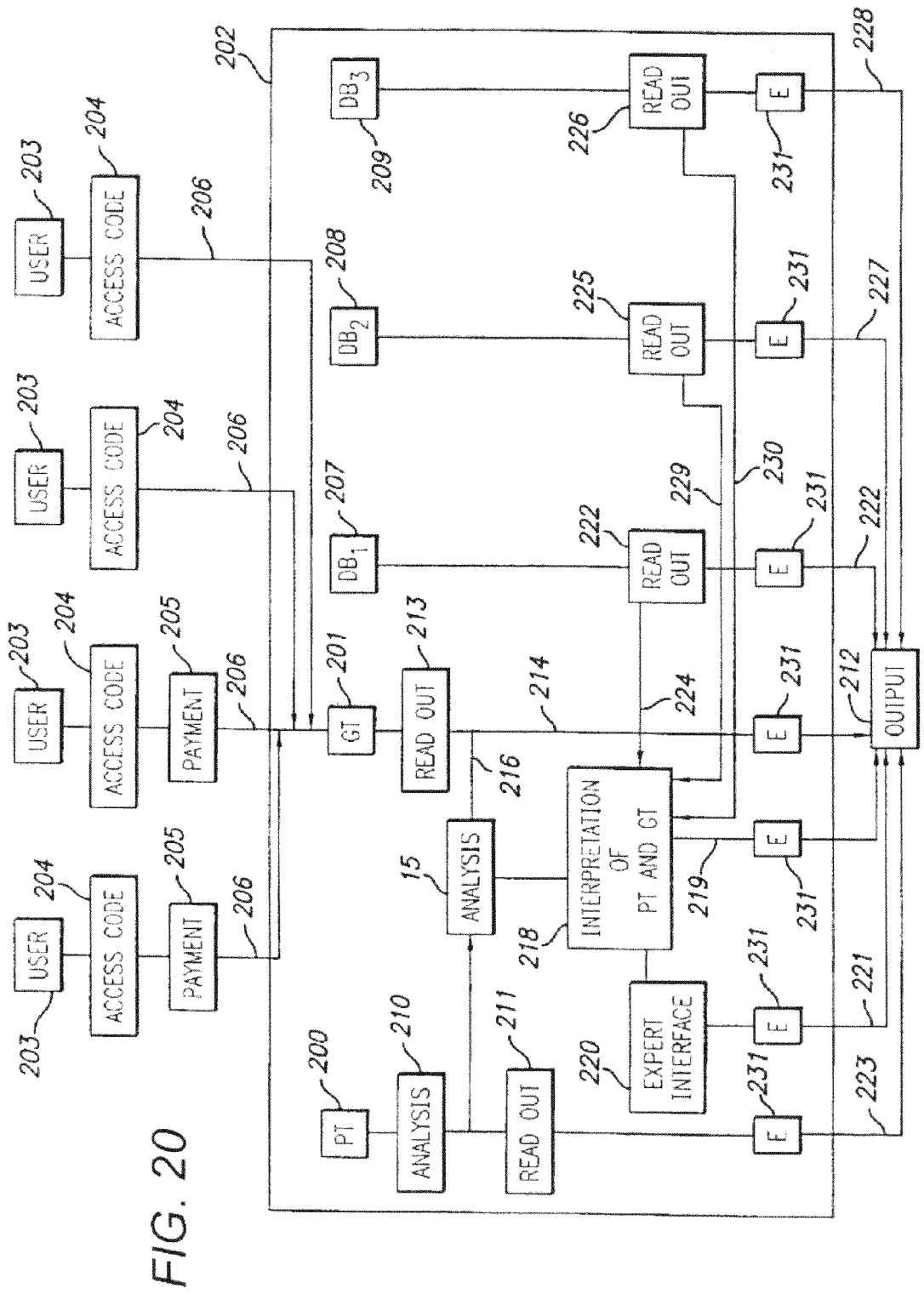
FIG. 20 is a detailed flow diagram of the methods and steps employed by a remote user to add data to the database.

The system of the disclosure is further described with regard to FIG. 20 which is a system for inputting data to the CDPR 202. Here multiple users 203, which can be a remote user such as a laboratory, a breeder, an owner, hospital, agent, or an operator of the CDPR 202 accesses the system through module 204 which, in turn, accesses the CDPR 202. Appropriate access request and access enable messages are sent. Within the CDPR 202 there is a physical nutrition or phenotype module 200, a genetic or genotype data module 201, and other database modules 207, etc. After accessing the CDPR 202, additional data can be added to the modules 200, 201, 207, etc. through any of the users 203, if authorized. Depositing data into each of the modules 200, 201 and 207 can optionally require the payment to the operator of the CDPR 202 as is indicated by block 205. This system can function in the same manner as the retrieval of data from CDPR 202.

The stored data in each of the blocks 200, 201, and 207 can be set up as indicated by block 232 in a manner which is restricted or unrestricted to selected users 203. This may be necessary according to the protocols governing the inputted data to the different databases. In some cases, the waiving of deposit fees is made in the interest of freedom of the database to subsequent users who wish to retrieve data from the database. After storage of the data as indicated by block 234, the user 203 exits CDPR 202 as indicated by block 233.

As is apparent, the physical nutrition or phenotype profile of subject animals is dynamic and grows as more data is added into the system. Likewise, the genetic genotype database also grows as increasing research of particular subjects, breeds, and the like is obtained. The deposit of new information into the CDPR 202 is regulated in a manner that the data cannot distort the databases 202 in an in appropriate manner. Likewise, users 203 cannot access the secured databases within CDPR 202 in an inappropriate manner.

Different algorithms regulate the relationship between the nutrition profile, the genetic data, and other data relating to animals. These algorithms determine the probabilities, possibilities, and likelihood of disorders and disease in subject animals and offspring animals. They are used as predictors of the future evolvement of nutrition of the animal.

Analyzing the data from the CDPR 102 in the manner of the present disclosure permits for genetic screening, nutrition assessment profiling, and the diagnostic, prophylactic, and therapeutic management of animals.

An exemplary server performs all the operations of a conventional database system and performs additional operations in accordance with the present disclosure as has been discussed. The server includes a central processing unit (CPU) together with associated memory for processing information about different animal species and history. The inquiries concern animal species and history and inquiries and requests for nutrition profiling and genetic information, and providing nutrition profiles and genetic information. The CPU is coupled to the database and to users via a communications port. The CPU is also coupled to an electronic mail processor for processing and storing (in a storage device) e-mail messages transmitted between the CPU and various agents, users and the like. The CPU is further coupled to a data storage device. A data storage device may include a variety of the databases. The system permits for the requesting, storing and providing of data with respect to animal phenotypic information and genetic information. The format and content of the databases have been discussed in detail.

Figure 21:
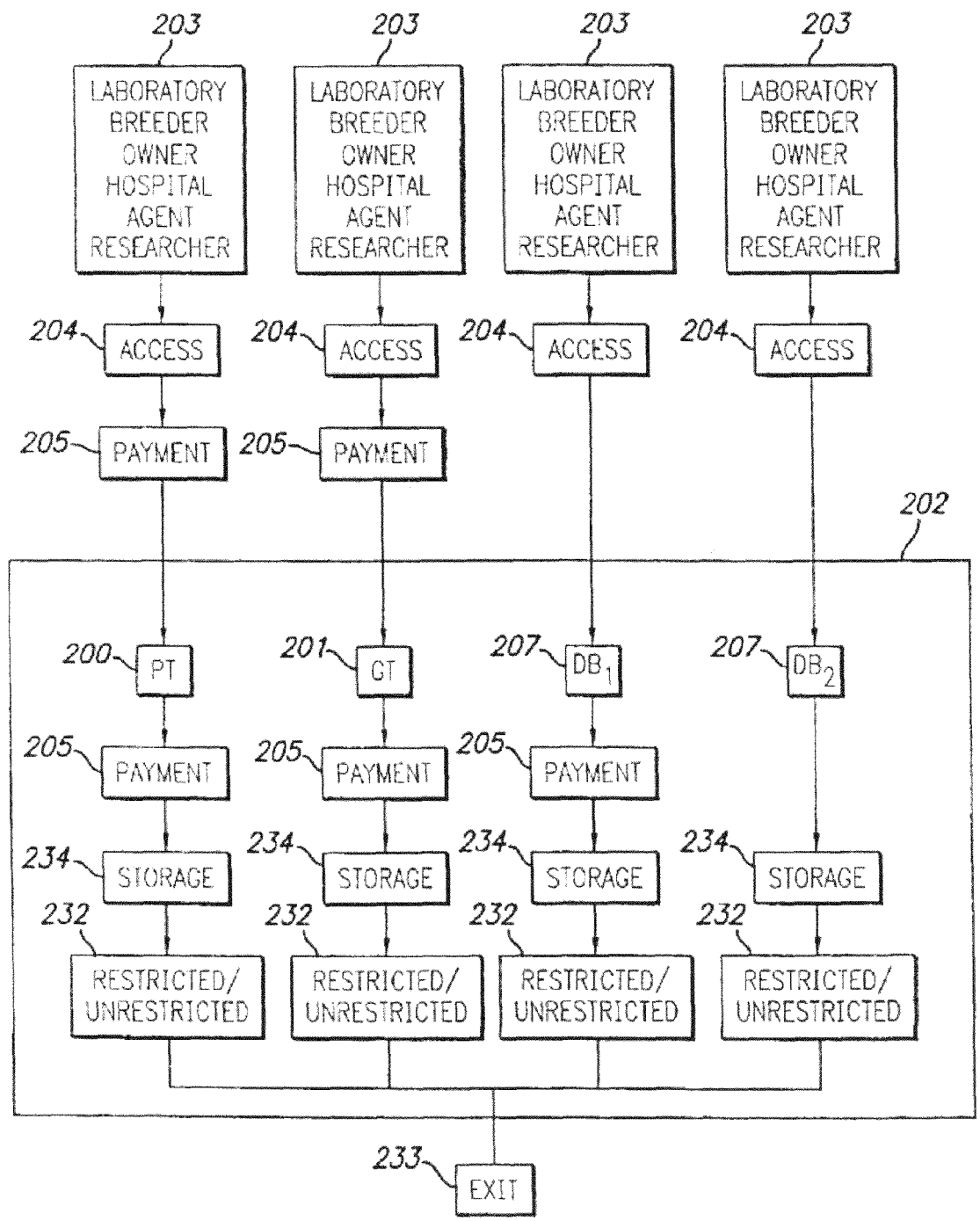
FIG. 21 is a flow chart illustrating an exemplary process by which the laboratory dynamically contributes, transmits and receives data associated with health assessment and genetic data to the CDPR.

FIG. 21 presents an overview of the laboratory instruments apparatus, system, and method operable with the present disclosure in relation to a CDPR 202. The present disclosure allows access by remote users with computers or processors 100 to receive and access data on specimens. Using the Internet 6 or other computer network or communication link capability, the remote user 8 sends a message to request access to the services provided by the laboratory or operator which has a CDPR 202. If access to the CDPR 202 is granted, a message is sent to the remote user computers 100. This message includes instructions enabling the remote user 8 to define and access data stored in the CDPR 202.

In one form of the disclosure, the desired data is based on the submission of test specimens of a specific animal to the laboratory. In some other cases nutrition profile test data 200 can be inputted into the CDPR 202 having the genetic database 201. The CDPR 202 can perform an analysis and correlation between the nutrition profile database 200 and the genetic database 201.

Using the communications link, the remote user 8 communicates with the laboratory or the CDPR 202. Specimens can be packaged and physically transported to the laboratory site via commercially available common carriers, such as the postal service or courier services. When the packages arrive, the laboratory places them in storage, or the tests are performed. Instruments 300 perform the tests to obtain. data as specified by the remote user 8. The biohazardous samples can be disposed of a waste material. The test results, or output is provided as part of a nutrition profile database 200 of the CDPR 202 and is available to the remote user 8.

If desired, the remote user 8 can arrange to have the data stored in the CDPR 202, made available to other remote users 8. The remote user 8 can also request the laboratory to perform analysis on the nutrition profile data 200 generated.

In one embodiment, the communications link is a computer network and the message transfer modality is, for instance, the Internet 6, and/or an Intranet and/or an Extranet. The network systems are particularly suited to the application described herein since it offers global or widespread accessibility and high speed data transfer of large amounts of information.

A security unit allows remote users to designate who has permission to view or use their data. Feasible options for these information management requirements include: access by the submitting remote users only, access by certain designated researchers and collaborators, time-embargoed data followed by wider access, and unrestricted access by all.

A commerce unit can implement functions related to the business aspects of the CDPR facility, including billing, inventory management of support materials.

A multimedia unit comprises means to store, manipulate, and present audio, graphical, video information. This information may include a video explaining how the CDPR is used, a visual depiction of the data, methodology, or a comment regarding the background of the data. The multimedia unit may also implement subscription functions, so that updated data automatically provided to remote users or other interested parties.

The operations performed by the present disclosure begins when the controller receives an access request message from the remote user via a communication link. Using information in the access request message and any other available information, the controller determines if the remote user is authorized to access the CDPR 202. If so, an access enabling message is transmitted from the controller to the remote user 8. The access enabling message can comprise a set of computer instructions transmitted over the Internet 6 which is downloaded into the remote user memory for execution by the remote user processor. These instructions may be enabling, that is, they may allow direct communication between the remote user 8 and the CDPR 202 with no further need for the controller. In another embodiment, the access enabling message may simply comprise a password or other enabling message which allows the remote user 8 to proceed. The remote user 8 can access or submit data to the CDPR 202 according to different protocols and regimes and security arrangements.

Different forms of expert system computing and software programming can be used to determine the relationship of the data bases and data. Parallel distributed processing, and neuromorphic systems, such as neural networks can be used. They are good pattern recognition engines and robust classifiers, with the ability to generalize in making decisions about imprecise input data. There are multitudes of different types of networks such as a multilayer perception which is generally trained with the back propagation of error algorithm, learning vector quantization, radial basis function, Hopfield, and Kohonen. Some are feed forward while others are recurrent (i.e., implement feedback) depending on how data is processed through the network. Some may require training while others are unsupervised or self-organizing. This can be implemented in software or in specialized hardware.

Alternatively or additionally fuzzy logic can be used due to the dynamic nature of the data applications, rules and functions. Such logic is adaptive to the changing environment. This logic and the neural networks can be integrated in the system.

Adaptive Logic Networks technology is an effective alternative or additional technology. The Adaptive Logic Network is neuro-computing capable of modeling complex non-linear systems by using piece-wise linear data. The inputs to an Adaptive Logic Network may be the data from large databases as described, observations recorded by a scientist, veterinarian or owner. The outputs of an Adaptive Logic Network can be used for analysis, prediction, or real-time management.

Conclusion

As is clear, the tests above relate to at least one of endocrine function, immunologic function, gastrointestinal function and nutritional analysis, metabolism, paternity, DNA fingerprinting, and the functional genomic profile. These data are relevant to the likely morbidity, likely longevity, and/or the potential risk for disease or disorder for the animal provide useful information. This is in a manner previously not obtained.

As the above demonstrates, there is a need for providing data analysis and dissemination services to a wide variety of globally-distributed remote users. There is a need for providing a system for inputting, storing and retrieving data related to animal nutrition assessment and genetics in a manner which permits for the effective use of this information.

The system also permits for the access to the genetic and/or phenotype data through a password and a system whereby access to the data generates a fee. This system permits for the access or to provide data with regard to credit cards or the like to ensure that the fee is transmitted automatically to a banking system for the account of the database when such data is accessed.

This system also provides for a situation wherein payments can be made by credit card for requests to perform nutrition assessment profiles and secure genomic mapping and genetic screening information. Such bioinformatics system can also permit for the automatic payment for such services and products to the banking system of the database or laboratory. As such, the database may require that the payments be guaranteed, for instance by supplying a credit card number with a request for performance of services and a product, and for the retrieval of such data.

A user can submit a request to the database in any number of ways. For example, the request can be submitted via on-line direct connection, namely through a computer network such as the Internet. An intermediate researcher such as a veterinarian or scientist other than the owner could also submit the request on behalf of the owner using the e-mail capabilities of the central database system. Alternatively, the user can submit the data via an interactive voice response unit coupled to the database system of the supplier. In some situations, the database supplier can decide whether to supply the nutrition assessment information and/or genomic mapping and genetic screening information based on the criteria of the user or its intermediary agent. Such user or intermediary agent can be notified of the decision via the interactive response unit or a live operator.

The user or agent can log into the database system and obtain the necessary records relating to an animal physical nutrition and/or genetic ancestry or offspring. The database system can transmit in real time or on a periodic basis as determined, thereby, providing information regarding the nutrition assessment or the genetic background and forward this information to the user and/or its intermediary agent.

The data storage devices of the disclosure include a variety of databases including a database relating to the phenotypic data of a particular species, a database relating to nutrition assessment or other phenotypic data of particular animals in a particular species, and genetic characteristics of different species and different family trees relating to different species. The family trees would contain information including the origin, genomic map, and parental lines of a species and records of nutrition and performance of a species. These databases are interrelated in an analytical manner and in accordance with different algorithms of permutations and probabilities to facilitate useful output information based on the combination of data in the genotypic and the phenotypic databases, and the selected databases.

Many other examples of the disclosure exist, each differing from others in matters of detail only. The disclosure is to be determined solely by the following claims.

In the specification, there have been disclosed typical preferred embodiments of the disclosure and, although specific terms are employed, they are used in a generic and descriptive sense only and not for purposes of limitation, the scope of the disclosure being set forth in the claims. Many modifications and variations of the disclosure are possible in light of the above teachings. It is therefore to be understood that within the scope of the appended claims the disclosure may be practiced otherwise than as specifically described.

Some typical embodiments of the disclosure have been described. Many more examples, modifications and variations of the disclosure are possible in light of the above teachings. For instance, although the disclosure and the claims indicate specific steps to perform the invention, the steps described are not limited to a particular sequence of performance and in some circumstances two or more of these steps could be undertaken simultaneously. It is therefore to be understood that within the scope of the appended claims the disclosure may be practiced otherwise than as specifically described, and the scope of the disclosure is set out in the claims.

We claim:

1. A method of analyzing the diagnostic genetic profile of a non-human animal comprising:
   (a) providing a genotypic database for the species of the non-human animal subject or a selected group of the non-human species;
   (b) obtaining animal phenotypic data;
   (c) correlating the database of (a) with the data of (b) to determine a relationship between the database of (a) and the data of (b); and
   (d) determining a diagnostic genetic profile of the animal or selected group of animals based on the correlating step (c), and selecting the biologically active nutrient from an obtained molecular dietary signature, the molecular dietary signature being a variation of expression of a set of genes which may differ for the genotype of each animal or selected group of animals.

2. A method of claim 1 comprising:
   (f) using a "reference" dataset containing the functional genomic profiles of biological samples for the multiple genotypes of different animals or groups of animals in varying physiological conditions;
   (g) using a "target group" dataset containing the functional genomic profiles of biological samples for the multiple genotypes of different animals or groups of animals in varying pathophysiological conditions;

(h) using a "nutrient" dataset comprising the variable effects of nutritional components on a functional genomic profile of an animal or a group of animals of different genotypes, the different genotypes that are responsive differently to the same nutritional components; and (i) relating the "reference" or "target group" datasets with the "nutrient" datasets, to derive a nutrient for the selected animal genotypes to prevent, or treat, or control, or modulate a state of physiological homeostasis or pathophysiological condition of the animal or a group of animals.

3. The method of claim 1 including the step of reporting the determination on a communications network including the Internet.

4. The method of claim 1 including the step of reporting the determination on a communications network including the Internet, and obtaining payment for the report through the Internet.

5. A method of determining a nutritional regime for a non-human animal comprising the steps of: claim 1 to determine a relationship between the databases; and determining the nutritional regimen for the animal based on the correlating step.

6. A method of determining a nutritional regime for a non-human animal comprising the steps of: claim 2 to determine a relationship between the databases and determining the nutritional regimen for the animal based on the correlating step.

7. A method as claimed in claim 1 wherein the animal is either a canine or a feline; the canine or feline is from the group consisting of one or more of breed type, specific breed, chronological age, physiological age, activity level, state of wellness, and state of disease.

8. A method as claimed in claim 2 wherein the condition is autoimmunity, anxiety, arthritis, depression, variable body condition score, immune suppression, or inflammation.

9. A method as claimed in claim 1, wherein the data of the animal is one or more data items related to genotype, selected from the group consisting of breed, breed(s) of parents, pedigree, sex, coat type, and evident hereditary conditions and disorders and the phenotypic data are selected from the group consisting of age, weight, veterinary medical history, reproductive history, present wellness or disease state, appetite, physical activity level, mental acuity, behavioral abnormalities and disposition.

10. A method as claimed in claim 2 wherein the reference data is data selected from group of animals with different genotypes in physiological homeostasis and includes at least one of DNA, RNA, proteins, metabolites and biomarkers.

11. A method as claimed in claim 2, wherein the target group data is data selected from groups of animals with different genotypes in non-physiological homeostasis and includes at least one of DNA, RNA, proteins, metabolites and biomarkers.

12. A method as claimed in claim 2, wherein the nutrient data is data selected from groups of animals with different genotypes, the different genotypes being responsive differently to the same nutritional components, and includes at least one of DNA, RNA, proteins, metabolites and biomarkers.

13. A method as claimed in claim 2, wherein the identified nutrient is a food, a supplement, a nutraceutical selected to promote wellness by enhancing an aspect of health of one or more animals and wherein wellness is promoted by preventing, attenuating or eliminating at least one disease state in one or more animals.

14. A method of diagnosing a healthy, unhealthy or physiological disorder, or a predisposition to disease or physiological disorder for an individual animal, comprising:

(a) using a "reference" dataset containing functional genomic profiles of biological samples of the genotypes of different animals of the species, the different animals being healthy animals;

(b) selecting a "target group" dataset containing the functional genomic profile of biological samples of the genotypes of different animals, the different animals being unhealthy animals;

(c) using a "biologically active nutrient" dataset comprising different effects of biologically active nutritional components on functional genomic profiles of the different animals of different genotypes from those of the target group (b), the different genotypes being differently responsive to the same biologically active nutritional components;

(d) having the reference group or target group include the individual animal; and (e) relating at least one of the "reference" or "target group" datasets with the "biologically active nutrient" dataset to identify a biologically active nutrient for the selected animal genotype to prevent, treat, control, or modulate a state of physiological homeostasis or pathophysiological condition of the individual animal in the reference group or target group.

15. A method as claimed in claim 14 wherein this diagnosis results in prescribing a treatment or prophylaxis for the subject based on the diagnosis.

16. A method of diagnosing a healthy, unhealthy or physiological disorder, or a predisposition to disease or physiological disorder for animals, comprising:

(a) using a "reference" dataset containing functional genomic profiles of biological samples of the genotypes of different animals of the species, the different animals being healthy animals;

(b) selecting a "target group" dataset containing the functional genomic profile of biological samples of the genotypes of different animals, the animals being unhealthy animals;

(c) using a "biologically active nutrient" dataset comprising different effects of biologically active nutritional components on functional genomic profiles of-the different animals of different genotypes from those of the target group (b), the different genotypes being differently responsive to the same biologically active nutritional components;

(d) having the reference group or target group include the animals; and (e) relating at least one of the "reference" or "target group" datasets with the "biologically active nutrient" dataset to identify a biologically active nutrient for the selected animal genotypes to prevent, treat, control, or modulate a state of physiological homeostasis or pathophysiological condition of the animal in the reference group or target group., and the relating being by using an analysis of gene or protein expression or the metabolytes in the biological sample of the target group.

17. A method as claimed in claim 16 wherein this diagnosis results in prescribing a treatment or prophylaxis for the subject based on the diagnosis.

18. A method of identifying a pharmacological product for an individual animal having a genotype, comprising:
(a) using a "reference" dataset containing functional genomic profiles of biological samples of the genotypes of different animals of the species, the different animals being healthy animals;
(b) selecting a "target" dataset containing the functional genomic profile of biological samples of the genotypes of different animals, the different animals being unhealthy animals;
(c) using a "pharmacological product" dataset comprising different effects of pharmacological product on functional genomic profiles of the different animals of different genotypes from those of the target group (b), the different genotypes being differently responsive to the same pharmacological product;
(d) having the reference dataset or target dataset include an individual animal for which the biologocallly active nutrient is to be identified; and
(e) relating at least one of the "reference" or "target group" datasets with the pharmacological product dataset to identify pharmacological product. is for the selected animal genotype to prevent, treat, control, or modulate a state of physiological homeostasis or pathophysiological condition of the individual animal in the reference dataset or target group.

19. A method as claimed in claim 18 wherein the identification is based on the molecular dietary signature being the expression of a gene or a set of genes which may differ for the genotypes of different animals of the same species, and the nutrient identification includes the molecular dietary signature that the biologically active nutrient induces in the individual animal.

20. A method as claimed in claim 18, wherein the reference dataset includes data selected from group of animals with different genotypes in physiological homeostasis and includes at least one of DNA, RNA, proteins, metabolites and biomarkers.

21. A method as claimed in claim 19, wherein the reference dataset includes data selected from group of animals with different genotypes in physiological homeostasis and includes at least one of DNA, RNA, proteins, metabolites and biomarkers.

22. A method as claimed in claim 18, wherein the target dataset includes data selected from groups of animals with different genotypes in non physiological homeostasis and includes at least one of DNA, RNA, proteins, metabolites and biomarkers.

23. A method as claimed in claim 19, wherein the target dataset includes data selected from groups of animals with different genotypes in non physiological homeostasis and includes at least one of DNA, RNA, proteins, metabolites and biomarkers.

24. A method of identifying a pharmacological product for animals, comprising:
(a) using a "reference" dataset containing functional genomic profiles of biological samples of the genotypes of different animals of the species, the different animals being healthy animals;
(b) selecting a "target group" dataset containing the functional genomic profile of biological samples of the genotypes of different animals, the animals being unhealthy animals;
(c) using a "pharmacological product" dataset comprising different effects of pharmacological product on functional genomic profiles of the different animals of different genotypes from those of the target group (b), the different genotypes being differently responsive to the same pharmacological product;
(d) having the reference group or target group include the animals; and
(e) relating at least one of the "reference" or "target group" datasets with the pharmacological product dataset to identify a biologically active nutrient for the selected animal genotypes to prevent, treat, control, or modulate a state of physiological homeostasis or pathophysiological condition of the animal in the reference dataset or target group, and the analyzing the gene or protein expression or the metabolite expression in the biological samples of the target dataset.

* * * * *